US008350108B2

(12) United States Patent
Cortright et al.

(10) Patent No.: US 8,350,108 B2
(45) Date of Patent: Jan. 8, 2013

(54) SYNTHESIS OF LIQUID FUELS FROM BIOMASS

(75) Inventors: Randy D. Cortright, Madison, WI (US); Paul G. Blommel, Oregon, WI (US); Michael J. Werner, Portage, WI (US); Matthew R. Vanstraten, Madison, WI (US)

(73) Assignee: Virent, Inc., Madison, WI (US)

( * ) Notice: Subject to any disclaimer, the term of this patent is extended or adjusted under 35 U.S.C. 154(b) by 751 days.

(21) Appl. No.: 12/548,963

(22) Filed: Aug. 27, 2009

(65) Prior Publication Data
US 2010/0076233 A1 Mar. 25, 2010

Related U.S. Application Data

(60) Provisional application No. 61/092,340, filed on Aug. 27, 2008.

(51) Int. Cl.
C07C 2/54 (2006.01)
C07C 1/24 (2006.01)

(52) U.S. Cl. ........ 585/331; 585/332; 585/638; 585/709; 585/721

(58) Field of Classification Search .................. 585/331, 585/332, 638, 709, 721
See application file for complete search history.

(56) References Cited

U.S. PATENT DOCUMENTS

| 2,965,679 A | 12/1960 | Conradin et al. |
| 3,894,107 A | 7/1975 | Butter et al. |
| 4,013,734 A | 3/1977 | Kim |
| 4,223,001 A | 9/1980 | Novotny et al. |
| 4,380,679 A | 4/1983 | Arena |
| 4,380,680 A | 4/1983 | Arena |
| 4,382,150 A | 5/1983 | Arena |
| 4,401,823 A | 8/1983 | Arena |
| 4,456,779 A | 6/1984 | Owen et al. |
| 4,476,331 A | 10/1984 | Dubeck et al. |
| 4,487,980 A | 12/1984 | Arena |
| 4,496,780 A | 1/1985 | Arena |
| 4,503,274 A | 3/1985 | Arena |
| 4,541,836 A | 9/1985 | Derderian |
| 4,543,435 A | 9/1985 | Gould et al. |
| 4,554,260 A | 11/1985 | Pieters et al. |
| 4,642,394 A | 2/1987 | Che |
| 4,717,465 A | 1/1988 | Chen et al. |
| 4,828,812 A | 5/1989 | McCullen et al. |
| 4,885,421 A | 12/1989 | Harandi et al. |
| 4,919,896 A | 4/1990 | Harandi et al. |

(Continued)

FOREIGN PATENT DOCUMENTS
CA    1201080 A    2/1986
(Continued)

OTHER PUBLICATIONS

Yoshida et al., "Gasification of Cellulose, Xylan, and Lignin Mixtures in Supercritical Water" 2001 Ind. Eng. Chem. Res. 40:5469-5474.
(Continued)

Primary Examiner — Thuan D Dang
(74) Attorney, Agent, or Firm — Quarles & Brady LLP

(57) ABSTRACT

Processes and reactor systems are provided for the conversion of oxygenated hydrocarbons to paraffins useful as liquid fuels. The process involves the conversion of water soluble oxygenated hydrocarbons to oxygenates, such as alcohols, furans, ketones, aldehydes, carboxylic acids, diols, triols, and/or other polyols, followed by the subsequent conversion of the oxygenates to paraffins by dehydration and alkylation. The oxygenated hydrocarbons may originate from any source, but are preferably derived from biomass.

57 Claims, 8 Drawing Sheets

U.S. PATENT DOCUMENTS

| | | |
|---|---|---|
| 4,935,568 A | 6/1990 | Harandi et al. |
| 5,001,292 A | 3/1991 | Harandi et al. |
| 5,006,131 A | 4/1991 | Karafian et al. |
| 5,019,135 A | 5/1991 | Sealock, Jr. et al. |
| 5,026,927 A | 6/1991 | Andrews et al. |
| 5,095,159 A | 3/1992 | Harandi et al. |
| 5,105,044 A | 4/1992 | Han et al. |
| 5,130,101 A | 7/1992 | Harandi et al. |
| 5,139,002 A | 8/1992 | Lynch et al. |
| 5,149,884 A | 9/1992 | Brenner et al. |
| 5,177,279 A | 1/1993 | Harandi |
| 5,214,219 A | 5/1993 | Casale et al. |
| 5,238,898 A | 8/1993 | Han et al. |
| 5,306,847 A | 4/1994 | Gehrer et al. |
| 5,326,912 A | 7/1994 | Gubitosa et al. |
| 5,344,849 A | 9/1994 | Ayasse |
| 5,354,914 A | 10/1994 | Gubitosa et al. |
| 5,496,786 A | 3/1996 | Gubitosa et al. |
| 5,504,259 A | 4/1996 | Diebold et al. |
| 5,543,379 A | 8/1996 | Gubitosa et al. |
| 5,578,647 A | 11/1996 | Li et al. |
| 5,600,028 A | 2/1997 | Gubitosa et al. |
| 5,616,154 A | 4/1997 | Elliott et al. |
| 5,616,817 A | 4/1997 | Schuster et al. |
| 5,635,145 A | 6/1997 | Den Hartog et al. |
| 5,651,953 A | 7/1997 | Yokoyama et al. |
| 5,660,602 A | 8/1997 | Collier, Jr. et al. |
| 5,666,923 A | 9/1997 | Collier, Jr. et al. |
| 5,787,864 A | 8/1998 | Collier, Jr. et al. |
| 5,817,589 A | 10/1998 | de Agudelo et al. |
| 5,861,137 A | 1/1999 | Edlund |
| 5,959,167 A | 9/1999 | Shabtai et al. |
| 6,054,041 A | 4/2000 | Ellis et al. |
| 6,059,995 A | 5/2000 | Topsoe et al. |
| 6,152,975 A | 11/2000 | Elliott et al. |
| 6,171,992 B1 | 1/2001 | Autenrieth et al. |
| 6,172,272 B1 | 1/2001 | Shabtai et al. |
| 6,207,132 B1 | 3/2001 | Lin et al. |
| 6,235,797 B1 | 5/2001 | Elliot et al. |
| RE37,329 E | 8/2001 | Gubitosa et al. |
| 6,280,701 B1 | 8/2001 | Autenrieth et al. |
| 6,291,725 B1 | 9/2001 | Chopade et al. |
| 6,323,383 B1 | 11/2001 | Tsuchida et al. |
| 6,361,757 B1 | 3/2002 | Shikada et al. |
| 6,372,680 B1 | 4/2002 | Wu et al. |
| 6,373,680 B1 | 4/2002 | Riskin |
| 6,387,554 B1 | 5/2002 | Verykios |
| 6,397,790 B1 | 6/2002 | Collier, Jr. |
| 6,413,449 B1 | 7/2002 | Wieland et al. |
| 6,429,167 B1 | 8/2002 | Maeno et al. |
| 6,440,895 B1 | 8/2002 | Tonkovich et al. |
| 6,479,428 B1 | 11/2002 | Tonkovich et al. |
| 6,479,713 B1 | 11/2002 | Werpy et al. |
| 6,486,366 B1 | 11/2002 | Ostgard et al. |
| 6,508,209 B1 | 1/2003 | Collier, Jr. |
| 6,570,043 B2 | 5/2003 | Elliott et al. |
| 6,582,667 B1 | 6/2003 | Ogata et al. |
| 6,607,707 B2 | 8/2003 | Reichman et al. |
| 6,670,300 B2 | 12/2003 | Werpy et al. |
| 6,677,385 B2 | 1/2004 | Werpy et al. |
| 6,699,457 B2 | 3/2004 | Cortright et al. |
| 6,739,125 B1 | 5/2004 | Mulligan |
| 6,749,828 B1 | 6/2004 | Fukunaga |
| 6,762,149 B2 | 7/2004 | Tonkovich et al. |
| 6,765,101 B1 | 7/2004 | Bhasin et al. |
| 6,841,085 B2 | 1/2005 | Werpy et al. |
| 6,953,873 B2 | 10/2005 | Cortright et al. |
| 6,964,757 B2 | 11/2005 | Cortright et al. |
| 6,964,758 B2 | 11/2005 | Cortright et al. |
| 6,969,506 B2 | 11/2005 | Tonkovich et al. |
| 6,982,328 B2 | 1/2006 | Werpy et al. |
| 7,022,824 B2 | 4/2006 | Vanoppen et al. |
| 7,038,094 B2 | 5/2006 | Werpy et al. |
| 7,070,745 B2 | 7/2006 | Van Der Meer et al. |
| 7,112,312 B2 | 9/2006 | Chou |
| 7,186,668 B2 | 3/2007 | Werpy et al. |
| 7,199,250 B2 | 4/2007 | Werpy et al. |
| 7,232,935 B2 | 6/2007 | Jakkula et al. |
| 7,273,957 B2 | 9/2007 | Bakshi et al. |
| 7,288,685 B2 | 10/2007 | Marker |
| 7,297,814 B2 | 11/2007 | Yada et al. |
| 7,355,083 B2 | 4/2008 | Tuck et al. |
| 7,520,909 B2 | 4/2009 | Rogers |
| 7,578,927 B2 | 8/2009 | Marker et al. |
| 7,615,652 B2 | 11/2009 | Holladay et al. |
| 7,618,612 B2 | 11/2009 | Cortright et al. |
| 7,649,099 B2 | 1/2010 | Holladay et al. |
| 7,652,131 B2 | 1/2010 | Werpy et al. |
| 7,663,004 B2 | 2/2010 | Suppes et al. |
| 7,674,916 B2 | 3/2010 | Werpy et al. |
| 7,692,001 B2 | 4/2010 | Holcomb |
| 7,767,867 B2 | 8/2010 | Cortright |
| 2003/0100807 A1 | 5/2003 | Shabtai et al. |
| 2003/0115792 A1 | 6/2003 | Shabtai et al. |
| 2003/0175561 A1 | 9/2003 | Lightner |
| 2005/0064560 A1 | 3/2005 | Werpy et al. |
| 2005/0203195 A1 | 9/2005 | Wang et al. |
| 2005/0244329 A1 | 11/2005 | Casanave et al. |
| 2006/0013759 A1 | 1/2006 | Jiang et al. |
| 2006/0024539 A1 | 2/2006 | Dumesic et al. |
| 2007/0123739 A1 | 5/2007 | Crabtree et al. |
| 2007/0135301 A1 | 6/2007 | Holcomb, Jr. |
| 2008/0216391 A1 | 9/2008 | Cortright et al. |
| 2008/0300434 A1 | 12/2008 | Cortright et al. |
| 2008/0300435 A1 | 12/2008 | Cortright et al. |
| 2009/0211942 A1 | 8/2009 | Cortright et al. |
| 2010/0008840 A1 | 1/2010 | Zhong et al. |
| 2010/0076233 A1 | 3/2010 | Cortright et al. |

FOREIGN PATENT DOCUMENTS

| | | |
|---|---|---|
| EP | 0204354 A1 | 12/1986 |
| EP | 0323663 B2 | 9/1994 |
| EP | 1454671 A1 | 9/2004 |
| EP | 1724325 A1 | 11/2006 |
| FR | 2857003 A1 | 1/2005 |
| GB | 2097390 A | 11/1982 |
| JP | 2004344721 A | 12/2004 |
| WO | 9429013 A1 | 12/1994 |
| WO | 9910450 A1 | 3/1999 |
| WO | 9961369 A1 | 12/1999 |
| WO | 0200341 A2 | 1/2002 |
| WO | 03045841 A1 | 6/2003 |
| WO | 2004039918 A2 | 5/2004 |
| WO | 2004052813 A1 | 6/2004 |
| WO | 2005037423 A1 | 4/2005 |
| WO | 2006100584 A2 | 9/2006 |
| WO | 20060119357 A2 | 11/2006 |
| WO | 2007027832 A2 | 3/2007 |
| WO | 2007053705 A2 | 5/2007 |
| WO | 2007075476 A2 | 7/2007 |
| WO | 2007099161 A1 | 9/2007 |
| WO | 2008109877 A1 | 9/2008 |

OTHER PUBLICATIONS

United States Patent and Trademark Office, Office Action Summary and Detailed Action, U.S. Appl. No. 11/800,671, Dec. 26, 2008.

Applicant, Response to Restriction Requirement, U.S. Appl. No. 11/800,671, Jan. 26, 2009.

United States Patent and Trademark Office, Office Action Summary and Detailed Action, U.S. Appl. No. 11/800,671, Apr. 8, 2009.

Applicant, Response to Non-Final Office Action, U.S. Appl. No. 11/800,671, Aug. 10, 2009.

United States Patent and Trademark Office, Issue Notification, U.S. Appl. No. 11/800,671, Aug. 3, 2010.

United States Patent and Trademark Office, Office Action Summary and Detailed Action, U.S. Appl. No. 12/158,635, Jan. 4, 2011.

United States Patent and Trademark Office, Office Action Summary and Detailed Action, U.S. Appl. No. 12/044,837, Aug. 12, 2010.

United States Patent and Trademark Office, Interview Summary, U.S. Appl. No. 12/044,837, Oct. 28, 2010.

Applicant, Response to Non-Final Office Action, U.S. Appl. No. 12/044,837, Nov. 12, 2010.

Applicant, Supplemental Response to Non-Final Office Action, U.S. Appl. No. 12/044,837, Jan. 5, 2011.

United States Patent and Trademark Office, Office Action Summary and Detailed Action, U.S. Appl. No. 12/044,908, Aug. 12, 2010.
United States Patent and Trademark Office, Interview Summary, U.S. Appl. No. 12/044,908, Oct. 29, 2010.
Applicant, Response to Non-Final Office Action, U.S. Appl. No. 12/044,908, Nov. 12, 2010.
Applicant, Supplemental Response to Non-Final Office Action, U.S. Appl. No. 12/044,908, Jan. 5, 2011.
United States Patent and Trademark Office, Office Action Summary and Detailed Action, U.S. Appl. No. 12/044,876, Aug. 16, 2010.
United States Patent and Trademark Office, Interview Summary, U.S. Appl. No. 12/044,876, Oct. 28, 2010.
Applicant, Response to Non-Final Office Action, U.S. Appl. No. 12/044,876, Nov. 12, 2010.
Applicant, Supplemental Response to Non-Final Office Action, U.S. Appl. No. 12/044,876, Jan. 5, 2011.
United States Patent and Trademark Office, Office Action Summary and Detailed Action, U.S. Appl. No. 12/834,306, Sep. 17, 2010.
Applicant, Response to Non-Final Office Action, U.S. Appl. No. 12/834,306, Dec. 15, 2010.
PCT International Search Report, Application No. PCT/US2007/011062, Sep. 16, 2008.
PCT International Preliminary Report on Patentability, Application No. PCT/US2007/011062, Nov. 11, 2008.
European Patent Office, Examination Report, Application No. 07870663.7, Oct. 22, 2010.
Ukraine Patent Office, Office Action, Application No. a 2008 12327, 2010.
Republic of South Africa, Letters Patent, Patent No. 2008/09194, Dec. 30, 2009.
Intellectual Property Office of New Zealand, Examination Report, Application No. 572113, Jun. 4, 2010.
PCT International Search Report, Application No. PCT/US2006/048030, Dec. 27, 2007.
PCT Written Opinion, Application No. PCT/US2006/048030, Jun. 21, 2008.
State Intellectual Property Office of the People's Republic of China, First Office Action (Translation), Application No. 200680048598.5, Jun. 11, 2010.
Applicant, Response to State Intellectual Property Office of the People's Republic of China First Office Action, Application No. 200680048598.5, Oct. 21, 2010 [includes AFD China Intellectual Property Law Office Oct. 22, 2010 letter; Quarles & Brady Oct. 13, 2010 letter; English version of Amended Claims].
State Intellectual Property Office of the People's Republic of China, Second Office Action (Translation), Application No. 200680048598.5, Jan. 10, 2011.
Patent Office of the Russian Federation, Office Action (Inquiry) of the State Examination, Applicaiton No. 2008127066, Nov. 15, 2010.
Ukraine Patent Office, Office Action, Application No. a 2008 09306, 2010.
Applicant, Response to Ukraine Patent Office Office Action, Application No. a 2008 09306, Dec. 2010 [includes Papula-Nevinpat Dec. 8, 2010 letter].
Ukraine Patent Office, Office Action, Application No. a 2008 09306, Jan. 2011.
Intellectual Property Office of New Zealand, Examination Report, Application No. 569246, Mar. 2, 2010.
PCT International Search Report and Written Opinion, Application No. PCT/US2007/088417, Dec. 2, 2008.
PCT International Preliminary Report on Patentability, Application No. PCT/US2007/088417, Jun. 24, 2009.
Intellectual Property Office of New Zealand, Examination Report, Application No. 577547, Sep. 17, 2010.
Republic of South Africa, Letters Patent, Patent No. 2009/04056, Apr. 28, 2010.
PCT International Search Report, Application No. PCT/US2008/056330, Jul. 10, 2008.
PCT International Preliminary Report on Patentability, PCT/US2008/056330, Sep. 8, 2009.
European Patent Office, Communication, Application No. 08731758.2, Apr. 2, 2009.

Applicant, Response to European Patent Office Apr. 2, 2009 Communication, Application No. 08731758.2, May 1, 2009.
European Patent Office, Communication, Application No. 08731758.2, Mar. 25, 2010.
Applicant, Response to European Patent Office Mar. 25, 2010, Communication, Application No. 08731758.2, Oct. 1, 2010.
Intellectual Property Office of New Zealand, Examination Report, Application No. 579525, Sep. 29, 2010.
Republic of South Africa, Letters Patent, Patent No. 2009/05916, Apr. 28, 2010.
PCT International Search Report and Written Opinion, Application No. PCT/US2010/040644, Feb. 4, 2011.
Agar, et al., "Abstract 2254—Influence of the Liquid Phase Physical Properties on Unsteady-State Hydrodynamics in Periodically Operated Trickle-Bed Reactors," European Congress of Chemical Engineering—6, Copenhagen Sep. 2007.
Badger, "Ethanol From Cellulose: A General Review," 2002 J. Janick and A. Whipkey (eds.), Trends in New Crops and New Uses, ASHA Press, Alexandria, VA, pp. 17-21.
Bardin, et al., "Acidity of Keggin-Type Heteropolycompounds Evaluated by Catalytic Probe Reactions, Sorption Microcalorimetry, and Density Functional Quantum Chemical Calculations" 1998 J. Phys. Chem. B 102:10817-10825.
Barrett, et al., "Single-Reactor Process for Sequential Aldol-Condensation and Hydrogenation of Biomass-Derived Compounds in Water," 2006 Applied Catalysis B: Environmental 66:111-118.
Brown, et al., "Carbon-Halogen Bond Scission and Rearrangement of Beta-Halohydrins on the Rh(111) Surface" 1994 J. Phys. Chem. 98:12737-12745.
Chaminand, et al., "Glycerol Hydrogenolysis on Heterogeneous Catalysts", 2004 Green Chemistry 6:359-361.
Chen, et al., "Liquid Fuel From Carbohydrates," Aug. 1986 Chemtech pp. 506-509.
Chiu, et al., "Distribution of Methanol and Catalysts Between Biodiesel and Glycerin Phases" 2005 AIChE Journal 51:1274-1278.
Chiu, et al., "Removal of Residual Catalyst from Simulated Biodiesel's Crude Glycerol for Glycerol Hydrogenolysis to Propylene Glycol" 2006 Ind. Eng. Chem. Res. 45:791-795.
Corma, et al., "Processing Biomass-Derived Oxygenates in the Oil Refinery: Catalytic Cracking (FCC) Reaction Pathways and Role of Catalyst," 2007 Journal of Catalysis 247:307-327.
Cortright, et al., "Hydrogen from Catalytic Reforming of Biomass-Derived Hydrocarbons in Liquid Water" 2002 Nature 418:964-967.
Crabtree, et. al., "Novel Catalysis for Glycol Manufacture", 2001.
Dasari, et al., "Low-Pressure Hydrogenolysis of Glycerol to Propylene Glycol" 2005 Applied Catalysis A: General 281:225-231.
Dass, et al., "A Comparative Study of the Conversion of Ethanol and of Ethylene Over the 'Mobil' Zeolite Catalyst, H-ZSM-5. An application of the Benzene Sequestration Test," 1989 Can. J. Chem. 67:1732-1734.
Davda, et al., "A Review of Catalytic Issues and Process Conditions for Renewable Hydrogen and Alkanes by Aqueous-Phase Reforming of Oxygenated Hydrocarbons Over Supported Metal Catalysts" 2005 Applied Catalysis B: Environmental 56:171-186.
Davda, et al., "Aqueous-Phase Reforming of Ethylene Glycol on Silica-Supported Metal Catalysts" 2003 Applied Catalysis B: Environmental 43:13-26.
Davda, et al., "Catalytic Reforming of Oxygenated Hydrocarbons for Hydrogen with Low Levels of Carbon Monoxide" 2003 Angew. Chem. Int. Ed., 42:4068-4071.
Davda, et al., "Renewable Hydrogen by Aqueous-Phase Reforming of Glucose" 2004 Chem. Commun., pp. 36-37.
Dos Santos, et al., "Performance of RuSn Catalysts Supported on Different Oxides in the Selective Hydrogenation of Dimethyl Adipate," 2005 Catalysis Today 107-108:250-257.
Elliott, et al., "Chemical Processing in High-Pressure Aqueous Environments. 7. Process Development for Catalytic Gasification of Wet Biomass Feedstocks" 2004 Ind. Eng. Chem. Res. 43:1999-2004.
Elliott, et al.. "Chemical Processing in High-Pressure Aqueous Environments. 6. Demonstration of Catalytic Gasification for Chemical Manufacturing Wastewater Cleanup in Industrial Plants" 1999 Ind. Eng. Chem. Res. 38:879-883.

Elliott, et al., "Liquid Fuels by Low-Severity Hydrotreating of Biocrude," 1996 Developments in Thermochemical Biomass Conversion 1:611-621.

Fraser, "Roadmap for Cellulosic Ethanol Production," U.S. Department of Energy, Jun. 2006.

Fukuoka, et al., "Catalytic Conversion of Cellulose into Sugar Alcohols," 2006 Angew. Chem. Int. Ed. 45:5161-5163.

Gayubo, et al., "Transformation of Oxygenate Components of Biomass Pyrolsis Oil on a HZSM-5 Zeolite. I. Alcohols and Phenols," 2004 Ind. Eng. Chem Res. 43:2610-2618.

Gayubo, et al., "Transformation of Oxygenate Components of Biomass Pyrolsis Oil on a HZSM-5 Zeolite. II. Aldehydes, Ketones, and Acids," 2004 Ind. Eng. Chem Res. 43:2619-2626.

Greer, "Creating Cellulosic Ethanol: Spinning Straw into Fuel," May 2005 eNews Bulletin.

Huber, et al., "Production of Liquid Alkanes by Aqueous-Phase Processing of Biomass-Derived Carbohydrates" 2005 Science 308:1446-1450.

Huber, et al., "Raney Ni-Sn Catalyst for H2 Production from Biomass-Derived Hydrocarbons," 2003 Science 300:2075-2077.

Huber, et al., "Renewable Alkanes by Aqueous-Phase Reforming of Biomass-Derived Oxygenates" 2004 Angew. Chem. Int. Ed., 43:1549-1551.

Huber, et al., "Synthesis of Transportation Fuels from Biomass: Chemistry, Catalysts, and Engineering" 2006 Chem. Rev. 106:4044-4098.

Kawai, et al., "Production of Hydrogen and Hydrocarbon From Cellulose and Water" 1981 Chemistry Letters pp. 1185-1188.

Kluson, et al. "Selective Hydrogenation over Ruthenium Catalysts" 1995 Applied Catalysis A: General 128:13-31.

Makarova, et al., "Dehydration of n-Butanol on Zeolite H-ZSM-5 and Amorphous Aluminosilicate: Detailed Mechanistic Study and the Effect of Pore Confinement" 1994 Journal of Catalysis 149:36-51.

Minowa, et al., "Hydrogen Production from Cellulose in Hot Compressed Water Using Reduced Nickel Catalyst: Product Distribution at Different Reaction Temperatures" 1998 J. of Chem. Eng. of Japan 31:488-491.

Minowa, et al., "Hydrogen Production from Wet Cellulose by Low Temperature Gasification Using a Reduced Nickel Catalyst" 1995 Chemistry Letters pp. 937-938.

Miyazawa, et al., "Glycerol Conversion in the Aqueous Solution under Hydrogen over Ru/C + an Ion-Exchange Resin and Its Reaction Mechanism" 2006 J. of Catalysis 240:213-221.

Nelson, et al., "Application of Direct Thermal Liquefaction for the Conversion of Cellulosic Biomass" 1984 Ind. Eng. Chem. Prod. Res. Dev. 23:471-475.

Oregon Cellulose-Ethanol Study, Appendix B Overview of Cellulose-Ethanol Production Technology 1998 pp. 57-60.

Roman-Leshkov, et al., "Production of Dimethylfuran for Liquid Fuels from Biomass-Derived Carbohydrates" 2007 Nature 447:982-986.

Rostrup-Nielsen, "Conversion of Hydrocarbons and Alcohols for Fuel Cells" 2001 Phys. Chern. Chern. Phys. 3:283-288.

Shabaker, et al., "Aqueous-Phase Reforming of Ethylene Glycol over Supported Platinum Catalysts" 2003 Catal. Lett., vol. 88, Nos. 1-2.

Shabaker, et al., "Aqueous-Phase Reforming of Methanol and Ethylene Glycol Over Alumina-Supported Platinum Catalysts" 2003 Journal of Catalysis 215:344-352.

Shabaker, et al., "Aqueous-Phase Reforming of Oxygenated Hydrocarbons Over Sn-Modified Ni Catalysts" 2004 Journal of Catalysis 222:180-191.

Shabaker, et al., "Sn-modified Ni Catalysts for Aqueous-Phase Reforming: Characterization and Deactivation Studies" 2005 Journal of Catalysis 231:67-76.

Shabaker, et al., "Kinetics of Aqueous-Phase Reforming of Oxygenated Hydrocarbons: Pt/Al2O3 and Sn-Modified Ni Catalysts" 2004 Ind. Eng, Chem. Res., 43:3105-3112.

Silva, et al., "Role of Catalyst Preparation on Determining Selective Sites for Hydrogenation of Dimethyl Adipate Over RuSn/Al2O3," 2006 J. of Molecular Catalysis A: Chemical 253:62-69.

Tsuchida, et al., "Direct Synthesis of n-Butanol from Ethanol over Nonstoichiometric Hydroxyapatite" 2006 Ind. Eng. Chem. Res. 45:8634-8642.

Wang, et al., "Catalytic Steam Reforming of Biomass-Derived Oxygenates: Acetic Acid and Hydroxyacetaldehyde" 1996 Applied Catalysis A: General 143:245-270.

Werpy, et al., "Top Value Added Chemicals from Biomass, vol. 1: Results of Screening for Potential Candidates from Sugars and Synthesis Gas," 2004 National Renewable Energy Laboratory, Pacific Northwest National Laboratory.

United States Patent and Trademark Office, Office Action, U.S. Appl. No. 11/961,280, Mar. 9, 2011.

Applicant, Response to Restriction Requirement (Mar. 9, 2011), U.S. Appl. No. 11/961,280, Apr. 11, 2011.

Olefin Carbon Number Distribution

US 8,350,108 B2

SYNTHESIS OF LIQUID FUELS FROM BIOMASS

CROSS REFERENCE TO RELATED APPLICATIONS

This application claims benefit of U.S. Provisional Application No. 61/092,340 filed on Aug. 27, 2008.

BACKGROUND

Significant amount of attention has been placed on developing new technologies for providing energy from resources other than fossil fuels. Biomass is a resource that shows promise as a fossil fuel alternative. As opposed to fossil fuel, biomass is also renewable.

One type of biomass is plant biomass. Plant biomass is the most abundant source of carbohydrate in the world due to the lignocellulosic materials composing the cell walls in higher plants. Plant cell walls are divided into two sections, primary cell walls and secondary cell walls. The primary cell wall provides structure for expanding cells and is composed of three major polysaccharides (cellulose, pectin, and hemicellulose) and one group of glycoproteins. The secondary cell wall, which is produced after the cell has finished growing, also contains polysaccharides and is strengthened through polymeric lignin covalently cross-linked to hemicellulose. Hemicellulose and pectin are typically found in abundance, but cellulose is the predominant polysaccharide and the most abundant source of carbohydrates.

Most transportation vehicles, whether boats, trains, planes and automobiles, require high power density provided by internal combustion and/or propulsion engines. These engines require clean burning fuels which are generally in liquid form or, to a lesser extent, compressed gases. Liquid fuels are more portable due to their high energy density and their ability to be pumped, which makes handling easier. This is why most fuels are liquids.

Currently, biomass provides the only renewable alternative for liquid transportation fuel. Unlike nuclear and wind applications, and for the most part solar resources, biomass is capable of being converted into a liquid form. Unfortunately, the progress in developing new technologies for producing liquid biofuels has been slow in developing, especially for liquid fuel products that fit within the current infrastructure. Although a variety of fuels can be produced from biomass resources, such as ethanol, methanol, biodiesel, Fischer-Tropsch diesel, and gaseous fuels, such as hydrogen and methane, these fuels require either new distribution technologies and/or combustion technologies appropriate for their characteristics. The production of these fuels also tend to be expensive and raise questions with respect to their net carbon savings.

Ethanol, for example, is made by converting the carbohydrate from biomass into sugar, which is then converted into ethanol in a fermentation process similar to brewing beer. Ethanol is the most widely used biofuel today with current capacity of 4.3 billion gallons per year based on starch crops, such as corn. Ethanol, however, has substantial disadvantages with respect its energy value as a fuel relative to the amount of energy needed for its production. Ethanol produced by fermentation is initially provided in a water solution at a volume of about 5% ethanol. The removal of this water is critical and energy-consuming, often requiring the use of natural gas or coal as a heat source. Ethanol also has less energy content than gasoline, thereby requiring more fuel and lower gas mileage. Ethanol is also corrosive to fuel systems and is not transportable in petroleum pipelines, resulting in its distribution over-the-road in tank trucks, which increases its overall cost and energy consumption. When considering the total energy consumed by farm equipment, cultivation, planting, fertilizers, pesticides, herbicides, petroleum-based fungicides, irrigation systems, harvesting, transportation to processing plants, fermentation, distillation, drying, transport to fuel terminals and retail pumps, and lower ethanol fuel energy content, the net energy content value added and delivered to consumers is very small.

Biodiesel is another potential energy source. Biodiesel can be made from vegetable oil, animal fats, waste vegetable oils, microalgae oils or recycled restaurant greases, and is produced through a process in which organically derived oils are combined with alcohol (ethanol or methanol) in the presence of a catalyst to form ethyl or methyl ester. The biomass-derived ethyl or methyl esters can then he blended with conventional diesel fuel or used as a neat fuel (100% biodiesel). Biodiesel is also expensive to manufacture, and poses various issues in its use and combustion. For example, biodiesel is not suitable for use in lower temperatures and requires special handling to avoid gelling in cold temperatures. Biodiesel also tends to provide higher nitrogen oxide emissions, and cannot be transported in petroleum pipelines.

Biomass can also be gasified to produce a synthesis gas composed primarily of hydrogen and carbon monoxide, also called syngas or biosyngas. Syngas produced today is used directly to generate heat and power, but several types of biofuels may be derived from syngas. Hydrogen can be recovered from syngas, or syngas can be catalytically converted to methanol. The gas can also be run through a biological reactor to produce ethanol or converted using Fischer-Tropsch catalyst into a liquid stream with properties similar to diesel fuel, called Fischer-Tropsch diesel. These processes are expensive and generate fuels that are not easily assimilated in current transportation technology. Processes capable of converting biomass using catalytic techniques would be especially advantageous due to its familiarity within the current fuel industry.

SUMMARY OF THE INVENTION

The invention provides methods and reactor systems for producing $C_{6+}$ paraffins from oxygenated hydrocarbons derived from biomass. The method generally involves: (1) catalytically reacting hydrogen, water and water soluble oxygenated hydrocarbons comprising $C_{2+}O_{2+}C_{2+}O_{1+}$ hydrocarbons in the presence of a deoxygenation catalyst at a deoxygenation temperature and deoxygenation pressure to produce an oxygenate comprising $C_{2+}O_{1-3}$ hydrocarbons; (2) catalytically reacting the $C_{2+}O_{1-3}$ hydrocarbons in the presence of a dehydration catalyst at a dehydration temperature and dehydration pressure to produce a reaction stream comprising $C_{2+}$ olefins; and (3) catalytically reacting the $C_{2+}$ olefins with a stream of $C_{4+}$ isoparaffins in the presence of an alkylation catalyst at an alkylation temperature and alkylation pressure to produce a product stream comprising $C_{6+}$ paraffins.

In one embodiment, the hydrogen comprises in situ generated APR hydrogen, external hydrogen, recycled hydrogen, or combinations of any two or more of the foregoing. In one version, at least a portion of the hydrogen is an APR hydrogen produced by a method comprising catalytically reacting a first portion of the water and oxygenated hydrocarbon in the presence of an aqueous phase reforming catalyst (APR catalyst) at a reforming temperature and reforming pressure to produce the APR hydrogen. In another version, the step of catalytically reacting the oxygenated hydrocarbon with hydrogen in the presence of a deoxygenation catalyst is conducted in the presence of an insignificantly effective amount of external hydrogen. In yet another version, the molar ratio of the total oxygen atoms in the oxygenated hydrocarbons to the total hydrogen atoms in the supplemental hydrogen is less than 1:1.

One aspect of the invention is that conventional liquid fuels and chemicals can be produced from oxygenated hydrocarbons derived from biomass. The oxygenated hydrocarbons may be any water-soluble oxygenated hydrocarbon having two or more carbon atoms and at least two one oxygen atoms ($C_{2+}O_{2+}C_{2+}O_{1+}$ hydrocarbons). In one version, the $C_{2+}O_{2+}C_{2+}O_{1+}$ hydrocarbons comprise a member selected from the group consisting of a sugar alcohol, sugar, monosaccharides, disaccharides, polysaccharides, cellulose derivatives, lignin derivatives, hemicelluloses derivatives, or a mixture of any two or more of the foregoing. In another version, the oxygenated hydrocarbons comprise a $C_{2-12}O_{1-11}$ hydrocarbon, or a $C_{2-12}O_{1-6}$ hydrocarbon. In yet another version, the $C_{2+}O_{2+}C_{2+}O_{1+}$ hydrocarbon comprises a sugar, sugar alcohol, monosaccharides, disaccharides, alditol, cellulosic derivative, lignocellulosic derivative, glucose, fructose, sucrose, maltose, lactose, mannose, xylose, arabitol, erythritol, glycerol, isomalt, lactitol, malitol, mannitol, sorbitol, xylitol, or a mixture of any two or more of the foregoing. In another embodiment, the oxygenated hydrocarbon further comprises recycled $C_{2+}O_{2+}C_{2+}O_{1+}$ hydrocarbons.

The oxygenates may be any hydrocarbon having 2 or more carbon atoms and 1 to 3 oxygen atoms (referred to herein as $C_{2+}O_{1-3}$ hydrocarbons). In one embodiment, the oxygenate comprises an alcohol, ketone, aldehyde, furan, diol, triol, hydroxy carboxylic acid, carboxylic acid, or a mixture of any two or more of the foregoing. In another embodiment, the oxygenate comprises ethanol, n-propyl alcohol, isopropyl alcohol, butyl alcohol, pentanol, hexanol, cyclopentanol, cyclohexanol, 2-methylcyclopentanol, hydroxyketones, cyclic ketones, acetone, propanone, butanone, pentanone, hexanone, 2-methyl-cyclopentanone, ethylene glycol, 1,3-propanediol, propylene glycol, butanediol, pentanediol, hexanediol, methylglyoxal, butanedione, pentanedione, diketohexane, hydroxyaldehydes, acetaldehyde, propionaldehyde, butyraldehyde, pentanal, hexanal, formic acid, acetic acid, propionic acid, butanoic acid, pentanoic acid, hexanoic acid, lactic acid, glycerol, furan, tetrahydrofuran, dihydrofuran, 2-furan methanol, 2-methyl-tetrahydrofuran, 2,5-dimethyl-tetrahydrofuran, 2-ethyl-tetrahydrofuran, 2-methyl furan, 2-ethyl furan, 2,5-dimethyl furan, 3-hydroxytetrahydrofuran, tetrahydro-3-furanol, hydroxylmethylfurfural, tetrahydro-2-furoic acid, 5-hydroxymethyl-2(5H)-furanone, dihydro-5-(hydroxymethyl)-2(3H)-furanone, 1-(2-furyl)ethanol, dihydro-5-(hydroxymethyl)-2(3H)-furanone, hydroxymethyltetrahydrofurfural, and tetrahydrofurfuryl alcohol, isomers thereof, or combinations of any two or more of the foregoing. In yet another embodiment, the oxygenate further comprises recycled $C_{2+}O_{1-3}$ hydrocarbons.

The $C_{2+}O_{1-3}$ hydrocarbon are produced by catalytically reacting hydrogen, water, and the water soluble oxygenated hydrocarbons in the presence of a deoxygenation catalyst and at a deoxygenation temperature and deoxygenation pressure. The reaction may be performed in either a liquid phase, vapor phase, or a combination of the foregoing. The deoxygenation catalyst is a heterogeneous catalyst having one or more materials capable of catalyzing a reaction between hydrogen and the oxygenated hydrocarbon to remove one or more of the oxygen atoms from the oxygenated hydrocarbon to produce alcohols, ketones, aldehydes, furans, carboxylic acids, hydroxy carboxylic acids, diols and triols. In one version, the deoxygenation catalyst comprises a support and Re, Cu, Fe, Ru, Ir, Co, Rh, Pt, Pd, Ni, W, Os, Mo, Ag, Au, an alloy of any two or more of the foregoing, or a combination of any two or more of the foregoing. In another version, the deoxygenation catalyst further comprises Mn, Cr, Mo, W, V, Nb, Ta, Ti, Zr, Y, La, Sc, Zn, Cd, Ag, Au, Sn, Ge, P, Al, Ga, In, Tl, or a combination of any two or more of the foregoing. In one embodiment, the support comprises a nitride, carbon, silica, alumina, zirconia, titania, vanadia, ceria, boron nitride, heteropolyacid, kieselguhr, hydroxyapatite, zinc oxide, chromia, or a mixture of any two or more of the foregoing. In another embodiment, the support is a hydrogen peroxide treated carbon. In another embodiment, the support is modified by treating the support with a modifier being silanes, alkali compounds, alkali earth compounds, or lanthanides. In yet another embodiment, the support comprises carbon nanotubes, carbon fullerenes, and zeolites.

The deoxygenation reaction is conducted at a temperature where the thermodynamics are favorable. In one embodiment, the deoxygenation temperature is in the range of about 100° C. to 600° C., and the deoxygenation pressure is at least 0.1 atmosphere. In another embodiment, the deoxygenation temperature is in the range of about 80° C. to about 300° C., and the deoxygenation pressure is a pressure where the water and the oxygenated hydrocarbon are liquid. In yet another embodiment, the deoxygenation temperature is in the range of about 200° C. to about 280° C., and the deoxygenation pressure is a pressure where the water and oxygenated hydrocarbon are liquid.

In another embodiment, the deoxygenation temperature is in the range of about 100° C. to 600° C., and the deoxygenation pressure is a pressure where the water and the oxygenated hydrocarbon are gaseous. In one version, the deoxygenation temperature is in the range of about 200° C. to 280° C., and the deoxygenation pressure is a pressure where the water and the oxygenated hydrocarbon are gaseous. In another version, the deoxygenation temperature is in the range of about 100° C. to 450° C., and the deoxygenation pressure is in the range of about 72 psig to 1300 psig. In yet another version, the deoxygenation temperature is in the range of about 120° C. to 300° C., and the deoxygenation pressure is in the range of about 72 psig to 1200 psig. In still yet another version, the deoxygenation temperature is in the range of about 200° C. to 280° C., and the deoxygenation pressure is in the range of about 200 psig to 725 psig.

Another aspect of the present invention is that the hydrogen used in the system may be generated in situ by catalytically reacting a portion of the water and oxygenated hydrocarbon in the presence of an aqueous phase reforming catalyst (APR catalyst) at a reforming temperature and reforming pressure to produce the in situ generated APR hydrogen. The reaction may be performed in the vapor phase, liquid phase, or a combination of both. The APR catalyst is preferably a heterogeneous catalyst capable of catalyzing the reaction of water and oxygenated hydrocarbons to form an APR hydrogen stream comprising APR hydrogen, CO, $CO_2$ and water. In one embodiment, the aqueous phase reforming catalyst comprises a support and Fe, Ru, Os, Ir, Co, Rh, Pt, Pd, Ni, an alloy of any two or more of the foregoing, or a combination of any two or more of the foregoing. In another embodiment, the aqueous phase reforming catalyst further comprises Cu, B, Mn, Re, Cr, Mo, Bi, W, V, Nb, Ta, Ti, Zr, Y, La, Sc, Zn, Cd, Ag, Au, Sn, Ge, P, Al, Ga, In, Tl, an alloy of any two or more of the foregoing, or a combination of any two or more of the foregoing. The support generally comprises any one of the above supports described for the deoxygenation catalyst. In certain embodiments, one or more of the APR catalyst, deoxygenation catalyst, and alkylation catalyst are atomically identical.

In another embodiment, the APR catalyst and deoxygenation catalyst comprise Pt alloyed or admixed with Ni, Ru, Cu, Fe, Rh, Re, alloys of any two or more of the foregoing, or a combination of any two or more of the foregoing. In one version, the APR catalyst and deoxygenation catalyst comprise Ru alloyed or admixed with Ge, Bi, B, Ni, Sn, Cu, Fe, Rh, Pt, alloys of any two or more of the foregoing, or a combination of any two or more of the foregoing. In another version, the APR catalyst comprises Ni alloyed or admixed with Sn, Ge, Bi, B, Cu, Re, Ru, Fe, alloys of any two or more of the foregoing, or a combination of any two or more of the foregoing.

The APR reaction is conducted at a temperature where the thermodynamics are favorable. In one embodiment, the reforming temperature is in the range of about 100° C. to about 450° C., and the reforming pressure is a pressure where the water and the oxygenated hydrocarbon are gaseous. In another embodiment, the reforming temperature is in the range of about 100° C. to about 300° C., and the reforming pressure is a pressure where the water and the oxygenated hydrocarbon are gaseous. In yet another embodiment, the reforming temperature is in the range of about 80° C. to 400° C., and the reforming pressure is a pressure where the water and the oxygenated hydrocarbon are liquids.

In another embodiment, the APR reaction and the deoxygenation reaction are performed in the same reactor. In one version, the reforming temperature and deoxygenation temperature is in the range of about 100° C. to 450° C., and the reforming pressure and deoxygenation pressure is in the range of about 72 psig to 1300 psig. In yet another version, the reforming temperature and deoxygenation temperature is in the range of about 120° C. to 300° C., and the reforming pressure and deoxygenation pressure is in the range of about 72 psig to 1200 psig. In still yet another version, the reforming temperature and deoxygenation temperature is in the range of about 200° C. to 280° C., and the reforming pressure and deoxygenation pressure is in the range of about 200 psig to 725 psig.

The $C_{2+}$ olefins are produced by catalytically reacting the $C_{2+}O_{1-3}$ hydrocarbons in the presence of a dehydration catalyst at a dehydration temperature and dehydration pressure to produce a reaction stream comprising the $C_{2+}$ olefins. The $C_{2+}$ olefins comprise straight or branched hydrocarbons containing one or more carbon-carbon double bonds. In general, the $C_{2+}$ olefins contain from 2 to 8 carbon atoms, and more preferably from 3 to 5 carbon atoms. In one embodiment, the olefins comprise propylene, butylene, pentylene, isomers of the foregoing, and mixtures of any two or more of the foregoing. In another embodiment, the $C_{2+}$ olefins include $C_{4+}$ olefins produced by catalytically reacting a portion of the $C_{2+}$ olefins over an olefin isomerization catalyst.

The dehydration catalyst comprises a member selected from the group consisting of an acidic alumina, aluminum phosphate, silica-alumina phosphate, amorphous silica-alumina, aluminosilicate, zirconia, sulfated zirconia, tungstated zirconia, tungsten carbide, molybdenum carbide, titania, sulfated carbon, phosphated carbon, phosphated silica, phosphated alumina, acidic resin, heteropolyacid, inorganic acid, and a combination of any two or more of the foregoing. In one embodiment, the dehydration catalyst further comprises a modifier selected from the group consisting of Ce, Y, Sc, La, Li, Na, K, Rb, Cs, Mg, Ca, Sr, Ba, P, B, Bi, and a combination of any two or more of the foregoing. In another embodiment, the dehydration catalyst further comprises an oxide of an element, the element selected from the group consisting of Ti, Zr, V, Nb, Ta, Mo, Cr, W, Mn, Re, Al, Ga, In, Fe, Co, Ir, Ni, Si, Cu, Zn, Sn, Cd, P, and a combination of any two or more of the foregoing. In yet another embodiment, the dehydration catalyst further comprises a metal selected from the group consisting of Cu, Ag, Au, Pt, Ni, Fe, Co, Ru, Zn, Cd, Ga, In, Rh, Pd, Ir, Re, Mn, Cr, Mo, W, Sn, Os, an alloy of any two or more of the foregoing, and a combination of any two or more of the foregoing.

In another embodiment, the dehydration catalyst comprises an aluminosilicate zeolite. In one version, the dehydration catalyst further comprises a modifier selected from the group consisting of Ga, In, Zn, Fe, Mo, Ag, Au, Ni, P, Sc, Y, Ta, a lanthanide, and a combination of any two or more of the foregoing. In another version, the dehydration catalyst further comprises a metal selected from the group consisting of Cu, Ag, Au, Pt, Ni, Fe, Co, Ru, Zn, Cd, Ga, In, Rh, Pd, Ir, Re, Mn, Cr, Mo, W, Sn, Os, an alloy of any two or more of the foregoing, and a combination of any two or more of the foregoing.

In another embodiment, the dehydration catalyst comprises a bifunctional pentasil ring-containing aluminosilicate zeolite. In one version, the dehydration catalyst further comprises a modifier selected from the group consisting of Ga, In, Zn, Fe, Mo, Ag, Au, Ni, P, Sc, Y, Ta, a lanthanide, and a combination of any two or more of the foregoing. In another version, the dehydration catalyst further comprises a metal selected from the group consisting of Cu, Ag, Au, Pt, Ni, Fe, Co, Ru, Zn, Cd, Ga, In, Rh, Pd, Ir, Re, Mn, Cr, Mo, W, Sn, Os, an alloy of any two or more of the foregoing, and a combination of any two or more of the foregoing.

The dehydration reaction is conducted at a temperature and pressure where the thermodynamics are favorable. In general, the reaction may be performed in the vapor phase, liquid phase, or a combination of both. In one embodiment, the dehydration temperature is in the range of about 100° C. to 500° C., and the dehydration pressure is in the range of about 0 psig to 900 psig. In another embodiment, the dehydration temperature is in the range of about 125° C. to 450° C., and the dehydration pressure is at least 2 psig. In another version, the dehydration temperature is in the range of about 150° C. to 350° C., and the dehydration pressure is in the range of about 100 psig to 800 psig. In yet another version, the dehydration temperature is in the range of about 175° C. to 325° C.

The $C_{6+}$ paraffins are produced by catalytically reacting the $C_{2+}$ olefins with a stream of $C_{4+}$ isoparaffins in the presence of an alkylation catalyst at an alkylation temperature and alkylation pressure to produce a product stream comprising $C_{6+}$ paraffins. The $C_{4+}$ isoparaffins include alkanes and cycloalkanes having 4 to 7 carbon atoms, such as isobutane, isopentane, naphthenes, and higher homologues having a tertiary carbon atom (e.g., 2-methylbutane and 2,4-dimethylpentane), isomers of the foregoing, and mixtures of any two or more of the foregoing. In one embodiment, the stream of $C_{4+}$ isoparaffins comprises of internally generated $C_{4+}$ isoparaffins, external $C_{4+}$ isoparaffins, recycled $C_{4+}$ isoparaffins, or combinations of any two or more of the foregoing.

The $C_{6+}$ paraffins will generally be branched paraffins, but may also include normal paraffins. In one version, the $C_{6+}$ paraffins comprises a member selected from the group consisting of a branched $C_{6-10}$ alkane, a branched $C_6$ alkane, a branched $C_7$ alkane, a branched $C_8$ alkane, a branched $C_9$ alkane, a branched $C_{10}$ alkane, or a mixture of any two or more of the foregoing. In one version, the $C_{6+}$ paraffins comprise dimethylbutane, 2,2-dimethylbutane, 2,3-dimethylbutane, methylpentane, 2-methylpentane, 3-methylpentane, dimethylpentane, 2,3-dimethylpentane, 2,4-dimethylpentane, methylhexane, 2,3-dimethylhexane, 2,3,4-trimethylpentane, 2,2,4-trimethylpentane, 2,2,3-trimethylpentane, 2,3,3-trimethylpentane, dimethylhexane, or mixtures of any two or more of the foregoing.

The alkylation catalyst comprises a member selected from the group of sulfuric acid, hydrofluoric acid, aluminum chloride, boron trifluoride, solid phosphoric acid, chlorided alumina, acidic alumina, aluminum phosphate, silica-alumina phosphate, amorphous silica-alumina, aluminosilicate, aluminosilicate zeolite, zirconia, sulfated zirconia, tungstated zirconia, tungsten carbide, molybdenum carbide, titania, sulfated carbon, phosphated carbon, phosphated silica, phosphated alumina, acidic resin, heteropolyacid, inorganic acid, and a combination of any two or more of the foregoing. The alkylation catalyst may also include a mixture of a mineral acid with a Friedel-Crafts metal halide, such as aluminum bromide, and other proton donors.

In one embodiment, the alkylation catalyst comprises an aluminosilicate zeolite. In one version, the alkylation catalyst further comprises a modifier selected from the group consisting of Ga, In, Zn, Fe, Mo, Ag, Au, Ni, P, Sc, Y, Ta, a lanthanide, and a combination of any two or more of the foregoing. In another version, the alkylation catalyst further comprises a metal selected from the group consisting of Cu, Ag, Au, Pt, Ni, Fe, Co, Ru, Zn, Cd, Ga, In, Rh, Pd, Ir, Re, Mn, Cr, Mo, W, Sn, Os, an alloy of any two or more of the foregoing, and a combination of any two or more of the foregoing.

In another embodiment, the alkylation catalyst comprises a bifunctional pentasil ring-containing aluminosilicate zeolite. In one version, the alkylation catalyst further comprises a modifier selected from the group consisting of Ga, In, Zn, Fe, Mo, Ag, Au, Ni, P, Sc, Y, Ta, a lanthanide, and a combination of any two or more of the foregoing. In another version, the alkylation catalyst further comprises a metal selected from the group consisting of Cu, Ag, Au, Pt, Ni, Fe, Co, Ru, Zn, Cd, Ga, In, Rh, Pd, Ir, Re, Mn, Cr, Mo, W, Sn, Os, an alloy of any two or more of the foregoing, and a combination of any two or more of the foregoing. In one version, the dehydration catalyst and the alkylation catalyst are atomically identical.

The alkylation reaction is conducted at a temperature where the thermodynamics are favorable. In general, the alkylation temperature is in the range of about -20° C. to 300° C., and the alkylation pressure is in the range of about 0 psig to 1200 psig. In one version, the alkylation temperature is in the range of about 100° C. to 300° C. In another version, the alkylation temperature is in the range of about 0° C. to 100° C., and the alkylation pressure is at least 100 psig. In yet another version, the alkylation temperature is in the range of about 0° C. to 50° C. and the alkylation pressure is less than 300 psig. In still yet another version, the alkylation temperature is in the range of about 70° C. to 250° C., and the alkylation pressure is in the range of about 100 psig to 1200 psig. In one embodiment, the alkylation catalyst comprises a mineral acid or a strong acid and the alkylation temperature is less than 80° C. In another embodiment, the alkylation catalyst comprises a zeolite and the alkylation temperature is greater than 100° C.

Another aspect of the present invention is that the $C_{4+}$ isoparaffins may be generated internally by catalytically reacting an isoparaffin feedstock stream comprising $C_{4+}$ normal paraffins, aromatics and/or naphthenes in the presence of an isomerization catalyst at an isomerization temperature and isomerization pressure to produce internally generated $C_{4+}$ isoparaffins. The $C_{4+}$ normal paraffins will generally include alkanes having 4 to 7 carbon atoms, such as n-butane, n-pentane, n-hexane, n-heptane, and mixtures of any two or more of the foregoing. In one arrangement, the isoparaffin feedstock stream is collected upstream of the alkylation catalyst from the reaction stream having the $C_{2+}O_{1-3}$ hydrocarbons (oxygenates) or the reaction stream having the $C_{2+}$ olefins and processed for the production of the internally generated $C_{4+}$ isoparaffins. In another arrangement, the $C_{4+}$ normal paraffins, aromatics and/or Naphthenes are collected downstream of the alkylation catalyst from the product stream having the $C_{6+}$ paraffins and then recycled for use in the production of the internally generated $C_{4+}$ isoparaffins. The $C_{4+}$ isoparaffins may also be provided solely from an external source or used to supplement the internally generated $C_{4+}$ isoparaffins. In another version, the $C_{4+}$ isoparaffins are recycled $C_{4+}$ isoparaffins collected from the product stream having the $C_{6+}$ paraffins.

The isomerization catalyst is a catalyst capable of reacting a $C_{4+}$ normal paraffin, aromatic or naphthene to produce a $C_{4+}$ isoparaffin. In one version, the isomerization catalyst includes a zeolite, zirconia, sulfated zirconia, tungstated zirconia, alumina, silica-alumina, zinc aluminate, chlorided alumina, phosphoric acid, or mixtures of any two or more of the foregoing. In another version, the isomerization catalyst is an acidic beta, mordenite, or ZSM-5 zeolite. In yet another version, the isomerization catalyst further comprises a metal selected from the group consisting of Y, Pt, Ru, Ad, Ni, Rh, Ir, Fe, Co, Os, Zn, a lanthanide, or an alloy or combination of any two or more of the foregoing. In still yet another version, the isomerization catalyst comprises a support, the support comprising alumina, sulfated oxide, clay, silica gel, aluminum phosphate, bentonite, kaolin, magnesium silicate, magnesium carbonate, magnesium oxide, aluminum oxide, activated alumina, bauxite, silica, silica-alumina, activated carbon, pumice, zirconia, titania, zirconium, titanium, kieselguhr, or zeolites.

In one embodiment, the isomerization catalyst comprises a support of a sulfated oxide or hydroxide of a Group IVB metal, at least one Group IIIA compound, and a Group VIII metal. In one version, the Group IVB metal comprises, zirconium, titanium, or mixtures of the foregoing, and the Group IIIA compound comprises gallium, indium, or mixtures of the foregoing. In another version, the Group VIII metal comprises Pd, Pt, Ru, Rh, Ir, Os, alloys of any two or more of the foregoing, or mixtures of any two or more of the foregoing. In yet another version, the paraffin isomerization catalyst further includes Fe, Co, Ni, Re, Y, Eu, Tm, Ho, Er, Yb, Tb, or alloys or mixtures of any two or more of the foregoing. In general, the $C_{4+}$ normal paraffins comprise alkanes having 4 to 7 carbon atoms, such as n-butane, n-pentane, n-hexane, n-heptane, and mixtures of any two or more of the foregoing. The aromatics comprise benzene, toluene, xylene, isomers of the foregoing, and mixtures of any two or more of the foregoing.

The isomerization reaction is conducted at a temperature where the thermodynamics are favorable. In one version, the isomerization temperature is in the range of about 100° C. to 250° C., and the isomerization pressure is in the range of about 100 psig to 800 psig. In another version, the isomerization temperature is in the range of about 125° C. to 225° C., and the isomerization pressure is in the range of about 100 psig to 1200 psig. In yet another version, the isomerization temperature is in the range of about 200° C. to 350° C., and the isomerization pressure is in the range of about 100 psig to 1200 psig.

The isomerization reaction should also be conducted at a temperature and pressure in view of the isomerization catalyst employed. In one embodiment, the isomerization catalyst comprises chlorided alumina and the isomerization temperature is in the range of about 100° C. to 250° C., and the isomerization pressure is in the range of about 100 psig to 800 psig. In another embodiment, the isomerization catalyst comprises a sulfated zirconia or a tungstated zirconia, and the isomerization temperature is in the range of about 125° C. to 225° C., and the isomerization pressure is in the range of about 100 psig to 1200 psig. In another embodiment, the isomerization catalyst comprises a zeolite, and the isomerization temperature is in the range of about 200° C. to 350° C., and the isomerization pressure is in the range of about 100 psig to 1200 psig.

In another embodiment of the present invention, the method further comprises the step or act of catalytically reacting a polysaccharide, disaccharide, monosaccharide, polyhydric alcohol, sugar, sugar alcohol or a combination of any two or more of the foregoing with hydrogen in the presence of a hydrogenolysis catalyst at a hydrogenolysis temperature and hydrogenolysis pressure to produce the water soluble oxygenated hydrocarbon. In one version, the hydrogenolysis temperature is at least 110° C. and the hydrogenolysis pressure is in the range of about 10 psig to 2400 psig. in another version, the hydrogenolysis temperature is in the range of about 110° C. to 300° C. The hydrogenolysis catalyst generally comprises phosphate, Cr, Mo, W, Re, Mn, Cu, Cd, Fe, Ru, Os, Ir, Co, Rh, Pt, Pd, Ni, alloys of any two or more of the foregoing, or a combination of any two or more of the foregoing. In one version, the hydrogenolysis catalyst further comprises Au, Ag, Zn, Sn, Bi, B, Cr, Mn, O, alloys of any two or more of the foregoing, or a combination of any two or more of the foregoing. In another version, the hydrogenolysis catalyst further comprises an alkaline earth metal oxide. In yet another version, the hydrogenolysis catalyst further comprises any one of the above supports. In one embodiment, the hydrogen comprises in situ generated APR hydrogen, external hydrogen, recycled hydrogen, or a combination of any two or more of the foregoing.

In another embodiment of the present invention, the method further comprises the step or act of catalytically reacting an oxygenated hydrocarbon comprising a polysaccharide, disaccharide, monosaccharide, sugar, furfural, carboxylic acid, ketone, or furan, with hydrogen in the presence of a hydrogenation catalyst at a hydrogenation temperature and hydrogenation pressure to produce the water soluble oxygenated hydrocarbon. In one version, the hydrogenation temperature is in the range of about 80° C. to 250° C., and the hydrogenation pressure is in the range of about 100 psig to 2000 psig. The hydrogenation catalyst generally comprises a support and Fe, Ru, Os, Ir, Co, Rh, Pt, Pd, Ni, Re, Cu, alloys of any two or more of the foregoing, or a combination of any two or more of the foregoing. In one version, the hydrogenation catalyst further comprises Ag, Au, Cr, Zn, Mn, Sn, Bi, Mo, W, B, P, alloys of any two or more of the foregoing, or a combination of any two or more of the foregoing. In another version, the support comprises any one of the above supports. In one embodiment, the hydrogen comprises in situ generated APR hydrogen, external hydrogen, recycled hydrogen, or a combination of any two or more of the foregoing.

In another embodiment, the method further comprises the step or act of catalytically reacting the $C_{2+}O_{1-3}$ hydrocarbon in the presence of a hydrogenation catalyst prior to the step of reacting the $C_{2+}O_{1-3}$ hydrocarbons in the presence of the dehydration catalyst. In such event, the $C_{2+}O_{1-3}$ hydrocarbons are reacted in the presence of the hydrogenation catalyst at a hydrogenation temperature and hydrogenation pressure to produce oxygenated hydrocarbons comprising a $C_{2+}O_{1-3}$ hydroxyl compound. In one version, the hydrogenation temperature is in the range of about 80° C. to 250° C., and the hydrogenation pressure is in the range of about 100 psig to 2000 psig. The hydrogenation catalyst generally comprises a support and Fe, Ru, Os, Ir, Co, Rh, Pt, Pd, Ni, Re, Cu, alloys of any two or more of the foregoing, or a combination of any two or more of the foregoing. In one version, the hydrogenation catalyst further comprises Ag, Au, Cr, Zn, Mn, Sn, Bi, Mo, W, B, P, alloys of any two or more of the foregoing, or a combination of any two or more of the foregoing. In another version, the support comprises any one of the above supports. In one embodiment, the hydrogen comprises in situ generated APR hydrogen, external hydrogen, recycled hydrogen, or a combination of any two or more of the foregoing.

Another aspect of the invention is a method of making a $C_{6+}$ branched hydrocarbon involving the steps or acts of: (1) providing water and a water soluble oxygenated hydrocarbon comprising a $C_{2+}O_{1-3}$ hydrocarbon and catalytically reacting a first portion of the water and water soluble oxygenated hydrocarbon in the liquid phase and/or vapor phase in the presence of an APR catalyst at a reforming temperature and a reforming pressure to produce an APR stream comprising APR hydrogen, CO, $CO_2$ and water; (2) catalytically reacting a second portion of the water soluble oxygenated hydrocarbon with the in situ generated APR hydrogen in the presence of a deoxygenation catalyst at a deoxygenation temperature and deoxygenation pressure to produce an oxygenate comprising a $C_{2+}O_{1-3}$ hydrocarbon; (3) catalytically reacting a portion of the $C_{2+}O_{1-3}$ hydrocarbons in the presence of a dehydration catalyst at a dehydration temperature and dehydration pressure to produce $C_{2+}$ olefins, and (4) catalytically reacting the $C_{2+}$ olefins with a stream of $C_{4+}$ isoparaffins in the presence of an alkylation catalyst at an alkylation temperature and alkylation pressure to produce a product stream comprising $C_{6+}$ paraffins. In one embodiment, the method further comprises the steps or acts of providing supplemental hydrogen, and catalytically reacting a portion of the water soluble oxygenated hydrocarbon with supplemental hydrogen in the presence of the deoxygenation catalyst to produce the oxygenate. In one version, the $C_{4+}$ isoparaffins comprise internally generated $C_{4+}$ isoparaffins, external $C_{4+}$ isoparaffins, recycled $C_{4+}$ isoparaffins, or a combination of any two or more of the foregoing. In another version, one or more of the deoxygenation catalyst, APR catalyst, dehydration catalyst and alkylation catalyst are atomically identical.

Another aspect of the invention is a method of making a $C_{6+}$ paraffin comprising the steps or acts of: (1) providing an aqueous solution comprising water and a member selected from the group consisting of a polysaccharide, disaccharide, monosaccharide, sugar, furfural, carboxylic acid, ketone, furan, and a combination of any two or more of the foregoing, and catalytically reacting the polysaccharide, disaccharide, monosaccharide, sugar, furfural, carboxylic acid, ketone, furan, or combination of any two or more of the foregoing, with hydrogen in the presence of a hydrogenation catalyst at a hydrogenation temperature and hydrogenation pressure to produce a water soluble oxygenated hydrocarbon comprising a $C_{1+}O_{1+}$ hydrocarbon; (2) catalytically reacting a first portion of the water and oxygenated hydrocarbon in the presence of an APR catalyst at a reforming temperature and a reforming pressure to produce an APR stream comprising APR hydrogen, CO, $CO_2$ and water; (3) catalytically reacting a second portion of the oxygenated hydrocarbon with the APR hydrogen in the presence of a deoxygenation catalyst at a deoxygenation temperature and deoxygenation pressure to produce an oxygenate comprising a $C_{2+}O_{1-3}$ hydrocarbon; (4) catalytically reacting a portion of the oxygenate in the presence of a dehydration catalyst at a dehydration temperature and dehydration pressure to produce $C_{2+}$ olefins; and (5) catalytically reacting the $C_{2+}$ olefins with a stream of $C_{4+}$ isoparaffins in the presence of an alkylation catalyst at an alkylation temperature and alkylation pressure to produce a product stream comprising $C_{6+}$ paraffins. In one version, the method further comprises the steps or acts of providing APR hydrogen or supplemental hydrogen comprising external hydrogen, recycled hydrogen, or a combination of any two or more of the foregoing, and reacting the supplemental hydrogen with the polysaccharide, disaccharide, monosaccharide, sugar, furfural, carboxylic acid, ketone, furan, and a combination of any two or more of the foregoing, and/or with the $C_{2+}O_{1-3}$ oxygenated hydrocarbon. In another version, the $C_{4+}$ isoparaffins comprise internally generated $C_{4+}$ isoparaffins, external $C_{4+}$ isoparaffins, recycled $C_{4+}$ isoparaffins, or a combination of any two or more of the foregoing.

Another aspect of the invention is a method of making a $C_{6+}$ paraffin comprising the steps or acts of: (1) providing an aqueous solution comprising water and a polysaccharide, disaccharide, monosaccharide, polyhydric alcohol, sugar, sugar alcohol, or a combination of any two or more of the foregoing, and catalytically reacting the sugar, sugar alcohol, polysaccharide, disaccharide, monosaccharide, polyhydric alcohol, or combination, with hydrogen in the presence of a hydrogenolysis catalyst at a hydrogenolysis temperature and hydrogenolysis pressure to produce an oxygenated hydrocarbon comprising a $C_{1-4}O_{1-4}$ hydrocarbon; (2) catalytically reacting a portion of the water and oxygenated hydrocarbon in the presence of an aqueous phase reforming catalyst at a reforming temperature and a reforming pressure to produce an APR stream comprising APR hydrogen, CO, $CO_2$ and water; (3) catalytically reacting the oxygenated hydrocarbon with the APR hydrogen in the presence of a deoxygenation catalyst at a deoxygenation temperature and deoxygenation pressure to produce an oxygenate comprising a $C_{2+}O_{1-3}$ hydrocarbon; (4) catalytically reacting a portion of the oxygenate in the presence of a dehydration catalyst at a dehydration temperature and dehydration pressure to produce $C_{2+}$ olefins; (5) and catalytically reacting the $C_{2+}$ olefins with a stream of $C_{4+}$ isoparaffins in the presence of an alkylation catalyst at an alkylation temperature and alkylation pressure to produce a product stream comprising $C_{6+}$ paraffins. In one version, the method further comprises the steps or acts of providing APR hydrogen or supplemental hydrogen comprising external hydrogen, recycled hydrogen or a combination of the foregoing, and reacting the APR hydrogen or supplemental hydrogen with the polysaccharide, disaccharide, monosaccharide, polyhydric alcohol, sugar, sugar alcohol, or combination of any two or more of the foregoing and/or with the $C_{1+}O_{1-3}$ oxygenated hydrocarbon. In another version, the $C_{4+}$ isoparaffins comprise internally generated $C_{4+}$ isoparaffins, external $C_{4+}$ isoparaffins, recycled $C_{4+}$ isoparaffins, or a combination of any two or more of the foregoing.

Another aspect of the invention is a method of making a $C_{6+}$ paraffin comprising the steps or acts of: (1) providing an aqueous solution comprising water and a water soluble oxygenated hydrocarbon selected from the group consisting of a polysaccharide, disaccharide, monosaccharide, sugar, furfural, carboxylic acid, ketone, furan, and a combination of any two or more of the foregoing, and catalytically reacting the polysaccharide, disaccharide, monosaccharide, sugar, furfural, carboxylic acid, ketone, furan, or combination of any two or more of the foregoing, with hydrogen in the presence of a first hydrogenation catalyst at a first hydrogenation temperature and first hydrogenation pressure to produce a water soluble oxygenated hydrocarbon comprising a $C_{1+}O_{1+}$ hydrocarbon; (2) catalytically reacting a first portion of the water and water soluble oxygenated hydrocarbon in the presence of an APR catalyst at a reforming temperature and a reforming pressure to produce an APR stream comprising hydrogen, CO, $CO_2$ and water; (3) catalytically reacting a second portion of the water and the water soluble oxygenated hydrocarbon with the APR hydrogen in the presence of a deoxygenation catalyst at a deoxygenation temperature and deoxygenation pressure to produce an oxygenate comprising a $C_{2+}O_{1-3}$ hydrocarbon; (4) catalytically reacting a portion of the $C_{2+}O_{1-3}$ hydrocarbons with hydrogen in the presence of a second hydrogenation catalyst at a hydrogenation temperature and hydrogenation pressure to produce a $C_{2+}$ hydroxyl compound; (5) catalytically reacting a portion of the $C_{2+}$ hydroxyl compound in the presence of a dehydration catalyst at a dehydration temperature and dehydration pressure to produce $C_{2+}$ olefins; and (6) catalytically reacting the $C_{2+}$ olefins with a stream of $C_{4+}$ isoparaffins in the presence of an alkylation catalyst at an alkylation temperature and alkylation pressure to produce a product stream comprising $C_{6+}$ paraffins. In one version, the method further comprises the steps or acts of providing APR hydrogen or supplemental hydrogen comprising external hydrogen, recycled hydrogen or a combination of the foregoing, and reacting the APR hydrogen or supplemental hydrogen with the sugar, furfural, carboxylic acid, ketone, furan, and a combination of any two or more of the foregoing, and/or with the $C_2O_{1-3}$ oxygenated hydrocarbon. In another version, the $C_{4+}$ isoparaffins comprise in situ generated $C_{4+}$ isoparaffins, external $C_{4+}$ isoparaffins, recycled $C_{4+}$ isoparaffins, or a combination of any two or more of the foregoing.

Another aspect of the invention is a method of making a $C_{6+}$ paraffin comprising the steps or acts of: (1) catalytically reacting a hydrogen, water and water soluble oxygenated hydrocarbons in the presence of a deoxygenation catalyst at a deoxygenation temperature and deoxygenation pressure to produce an oxygenate reaction stream comprising a $C_{2+}O_{1-3}$ hydrocarbon and one or more $C_{4+}$ normal paraffins, aromatics or naphthenes; (2) collecting a portion of the $C_{4+}$ normal paraffins, aromatics or naphthenes and catalytically reacting a portion of the $C_{4+}$ normal paraffins, aromatics or naphthenes in the presence of an isomerization catalyst to produce a stream of $C_{4+}$ isoparaffins; (3) catalytically reacting a portion of the $C_{2+}O_{1-3}$ hydrocarbons with hydrogen in the presence of a dehydration catalyst at a dehydration temperature and dehydration pressure to produce $C_{2+}$ olefins; and (4) catalytically reacting the $C_{2+}$ olefins with the $C_{4+}$ isoparaffins in the presence of an alkylation catalyst at an alkylation temperature and alkylation pressure to produce a product stream comprising $C_{6+}$ paraffins. In one version, at least a portion of the hydrogen is an APR hydrogen produced by a method comprising catalytically reacting a first portion of the water and oxygenated hydrocarbon in the presence of an APR catalyst at a reforming temperature and a reforming pressure to produce an APR stream comprising APR hydrogen, CO, $CO_2$ and water. In another version, the method further comprises the step of providing an aqueous solution comprising water and a polysaccharide, disaccharide, monosaccharide, polyhydric alcohol, sugar, sugar alcohol, furfural, carboxylic acid, ketone, furan, or a combination thereof, and catalytically reacting the polysaccharide, disaccharide, monosaccharide, polyhydric alcohol, sugar, sugar alcohol, furfural, carboxylic acid, ketone, furan, or combination, with hydrogen in the presence of a second hydrogenation catalyst at a hydrogenation temperature and hydrogenation pressure to produce the water soluble oxygenated hydrocarbon. In yet another version, the method further comprises the step of providing, an aqueous solution comprising water and a polysaccharide, disaccharide, monosaccharide, polyhydric alcohol, sugar, sugar alcohol, or a combination thereof, and catalytically reacting the sugar, sugar alcohol, polysaccharide, disaccharide, monosaccharide, polyhydric alcohol, or combination, with hydrogen in the presence of a hydrogenolysis catalyst at a hydrogenolysis temperature and hydrogenolysis pressure to produce the water soluble oxygenated hydrocarbon. In another version, the method further comprises the steps or acts of providing supplemental $C_{4+}$ isoparaffins comprising external $C_{4+}$ isoparaffins, recycled $C_{4+}$ isoparaffins, or a combination of any two or more of the foregoing, and reacting the supplemental $C_{4+}$ isoparaffins with the $C_{2+}$ olefins.

Another aspect of the invention is a method of making a $C_{6+}$ paraffin comprising the steps or acts of: (1) catalytically reacting a hydrogen, water and water soluble oxygenated hydrocarbons in the presence of a deoxygenation catalyst at a deoxygenation temperature and deoxygenation pressure to produce an oxygenate reaction stream comprising a $C_{2+}O_{1-3}$ hydrocarbon; (2) catalytically reacting a portion of the $C_{2+}O_{1-3}$ hydrocarbons with hydrogen in the presence of a dehydration catalyst at a dehydration temperature and dehydration pressure to produce $C_{2+}$ olefins and one or more $C_{4+}$ normal paraffins, aromatics or naphthenes; (2) collecting a portion of the $C_{4+}$ normal paraffins, aromatics or naphthenes and catalytically reacting a portion of the $C_{4+}$ normal paraffins, aromatics or naphthenes in the presence of an isomerization catalyst to produce a stream of $C_{4+}$ isoparaffins; and (4) catalytically reacting the $C_{2+}$ olefins with the $C_{4+}$ isoparaffins in the presence of an alkylation catalyst at an alkylation temperature and alkylation pressure to produce a product stream comprising $C_{6+}$ paraffins. In one version, at least a portion of the hydrogen is an APR hydrogen produced by a method comprising catalytically reacting a first portion of the water and oxygenated hydrocarbon in the presence of an APR catalyst at a reforming temperature and a reforming pressure to produce an APR stream comprising APR hydrogen, CO, $CO_2$ and water. In another version, the method further comprises the step of providing an aqueous solution comprising water and a polysaccharide, disaccharide, monosaccharide, polyhydric alcohol, sugar, sugar alcohol, furfural, carboxylic acid, ketone, furan, or a combination thereof, and catalytically reacting the polysaccharide, disaccharide, monosaccharide, polyhydric alcohol, sugar, sugar alcohol, furfural, carboxylic acid, ketone, furan, or combination, with hydrogen in the presence of a second hydrogenation catalyst at a hydrogenation temperature and hydrogenation pressure to produce the water soluble oxygenated hydrocarbon. In yet another version, the method further comprises the step of providing an aqueous solution comprising water and a polysaccharide, disaccharide, monosaccharide, polyhydric alcohol, sugar, sugar alcohol, or a combination thereof, and catalytically reacting the sugar, sugar alcohol, polysaccharide, disaccharide, monosaccharide, polyhydric alcohol, or combination, with hydrogen in the presence of a hydrogenolysis catalyst at a hydrogenolysis temperature and hydrogenolysis pressure to produce the water soluble oxygenated hydrocarbon. In another version, the method further comprises the steps or acts of providing supplemental $C_{4+}$ isoparaffins comprising external $C_{4+}$ isoparaffins, recycled $C_{4+}$ isoparaffins, or a combination of any two or more of the foregoing, and reacting the supplemental $C_{4+}$ isoparaffins with the $C_{2+}$ olefins.

In another aspect of the present invention, the method is performed in a reactor system comprising one or more reactor vessels, wherein the reactor system is adapted to be configured as continuous flow, batch, semi-batch, or a combination thereof. In one embodiment, the reactor system further comprises one or more of a fluidized catalytic bed, a swing bed, fixed bed, moving bed, liquid-liquid contacting reactor, or a combination of any two or more of the foregoing, wherein each bed is adapted to be housed within a reactor vessel. In another embodiment, the method is performed in the continuous flow reactor system at steady-state equilibrium.

In another embodiment, the reactor system further comprises a reforming bed adapted to contain the APR catalyst, a deoxygenation bed adapted to contain the deoxygenation catalyst, a dehydration bed adapted to contain the dehydration catalyst, and an alkylation bed adapted to contain the alkylation catalyst. In one version, the reforming bed and deoxygenation bed are oriented in a stacked, side-by-side or parallel configuration, and the reforming and deoxygenation beds are housed within a single reactor vessel. In another version, the reforming bed is housed within a reforming reactor vessel, and the deoxygenation bed is housed within a deoxygenation reactor vessel. In yet another version, the dehydration bed is housed within a dehydration reactor vessel and/or the alkylation bed is housed within an alkylation reactor vessel. In still yet another version, the single reactor vessel is further adapted to house the dehydration bed and/or alkylation bed.

In another embodiment, the reforming bed, deoxygenation bed, dehydration bed and alkylation bed are oriented in a stacked, side-by-side or parallel configuration within the single reactor vessel. In another embodiment, the continuous flow reactor system is oriented to provide horizontal, vertical or diagonal flow. In yet another embodiment, the deoxygenation bed is housed within a deoxygenation reactor vessel providing up-flow, and wherein the dehydration bed and alkylation, bed is housed within a reactor vessel providing down-flow. In still yet another embodiment, each catalytic reaction occurs at steady-state equilibrium.

DETAILED DESCRIPTION

The present invention relates to methods and reactor systems for producing paraffins from biomass-derived oxygenated hydrocarbons, such as sugars, sugar alcohols, cellulose derivatives, lignocellulose derivatives, hemicellulose derivatives, saccharides and the like. The paraffins produced are useful in fuel products, such as synthetic gasoline, diesel fuel and/or jet fuels.

Figure 1:
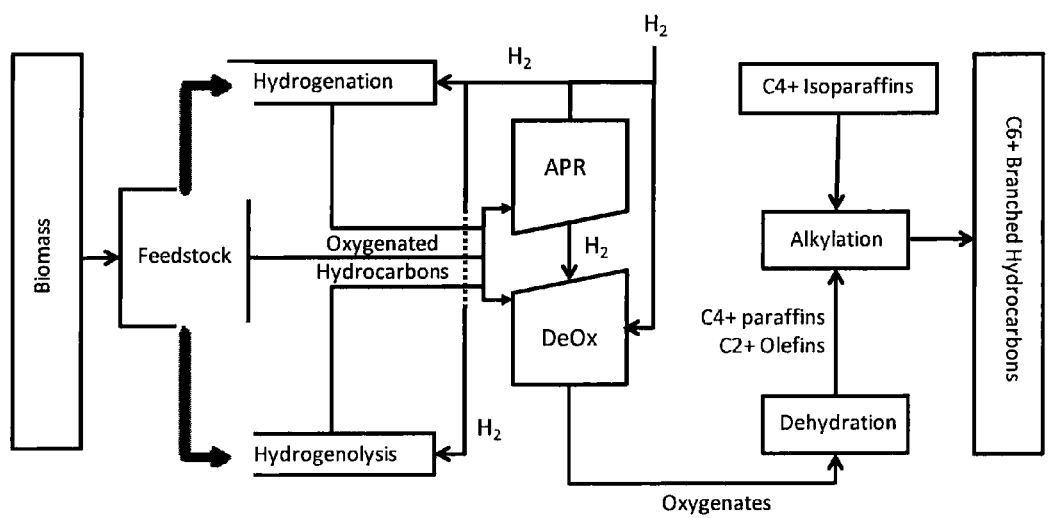
FIG. 1 is a flow diagram illustrating the production pathways associated with the present invention.

The general process is illustrated in FIG. 1. A feedstock solution containing a water-soluble oxygenated hydrocarbon having two or more carbon atoms is reacted with hydrogen over a deoxygenation catalyst to produce oxygenates and, in some instances, other hydrocarbons, such as $C_{4+}$ normal paraffins, aromatics and/or naphthenes. The oxygenates are then reacted over a dehydration catalyst to produce a reaction stream containing olefins having 2 or more carbon atoms ($C_{2+}$ olefins). The $C_{2+}$ olefins from the reaction stream are then reacted with a stream of isoparaffins ($C_{4+}$ isoparaffins) in the presence of an alkylation catalyst to produce paraffins having 6 or more carbon atoms ($C_{6+}$ paraffins). The hydrogen may originate from any source, but is preferably derived in situ (APR hydrogen) or in parallel from biomass using aqueous phase reforming. The hydrogen and oxygenated hydrocarbons may also be supplemented with recycled hydrogen and oxygenated hydrocarbons derived from the process. The $C_{4+}$ isoparaffins may also originate from any source, but are preferably generated internally from $C_{4+}$ normal paraffins, aromatics or naphthenes in the reaction stream using an isomerization catalyst. The $C_{4+}$ isoparaffins may also be provided solely from an external source or supplemented with recycled $C_{4+}$ isoparaffins and/or external $C_{4+}$isoparaffins. The water soluble oxygenated hydrocarbon may be a monosaccharide, disaccharide, polysaccharide, cellulose derivative, hemicellulose derivative, lignin derivative, sugar, sugar alcohol or other polyhydric alcohols, or may be derived from the hydrogenation of a monosaccharide, disaccharide, polysaccharide, sugar, furfural, carboxylic acid, ketone, or furan, or the hydrogenolysis of a sugar, sugar alcohol, polysaccharide, monosaccharide, disaccharide or polyhydric alcohol.

One unique aspect about the present invention is that the $C_{6+}$ paraffins can be derived from biomass components using catalytic processes instead of microorganisms, enzymes, high temperature gasification or transesterification methods. The present invention can also generate hydrogen in situ to avoid reliance on external hydrogen sources, such as hydrogen generated from the steam reforming of natural gas, or the electrolysis or thermolysis of water. The present invention also generates water, which may be recycled and used in upstream processes or returned to the environment. The present invention is also able to generate non-condensable fuel gases for purposes of providing a heat source within the reactor system or for external processes.

Carbohydrates are the most widely distributed, naturally occurring organic compounds on Earth. Carbohydrates are produced during photosynthesis, a process in which the energy from the sun is converted into chemical energy by combining carbon dioxide with water to form carbohydrates and oxygen:

$$6\ CO_2 + 6\ H_2O \xrightarrow{Sunlight} C_6H_{12}O_6 + 6\ O_2$$

The energy from sunlight is stored through this process as chemical energy in the form of carbohydrates in plants. The carbohydrates, especially when in a sugar form, are highly reactive compounds that are readily oxidized by living organisms to generate energy, carbon dioxide and water. Plant materials store these carbohydrates either as sugars, starches, polymeric cellulose, and/or hemi-cellulose.

The presence of oxygen in the molecular structure of carbohydrates contributes to the reactivity of sugars in biological systems. Ethanol fermentation technology takes advantage of this highly reactive nature by forming ethanol at ambient temperatures. Fermentation essentially de-functionalizes the highly reactive sugar to generate a partially oxidized hydrocarbon, ethanol. However, ethanol has substantial disadvantages with respect to energy value compared to hydrocarbon fuels.

Figure 2:
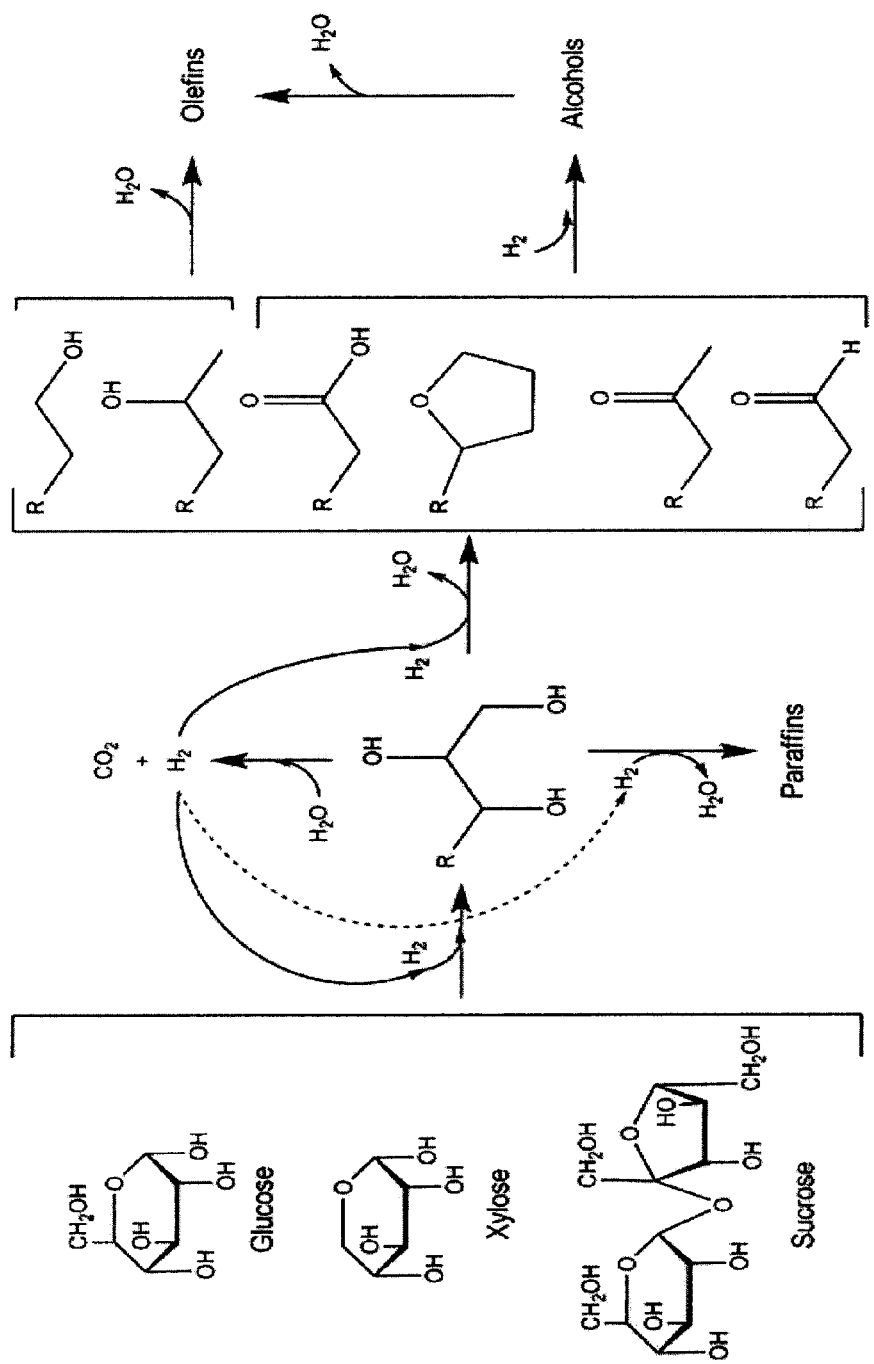
FIG. 2 is an illustration of potential chemical routes that allow carbohydrates, such as sugars, to be converted to non-oxygenated hydrocarbons.

FIG. 2 shows potential chemical reactions that allow carbohydrates, such as sugars, to be converted to non-oxygenated hydrocarbons. Water soluble carbohydrates are known to react with hydrogen over catalyst(s) to generate polyhydric alcohols, either by hydrogenation or hydrogenolysis. The hydrogen has historically been generated externally, i.e., from natural gas or by other processes, but can now be generated in situ or in parallel according to the present invention through the aqueous-phase reforming of the polyhydric alcohol.

The aqueous-phase reforming (APR) of the polyhydric alcohol proceeds through the formation of an aldehyde (shown in FIG. 2) where the aldehyde reacts over a catalyst with water to form hydrogen, carbon dioxide, and smaller polyhydric alcohols. The polyhydric alcohol can further react with hydrogen over a catalyst through a series of deoxygenation reactions to form hydroxyl, carbonyl, or aldehyde species that can undergo dehydration and hydrogenation/dehydration reactions to form olefins. Paraffins, aromatics and naphthenes are also typically formed as part of these reactions and can be converted to isoparaffins using standard isomerization techniques and subsequently used in alkylation reactions with olefins to produce paraffins for liquid fuel applications.

The de-functionalization begins by reacting the sugar with hydrogen in either a hydrogenation reaction or hydrogenolysis reaction to convert the cyclic sugar molecule to a corresponding linear alcohol—such as sorbitol—or lower polyhydric alcohols, such as glycerol, propylene glycol, ethylene glycol, xylitol, among others. The hydrogen may be from any source, but is preferably hydrogen generated in situ by aqueous phase reforming, or excess hydrogen recycled from the reactor system.

During the aqueous phase reforming process, the carbohydrate first undergoes dehydrogenation to provide adsorbed intermediates, prior to cleavage of C—C or C—O bonds. Subsequent cleavage of C—C bonds leads to the formation of CO and hydrogen, with the CO then reacting with water to form $CO_2$ and hydrogen by the water-gas shift reaction. Various APR methods and techniques are described in U.S. Pat. Nos. 6,699,457; 6,964,757 and 6,964,758; and U.S. patent application Ser. No. 11/234,727 (all to Cortright et al., and entitled "Low-Temperature Hydrogen Production from Oxygenated Hydrocarbons"); and U.S. Pat. No. 6,953,873 (to Cortright et al., and entitled "Low Temperature Hydrocarbon Production from Oxygenated Hydrocarbons"); and commonly owned co-pending International Patent Application No. PCT/US2006/048030 (to Cortright et al., and entitled "Catalyst and Methods for Reforming Oxygenated Compounds"), all of which are incorporated herein by reference. The term "aqueous phase reforming" and "APR" generically denote the reforming of oxygenated hydrocarbons and water to yield hydrogen and carbon dioxide, regardless of whether the reactions takes place in the gaseous phase or in the condensed liquid phase. "APR hydrogen" shall generically refer to the hydrogen produced by the APR process.

Figure 3:
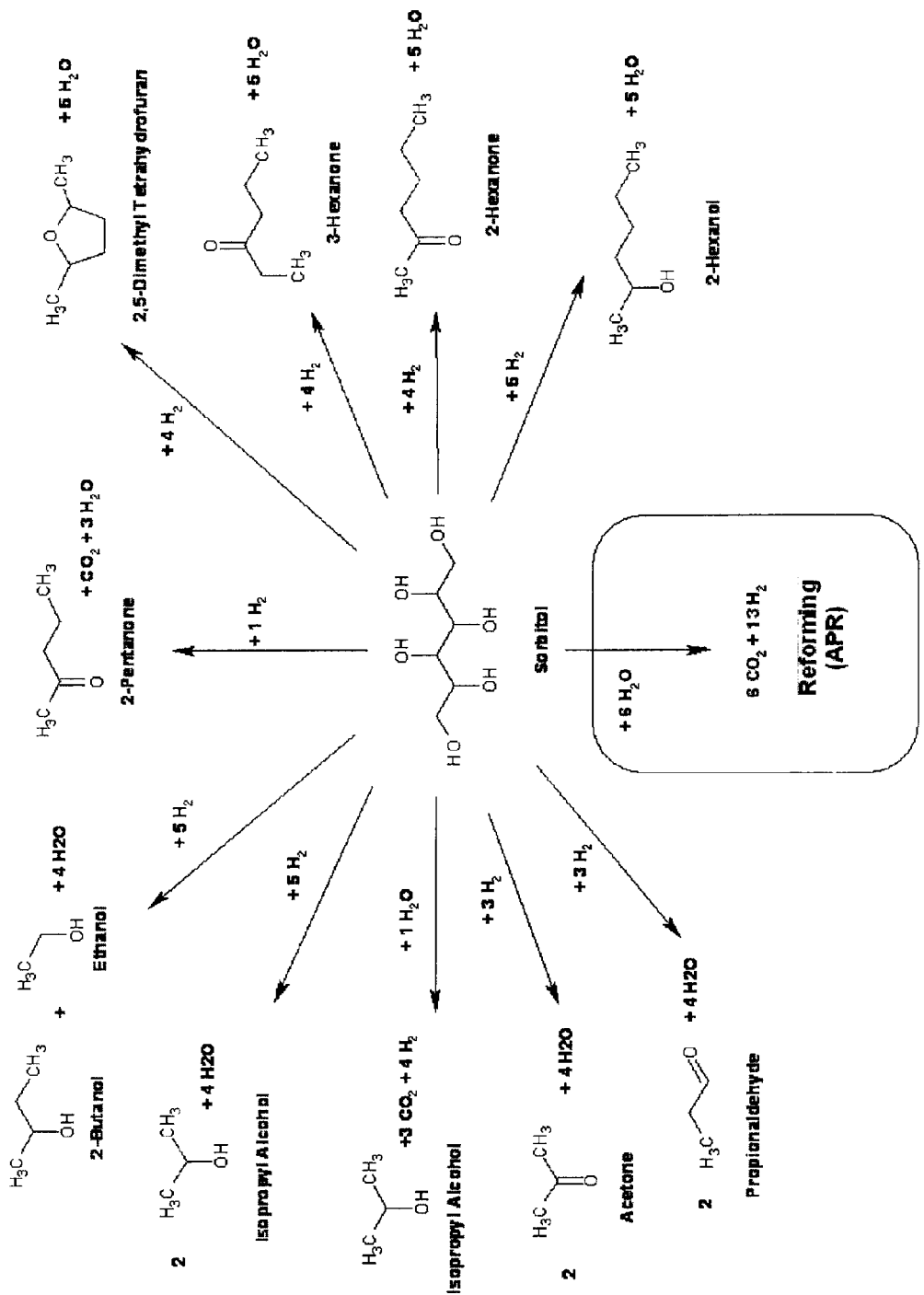
FIG. 3 is an illustration of various reaction pathways involved in the deoxygenation of sorbitol to oxygenates and APR hydrogen.

The resulting oxygenated hydrocarbon, namely the sorbitol or glycerol, propylene glycol, ethylene glycol, xylitol, etc., are further defunctionalized through deoxygenation reactions to form oxygenates, such as alcohols, ketones, aldehydes, furans, diols, triols, hydroxy carboxylic acids and carboxylic acids, for use in later condensation reactions, such as alkylation. FIG. 3 illustrates various reaction pathways involved in the deoxygenation of sorbitol to oxygenates and APR hydrogen. In general, without being limited to any particular theory, it is believed that the deoxygenation reactions involves a combination of various different reaction pathways, including without limitation: hydrodeoxygenation, consecutive dehydration-hydrogenation, hydrogenolysis, hydrogenation and dehydration reactions, resulting in the removal of oxygen from the oxygenated hydrocarbon to arrive at a hydrocarbon molecule having the general formula $C_{2+}O_{1-3}$ and, in some instances, hydrocarbon molecules such as paraffins, aromatics and naphthenes.

The $C_{2+}O_{1-3}$ hydrocarbons (oxygenates) are then converted into olefins through dehydration reactions and/or successive hydrogenation-dehydration reactions. In dehydration cases, alcohols found in the $C_{2+}O_{1-3}$ hydrocarbons are reacted to olefins by the removal of the —OH group through the interaction between the hydroxyl group and acid sites on the dehydration catalyst. If ketones, acids and aldehydes are present, they too can be defunctionalized by first reducing the carbonyl compound in the ketone, acid or aldehyde to a primary or secondary alcohol by a hydrogenation reaction involving the introduction of hydrogen over a hydrogenation catalyst, followed by a subsequent dehydration reaction as described above to provide olefins.

The paraffins are obtained by the alkylation of isoparaffins with olefins in the presence of a strong acid catalyst. In general, the alkylation process converts small olefin and isoparaffin molecules into larger paraffin compounds with a high octane number. The actual reactions taking place in the alkylation process are complex and are generally believed to include an initiation step and a propagation step. Considering the alkylation reaction of butylene with isobutane using hydrofluoric acid catalyst the initiation step is thought to generate a tertiary butyl cation that will subsequently carry on the alkylation reaction. The propagation reaction involves the tertiary butyl cation reacting with an olefin to form a larger carbenium ion, which then abstracts a hydride from an isobutane molecule. The hydride abstraction generates the desired branched paraffin, plus a new tertiary butyl cation to carry on the reaction chain.

Oxygenated Hydrocarbons

One feature of the present invention is the ability to convert highly functionalized water soluble oxygenated hydrocarbons into defunctionalized oxygenates capable of further reaction to more useable products, such as the $C_{6+}$ paraffins of the present invention. The oxygenated hydrocarbons may originate from any source, but are preferably derived from biomass. As used herein, the term "biomass" refers to, without limitation, organic materials produced by plants (such as leaves, roots, seeds and stalks), and microbial and animal metabolic wastes. Common sources of biomass include: (1) agricultural wastes, such as corn stalks, straw, seed hulls, sugarcane leavings, bagasse, nutshells, and manure from cattle, poultry, and hogs; (2) wood materials, such as wood or bark, sawdust, timber slash, and mill scrap; (3) municipal waste, such as waste paper and yard clippings; and (4) energy crops, such as poplars, willows, switch grass, alfalfa, prairie bluestream, corn, soybean, and the like. The term also refers to the primary building blocks of the above, namely, saccharides, lignin, cellulosics, hemicellulose and starches, among others.

The oxygenated hydrocarbons may be any water-soluble oxygenated hydrocarbon having 2 or more carbon atoms and 1 to 3 2 or more oxygen atoms (referred to herein as $C_{2+}O_{2+}$ $C_{2+}O_{1+}$ hydrocarbons). Preferably, the oxygenated hydrocarbon has 2 to 12 carbon atoms ($C_{1-12}O_{1-11}$ hydrocarbon), and more preferably 2 to 6 carbon atoms ($C_{1-6}O_{1-6}$ hydrocarbon). The oxygenated hydrocarbon may also have an oxygen-to-carbon ratio ranging from 0.5:1 to 1.5:1, including ratios of 0.75:1.0, 1.0:1.0, 1.25:1.0, 1.5:1.0, and other ratios between. In one example, the oxygenated hydrocarbon has an oxygen-to-carbon ratio of 1:1. Nonlimiting examples of preferred water-soluble oxygenated hydrocarbons include monosaccharides, disaccharides, polysaccharides, sugar, sugar alcohols, alditols, ethanediol, ethanedione, acetic acid, propanol, propanediol, propionic acid, glycerol, glyceraldehyde, dihydroxyacetone, lactic acid, pyruvic acid, malonic acid, butanediols, butanoic acid, aldotetroses, tautaric acid, aldopentoses, aldohexoses, ketotetroses, ketopentoses, ketohexoses, alditols, hemicelluloses, cellulosic derivatives, lignocellulosic derivatives, starches, polyols and the like. Preferably, the oxygenated hydrocarbon includes sugar, sugar alcohols, saccharides and other polyhydric alcohols. More preferably, the oxygenated hydrocarbon is a sugar, such as glucose, fructose, sucrose, maltose, lactose, mannose or xylose, or a sugar alcohol, such as arabitol, erythritol, glycerol, isomalt, lactitol, malitol, mannitol, sorbitol, xylitol, ribitol, or glycol.

Oxygenated hydrocarbons may also include those compounds derived by the hydrogenation or hydrogenolysis of any of the foregoing. In certain embodiments, it may be preferable to convert the starting oxygenated hydrocarbon to another oxygenated hydrocarbon form that can be more readily converted to the desired oxygenates (e.g., primary, secondary, tertiary or polyhydric alcohols). For instance, some sugars may not convert as efficiently to oxygenates as compared to their corresponding sugar alcohol derivatives. It may therefore be desirable to convert the starting material, such as a monosaccharide, disaccharide, polysaccharide, sugar, furfural, carboxylic acid, ketone, or furan, into its corresponding alcohol derivative, such as by hydrogenation, or to smaller alcohol molecules, such as by hydrogenolysis.

Various processes are known for hydrogenating sugars, furfurals, carboxylic acids, ketones, and furans to their corresponding alcohol form, including those disclosed by: B.S. Kwak et al. (WO2006/093364A1 and WO 2005/021475A1), involving the preparation of sugar alditols from monosaccharides by hydrogenation over a ruthenium catalyst; and Elliot et al. (U.S. Pat. Nos. 6,253,797 and 6,570,043), disclosing the use of a nickel and rhenium free ruthenium catalyst on a more than 75% rutile titania support to convert sugars to sugar alcohols, all incorporated herein by reference. Other suitable ruthenium catalysts are described by Arndt et al. in published U.S. patent application 2006/0009661 (filed Dec. 3, 2003), and Arena in U.S. Pat. No. 4,380,679 (filed Apr. 12, 1982), U.S. Pat. No. 4,380,680 (filed May 21, 1982), U.S. Pat. No. 4,503,274 (filed Aug. 8, 1983), U.S. Pat. No. 4,382,150 (filed Jan. 19, 1982), and U.S. Pat. No. 4,487,980 (filed Apr. 29, 1983), all incorporated herein by reference. The hydrogenation catalyst generally includes Cu, Re, Ni, Fe, Co, Ru, Pd, Rh, Pt, Os, Ir, and alloys or combinations thereof, either alone or with promoters such as W, Mo, Au, Ag, Cr, Zn, Mn, Sn, B, P, Bi, and alloys or combinations thereof. The hydrogenation catalyst may also include any one of the supports further described below, and depending on the desired functionality of the catalyst. Other effective hydrogenation catalyst materials include either supported nickel or ruthenium modified with rhenium. In general, the hydrogenation reaction is carried out at hydrogenation temperatures of between about 80° C. to 250° C., and hydrogenation pressures in the range of about 100 psig to 2000 psig. The hydrogen used in the reaction may include in situ generated APR hydrogen, external hydrogen, recycled hydrogen, or a combination thereof.

The hydrogenation catalyst may also include a supported Group VIII metal catalyst and a metal sponge material, such as a sponge nickel catalyst. Activated sponge nickel catalysts (e.g., Raney nickel) are a well-known class of materials effective for various hydrogenation reactions. One type of sponge nickel catalyst is the type A7063 catalyst available from Activated Metals and Chemicals, Inc., Sevierville, Tenn. The type A7063 catalyst is a molybdenum promoted catalyst, typically containing approximately 1.5% molybdenum and 85% nickel. The use of the sponge nickel catalyst with a feedstock comprising xylose and dextrose is described by M. L. Cunningham et al. in U.S. Pat. No. 6,498,248, filed Sep. 9, 1999, incorporated herein by reference. The use of a Raney nickel catalyst with hydrolyzed corn starch is also described in U.S. Pat. No. 4,694,113, filed Jun. 4, 1986, and incorporated herein by reference.

The preparation of suitable Raney nickel hydrogenation catalysts is described by A. Yoshino et al. in published U.S. patent application 2004/0143024, filed Nov. 7, 2003, incorporated herein by reference. The Raney nickel catalyst may be prepared by treating an alloy of approximately equal amounts by weight of nickel and aluminum with an aqueous alkali solution, e.g., containing about 25 wt. % of sodium hydroxide. The aluminum is selectively dissolved by the aqueous alkali solution leaving particles having a sponge construction and composed predominantly of nickel with a minor amount of aluminum. Promoter metals, such as molybdenum or chromium, may be also included in the initial alloy in an amount such that about 1-2 wt. % remains in the sponge nickel catalyst.

In another embodiment, the hydrogenation catalyst is prepared by impregnating a suitable support material with a solution of ruthenium(III)nitrosylnitrate, ruthenium(III)nitrosylnitrate, or ruthenium(III)chloride in water to form a solid that is then dried for 13 hours at 120° C. in a rotary ball oven (residual water content is less than 1% by weight). The solid is then reduced at atmospheric pressure in a hydrogen stream at 300° C. (uncalcined) or 400° C. (calcined) in the rotary ball furnace for 4 hours. After cooling and rendering inert with nitrogen, the catalyst may then be passivated by passing over 5% by volume of oxygen in nitrogen for a period of 120 minutes.

In yet another embodiment, the hydrogenation reaction is performed using a catalyst comprising a nickel-rhenium catalyst or a tungsten-modified nickel catalyst. One example of a suitable hydrogenation catalyst is the carbon-supported nickel-rhenium catalyst composition disclosed by Werpy et al. in U.S. Pat. No. 7,038,094, filed Sep. 30, 2003, and incorporated herein by reference.

In other embodiments, it may also be desirable to convert the starting oxygenated hydrocarbon, such as a sugar, sugar alcohol or other polyhydric alcohol, to a smaller molecule that can be more readily converted to the desired oxygenates, such as by hydrogenolysis. Such smaller molecules may include primary, secondary, tertiary or polyhydric alcohols having less carbon atoms than the originating oxygenated hydrocarbon. Various processes are known for such hydrogenolysis reactions, including those disclosed by: Werpy et al. in U.S. Pat. No. 6,479,713 (filed Oct. 23, 2001), U.S. Pat. No. 6,677,385 (filed Aug. 6, 2002), U.S. Pat. No. 6,6841,085 (filed Oct. 23, 2001) and U.S. Pat. No. 7,083,094 (filed Sep. 30, 2003), all incorporated herein by reference and describing the hydrogenolysis of 5 and 6 carbon sugars and sugar alcohols to propylene glycol, ethylene glycol and glycerol using a rhenium-containing multi-metallic catalyst. Other systems include those described by Arena in U.S. Pat. No. 4,401,823 (filed May 18, 1981) directed to the use of a carbonaceous pyropolymer catalyst containing transition metals (such as chromium, molybdenum, tungsten, rhenium, manganese, copper, cadmium) or Group VIII metals (such as iron, cobalt, nickel, platinum, palladium, rhodium, ruthenium, iridium and osmium) to produce alcohols, acids, ketones, and ethers from polyhydroxylated compounds, such as sugars and sugar alcohols, and U.S. Pat. No. 4,496,780 (filed Jun. 22, 1983) directed to the use of a catalyst system having a Group VIII noble metal on a solid support with an alkaline earth metal oxide to produce glycerol, ethylene glycol and 1,2-propanediol from carbohydrates, each incorporated herein by reference. Another system includes that described by Dubeck et al. in U.S. Pat. No. 4,476,331 (filed Sep. 6, 1983) directed to the use of a sulfide-modified ruthenium catalyst to produce ethylene glycol and propylene glycol from larger polyhydric alcohols, such as sorbitol, also incorporated herein by reference. Other systems include those described by Saxena et al., "Effect of Catalyst Constituents on (Ni,MoandCu)/Kieselguhr-Catalyzed Sucrose Hydrogenolysis," Ind. Eng. Chem. Res. 44, 1466-1473 (2005), describing the use of Ni, W, and Cu on a kieselguhr support, incorporated herein by reference.

In one embodiment, the hydrogenolysis catalyst includes Cr, Mo, W, Re, Mn, Cu, Cd, Fe, Co, Ni, Pt, Pd, Rh, Ru, Ir, or Os, and alloys or combinations thereof, either alone or with promoters such as Au, Ag, Cr, Zn, Mn, Sn, Bi, B, O and alloys or combinations thereof. Other effective hydrogenolysis catalyst materials may include the above metals combined with an alkaline earth metal oxide or adhered to catalytically active support, such as kieselguhr, or any one of the supports further described below.

The process conditions for carrying out the hydrogenolysis reaction will vary depending on the type of feedstock and desired products. In general, the hydrogenolysis reaction is conducted at temperatures of at least 110° C., or between 110° C. and 300° C., or between 170° C. and 240° C. The reaction should also be conducted under basic conditions, preferably at a pH of about 8 to about 13, or at a pH of about 10 to about 12. The reaction should also be conducted at pressures of between about 10 psig and 2400 psig, or between about 250 psig and 2000 psig, or between about 700 psig and 1600 psig. The hydrogen used in the reaction may include APR hydrogen, external hydrogen, recycled hydrogen, or a combination thereof.

Oxygenates

As used herein, "oxygenates" generically refers to hydrocarbon compounds having 2 or more carbon atoms and between 1 and 3 oxygen atoms (referred to herein as $C_{2+}O_{1-3}$ hydrocarbons), such as alcohols, ketones, aldehydes, furans, hydroxy carboxylic acids, carboxylic acids, diols and triols. Preferably, oxygenates have from 2 to 6 carbon atoms, or 3 to 5 carbon atoms. Alcohols may include, without limitation, primary, secondary, linear, branched or cyclic $C_{2+}$ alcohols, such as ethanol, n-propyl alcohol, isopropyl alcohol, butyl alcohol, isobutyl alcohol, butanol, pentanol, cyclopentanol, hexanol, cyclohexanol, 2-methyl-cyclopentanonol, heptanol, octanol, nonanol, decanol, undecanol, dodecanol, and isomers thereof. The ketones may include, without limitation, hydroxyketones, cyclic ketones, diketones, acetone, propanone, 2-oxopropanal, butanone, butane-2,3-dione, 3-hydroxybutan-2-one, pentanone, cyclopentanone, pentane-2,3-dione, pentane-2,4-dione, hexanone, cyclohexanone, 2-methyl-cyclopentanone, heptanone, octanone, nonanone, decanone, undecanone, dodecanone, methylglyoxal, butanedione, pentanedione, diketohexane, and isomers thereof. The aldehydes may include, without limitation, hydroxyaldehydes, acetaldehyde, propionaldehyde, butyraldehyde, pentanal, hexanal, heptanal, octanal, nonal, decanal, undecanal, dodecanal, and isomers thereof. The carboxylic acids may include, without limitation, formic acid, acetic acid, propionic acid, butanoic acid, pentanoic acid, hexanoic acid, heptanoic acid, isomers and derivatives thereof, including hydroxylated derivatives, such as 2-hydroxybutanoic acid and lactic acid. The diols may include, without limitation, ethylene glycol, propylene glycol, 1,3-propanediol, butanediol, pentanediol, hexanediol, heptanediol, octanediol, nonanediol, decanediol, undecanediol, dodecanediol, and isomers thereof. The triols may include, without limitation, glycerol, 1,1,1 tris(hydroxymethyl)-ethane(trimethylolethane), trimethylolpropane, hexanetriol, and isomers thereof. Furans and furfurals include, without limitation, furan, tetrahydrofuran, dihydrofuran, 2-furan methanol, 2-methyl-tetrahydrofuran, 2,5-dimethyl-tetrahydrofuran, 2-methyl furan, 2-ethyl-tetrahydrofuran, 2-ethyl furan, hydroxylmethylfurfural, 3-hydroxytetrahydrofuran, tetrahydro-3-furanol, 2,5-dimethyl furan, 5-hydroxymethyl-2(5H)-furanone, dihydro-5-(hydroxymethyl)-2(3H)-furanone, tetrahydro-2-furoic acid, dihydro-5-(hydroxymethyl)-2(3H)-furanone, hydroxymethyl tetrahydrofurfural, tetrahydrofurfuryl alcohol, 1-(2-furypethanol, and isomers thereof.

Oxygenates are prepared by reacting an aqueous feedstock solution containing water and the water soluble oxygenated hydrocarbons with hydrogen over a deoxygenation catalyst. Preferably, the hydrogen is generated in situ using aqueous phase reforming (in situ generated hydrogen or APR hydrogen), or a combination of APR hydrogen, external hydrogen or recycled hydrogen, or just simply external hydrogen or recycled hydrogen. The term "external hydrogen" refers to hydrogen that does not originate from the feedstock solution, but is added to the reactor system from an external source. The term "recycled hydrogen" refers to unconsumed hydrogen that originates from the feedstock solution, and which is collected and then recycled back into the reactor system for further use. External hydrogen and recycled hydrogen may also be referred to collectively or individually as "supplemental hydrogen." In general, supplemental hydrogen may be added for purposes of supplementing the APR hydrogen, or to substitute the inclusion of an APR hydrogen production step, or to increase the reaction pressure within the system, or to increase the molar ratio of hydrogen to carbon and/or oxygen in order to enhance the production yield of certain reaction product types, such as ketones and alcohols.

In processes utilizing APR hydrogen, the oxygenates are prepared by catalytically reacting a portion of the aqueous feedstock solution containing water and the water soluble oxygenated hydrocarbons in the presence of an APR catalyst at a reforming temperature and reforming pressure to produce the APR hydrogen, and catalytically reacting the APR hydrogen (and recycled hydrogen and/or external hydrogen) with a portion of the feedstock solution in the presence of a deoxygenation catalyst at a deoxygenation temperature and deoxygenation pressure to produce the desired oxygenates. In systems utilizing recycled hydrogen or external hydrogen as a hydrogen source, oxygenates are simply prepared by catalytically reacting the recycled hydrogen and/or external hydrogen with the feedstock solution in the presence of the deoxygenation catalyst at the deoxygenation temperatures and pressures. In each of the above, oxygenates may also include recycled oxygenates (recycled $C_{1+}O_{1-3}$ hydrocarbons). Unless otherwise indicated, any discussions of APR catalysts and deoxygenation catalysts are non-limiting examples of suitable catalytic materials.

The deoxygenation catalyst is preferably a heterogeneous catalyst having one or more materials capable of catalyzing a reaction between hydrogen and the oxygenated hydrocarbon to remove one or more of the oxygen atoms from the oxygenated hydrocarbon to produce alcohols, ketones, aldehydes, furans, carboxylic acids, hydroxy carboxylic acids, diols and triols. In general, the materials Will be adhered to a support and may include, without limitation, Cu, Re, Fe, Ru, Ir, Co, Rh, Pt, Pd, Ni, W, Os, Mo, Ag, Au, alloys and combinations thereof. The deoxygenation catalyst may include these elements alone or in combination with one or more Mn, Cr, Mo, W, V, Nb, Ta, Ti, Zr, Y, La, Sc, Zn, Cd, Ag, Au, Sn, Ge, P, Al, Ga, In, Tl, and combinations thereof. In one embodiment, the deoxygenation catalyst includes Pt, Ru, Cu, Re, Co, Fe, Ni, W or Mo. In yet another embodiment, the deoxygenation catalyst includes Fe or Re and at least one transition metal selected from Ir, Ni, Pd, P, Rh, and Ru. In another embodiment, the catalyst includes Fe, Re and at least Cu or one Group VIIIB transition metal. The support may be any one of the supports further described below, including a nitride, carbon, silica, alumina, zirconia, titania, vanadia, ceria, zinc oxide, chromia, boron nitride, heteropolyacids, kieselguhr, hydroxyapatite, and mixtures thereof. The deoxygenation catalyst may also be atomically identical to the APR catalyst or the alkylation catalyst.

The deoxygenation catalyst may also be a bi-functional catalyst. For example, acidic supports (e.g., supports having low isoelectric points) are able to catalyze dehydration reactions of oxygenated compounds, followed by hydrogenation reactions on metallic catalyst sites in the presence of hydrogen, again leading to carbon atoms that are not bonded to oxygen atoms. The bi-functional dehydration/ hydrogenation pathway consumes hydrogen and leads to the subsequent formation of various polyols, diols, ketones, aldehydes, alcohols and cyclic ethers, such as furans and pyrans. Catalyst examples include tungstated zirconia, titania zirconia, sulfated zirconia, acidic alumina, silica-alumina, zeolites and heteropolyacid supports. Heteropolyacids are a class of solid-phase acids exemplified by such species as $H_{3+x}PMo_{12-x}V_xO_{40}$, $H_4SiW_{12}O_{40}$, $H_3PW_{12}O_{40}$, and $H_6P2W_{18}O_{62}$. Heteropolyacids are solid-phase acids having a well-defined local structure, the most common of which is the tungsten-based Keggin structure.

Loading of the first element (i.e., Cu, Re, Fe, Ru, Ir, Co, Rh, Pt, Pd, Ni, W, Os, Mo, Ag, Au, alloys and combinations thereof) is in the range of 0.25 wt % to 25 wt % on carbon, with weight percentages of 0.10% and 0.05% increments between, such as 1.00%, 1.10%, 1.15%, 2.00%, 2.50%, 5.00%, 10.00%, 12.50%, 15.00% and 20.00%. The preferred atomic ratio of the second element (i.e., Mn, Cr, Mo, W, V, Nb, Ta, Ti, Zr, Y, La, Sc, Zn, Cd, Ag, Au, Sn, Ge, P, AI, Ga, In, TI, and combinations thereof) is in the range of 0.25-to-1 to 10-to-1, including any ratios between, such as 0.50, 1.00, 2.50, 5.00, and 7.50-to-1. If the catalyst is adhered to a support, the combination of the catalyst and the support is from 0.25 wt % to 10 wt % of the primary element.

To produce oxygenates, the water soluble oxygenated hydrocarbon is combined with water to provide an aqueous feedstock solution having a concentration effective for causing the formation of the desired reaction products. The water-to-carbon ratio on a molar basis is preferably from about 0.5:1 to about 100:1, including ratios such as 1:1, 2:1, 3:1, 4:1, 5:1, 6:1, 7:1, 8:1, 9:1, 10:1, 15:1, 25:1, 50:1 75:1, 100:1, and any ratios there-between. The feedstock solution may also be characterized as a solution having at least 1.0 weight percent (wt %) of the total solution as an oxygenated hydrocarbon. For instance, the solution may include one or more oxygenated hydrocarbons, with the total concentration of the oxygenated hydrocarbons in the solution being at least about 1%, 5%, 10%, 20%, 30%, 40%, 50%, 60%, 70%, 80% or greater by weight, including any percentages between, and depending on the oxygenated hydrocarbons used. In one embodiment, the feedstock solution includes at least about 10%, 20%, 30%, 40%, 50%, or 60% of a sugar, such as glucose, fructose, sucrose or xylose, or a sugar alcohol, such as sorbitol, mannitol, glycerol or xylitol, by weight. Water-to-carbon ratios and percentages outside of the above stated ranges are also included. Preferably the balance of the feedstock solution is water. In some embodiments, the feedstock solution consists essentially of water, one or more oxygenated hydrocarbons and, optionally, one or more feedstock modifiers described herein, such as alkali or hydroxides of alkali or alkali earth salts or acids. The feedstock solution may also include recycled oxygenated hydrocarbons recycled from the reactor system. The feedstock solution may also contain negligible amounts of hydrogen, preferably less than about 1.5 mole of hydrogen per mole of feedstock. In the preferred embodiments, hydrogen is not added to the feedstock solution.

The feedstock solution is reacted with hydrogen in the presence of the deoxygenation catalyst at deoxygenation temperature and pressure conditions, and weight hourly space velocity, effective to produce the desired oxygenates. The specific oxygenates produced will depend on various factors, including the feedstock solution, reaction temperature, reaction pressure, water concentration, hydrogen concentration, the reactivity of the catalyst, and the flow rate of the feedstock solution as it affects the space velocity (the mass/volume of reactant per unit of catalyst per unit of time), gas hourly space velocity (GHSV), and weight hourly space velocity (WHSV). For example, an increase in flow rate, and thereby a reduction of feedstock exposure to the catalysts over time, will limit the extent of the reactions which may occur, thereby causing increased yield for higher level diols and triols, with a reduction in ketone and alcohol yields.

The deoxygenation temperature and pressure are preferably selected to maintain at least a portion of the feedstock in the liquid phase at the reactor inlet. It is recognized, however, that temperature and pressure conditions may also be selected to more favorably produce the desired products in the vapor-phase. In general, the reaction should be conducted at process conditions wherein the thermodynamics of the proposed reaction are favorable. For instance, the minimum pressure required to maintain a portion of the feedstock in the liquid phase will likely vary with the reaction temperature. As temperatures increase, higher pressures will generally be required to maintain the feedstock in the liquid phase, if desired. Pressures above that required to maintain the feedstock in the liquid phase (i.e., vapor-phase) are also suitable operating conditions.

In condensed phase liquid reactions, the pressure within the reactor must be sufficient to maintain the reactants in the condensed liquid phase at the reactor inlet. For liquid phase reactions, the reaction temperature may be from about 80° C. to 300° C., and the reaction pressure from about 72 psig to 1300 psig. In one embodiment, the reaction temperature is between about 120° C. and 300° C., or between about 200° C. and 280° C., or between about 220° C. and 260° C., and the reaction pressure is preferably between about 72 and 1200 psig, or between about 145 and 1200 psig, or between about 200 and 725 psig, or between about 365 and 700 psig, or between about 600 and 650 psig.

For vapor phase reactions, the reaction should be carried out at a temperature where the vapor pressure of the oxygenated hydrocarbon is at least about 0.1 atm (and preferably a good deal higher), and the thermodynamics of the reaction are favorable. This temperature will vary depending upon the specific oxygenated hydrocarbon compound used, but is generally in the range of from about 100° C. to 600° C. for vapor phase reactions. Preferably, the reaction temperature is between about 120° C. and about 300° C., or between about 200° C. and about 280° C., or between about 220° C. and about 260° C.

In another embodiment, the deoxygenation temperature is between about 100° C. and 400° C., or between about 120° C. and 300° C., or between about 200° C. and 280° C., and the reaction pressure is preferably between about 72 and 1300 psig, or between about 72 and 1200 psig, or between about 200 and 725 psig, or between about 365 and 700 psig.

A condensed liquid phase method may also be performed using a modifier that increases the activity and/or stability of the catalyst system. It is preferred that the water and the oxygenated hydrocarbon are reacted at a suitable pH of from about 1.0 to about 10.0, including pH values in increments of 0.1 and 0.05 between, and more preferably at a pH of from about 4.0 to about 10.0. Generally, the modifier is added to the feedstock solution in an amount ranging from about 0.1% to about 10% by weight as compared to the total weight of the catalyst system used, although amounts outside this range are included within the present invention.

In general, the reaction should be conducted under conditions where the residence time of the feedstock solution over the catalyst is appropriate to generate the desired products. For example, the WHSV for the reaction may be at least about 0.1 gram of oxygenated hydrocarbon per gram of catalyst per hour, and more preferably the WHSV is about 0.1 to 40.0 g/g hr, including a WHSV of about 0.25, 0.5, 0.75, 1.0, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 6, 7, 8, 9, 10, 11, 12, 13, 14, 15, 20, 25, 30, 35, 40 g/g hr.

The hydrogen used in the deoxygenation reaction is preferably in-situ generated APR hydrogen, but may also be external or recycled hydrogen. When present, the amount of external hydrogen is preferably provided sparingly. Most preferably, the amount of external hydrogen is provided in amounts that provide less than one hydrogen atom per oxygen atom in all of the oxygenated hydrocarbons in the feedstock stream prior to contacting the deoxygenation catalyst. For example, the molar ratio between the external hydrogen and the total water-soluble oxygenated hydrocarbons in the feedstock solution is preferably selected to provide no more than one hydrogen atom per oxygen atom in the oxygenated hydrocarbon. The molar ratio of the oxygenated hydrocarbons in the feedstock to the external hydrogen introduced to the feedstock is also preferably not more than 1:1, or more preferably up to 2:1, 3:1, 5:1, 10:1, 20:1 or greater (including 4:1, 6:1, 7:1, 8:1, 9:1, 11:1, 12:1, 13:1, 14:1, 15:1, 16:1, 17:1, 18:1 and 19:1). The amount (moles) of external hydrogen introduced to the feedstock is between 0-100%, 0-95%, 0-90%, 0-85%, 0-80%, 0-75%, 0-70%, 0-65%, 0-60%, 0-55%, 0-50%, 0-45%, 0-40%, 0-35%, 0-30%, 0-25%, 0-20%, 0-15%, 0-10%, 0-5%, 0-2%, or 0-1% of the total number of moles of the oxygenated hydrocarbon(s) in the feedstock, including all intervals between. When the feedstock solution, or any portion thereof, is reacted with APR hydrogen and external hydrogen, the molar ratio of APR hydrogen to external hydrogen is at least 1:20; 1:15, 1:10, 1:5; 1:3, 1:2, 1:1, 2:1, 3:1, 5:1, 10:1, 15:1, 20:1, and ratios between (including 4:1, 6:1, 7:1, 8:1, 9:1, 11:1, 12:1, 13:1, 14:1, 15:1, 16:1, 17:1, 18:1 and 19:1, and vice-versa). Preferably, the oxygenated hydrocarbon is reacted with hydrogen in the presence of an insignificantly effective amount of external hydrogen.

The amount of external hydrogen (or supplemental hydrogen) added may be calculated by considering the concentration of the oxygenated hydrocarbons in the feedstock solution. Preferably, the amount of supplemental hydrogen added should provide a molar ratio of oxygen atoms in the oxygenated hydrocarbons to moles of hydrogen atoms (i.e., 2 oxygen atoms per molecule of hydrogen gas) of less than or equal to 1.0. For example, where the feedstock is an aqueous solution consisting of glycerol (3 oxygen atoms), the amount of supplemental hydrogen added to the feedstock is preferably not more than about 1.5 moles of $H_2$ per mole of glycerol ($C_3H_8O_3$), and preferably not more than about 1.25, 1.0, 0.75, 0.50 or 0.25. In general, the amount of supplemental hydrogen added is less than 0.75-times, and more preferably not more than 0.67, 0.50, 0.33, 0.30, 0.25, 0.20, 0.15, 0.10, 0.05, 0.01-times the amount of total hydrogen (APR hydrogen and supplemental hydrogen) that would provide a 1:1 atomic ratio of oxygen to hydrogen atoms.

The amount of APR hydrogen within a reactor may be identified or detected by any suitable method. APR hydrogen may be determined based on the composition of the product stream as a function of the composition of the feedstock stream, the catalyst composition(s) and the reaction conditions, independent of the actual reaction mechanism occurring within the feedstock stream. The amount of APR hydrogen may be calculated based on the catalyst, reaction conditions (e.g., flow rate, temperature, pressure, etc.) and the contents of the feedstock and the reaction products. For example, the feedstock may be contacted with the APR catalyst (e.g., platinum) to generate APR hydrogen in snit and a first reaction product stream in the absence of a deoxygenation catalyst. The feedstock may also be contacted with both the APR catalyst and the deoxygenation catalyst to produce a second reaction product stream. By comparing the composition of the first reaction product stream and the second reaction product stream at comparable reaction conditions, one may identify the presence of APR hydrogen and calculate the amount of APR hydrogen produced. For example, an increase in the amount of oxygenated compounds with greater degrees of hydrogenation in the reaction product compared to the feedstock components may indicate the presence of APR hydrogen.

In Situ Hydrogen Production

One advantage of the present invention is that it allows for the production and use of in-situ generated APR hydrogen. The APR hydrogen is produced from the feedstock under aqueous phase reforming conditions using an aqueous phase reforming catalyst (APR catalyst). The APR catalyst is preferably a heterogeneous catalyst capable of catalyzing the reaction of water and water soluble oxygenated hydrocarbons to form hydrogen under the conditions described below. In one embodiment, the APR catalyst includes a support and at least one Group VIIIB metal, Fe, Ru, Os, Ir, Co, Rh, Pt, Pd, Ni, alloys and combinations thereof. The APR catalyst may also include at least one additional material from Group VIIIB, Group VIIB, Group VIB, Group VB, Group IVB, Group IIB, Group IB, Group IVA or Group VA metals, such as Cu, B, Mn, Re, Cr, Mo, Bi, W, V, Nb, Ta, Ti, Zr, Y, La, Sc, Zn, Cd, Ag, Au, Sn, Ge, P, Al, Ga, In, Tl, alloys and combinations thereof. The preferred Group VIIB metal includes Re, Mn, or combinations thereof. The preferred Group VIB metal includes Cr, Mo, W, or a combination thereof. The preferred Group VIIIB metals include Pt, Rh, Ru, Pd, Ni, or combinations thereof. The supports may include any one of the catalyst supports described below, depending on the desired activity of the catalyst system.

The APR catalyst may also be atomically identical to the deoxygenation catalyst or the alkylation catalyst. For instance, the APR and deoxygenation catalyst may include Pt alloyed or admixed with Ni, Ru, Cu, Fe, Rh, Re, alloys and combinations thereof. The APR catalyst and deoxygenation catalyst may also include Ru alloyed or admixed with Ge, Bi, B, Ni, Sn, Cu, Fe, Rh, Pt, alloys and combinations thereof. The APR catalyst may also include Ni alloyed or admixed with Sn, Ge, Bi, B, Cu, Re, Ru, Fe, alloys and combinations thereof.

Preferred loading of the primary Group VIIIB metal is in the range of 0.25 wt % to 25 wt % on carbon, with weight percentages of 0.10% and 0.05% increments between, such as 1.00%, 1.10%, 1.15%, 2.00%, 2.50%, 5.00%, 10.00%, 12.50%, 15.00% and 20.00%. The preferred atomic ratio of the second material is in the range of 0.25-to-1 to 10-to-1, including ratios between, such as 0.50, 1.00, 2.50, 5.00, and 7.50-to-1.

A preferred catalyst composition is further achieved by the addition of oxides of Group IIIB, and associated rare earth oxides. In such event, the preferred components would be oxides of either lanthanum or cerium. The preferred atomic ratio of the Group IIIB compounds to the primary Group VIIIB metal is in the range of 0.25-to-1 to 10-to-1, including ratios between, such as 0.50, 1.00, 2.50, 5.00, and 7.50-to-1.

Another preferred catalyst composition is one containing platinum and rhenium. The preferred atomic ratio of Pt to Re is in the range of 0.25-to-1 to 10-to-1, including ratios therebetween, such as 0.50, 1.00, 2.50, 5.00, and 7.00-to-1. The preferred loading of the Pt is in the range of 0.25 wt % to 5.0 wt %, with weight percentages of 0.10% and 0.05% between, such as 0.35%, 0.45%, 0.75%, 1.10%, 1.15%, 2.00%, 2.50%, 3.0%, and 4.0%.

Preferably, the APR catalyst and the deoxygenation catalyst are of the same atomic formulation. The catalysts may also be of different formulations. In such event, the preferred atomic ratio of the APR catalyst to the deoxygenation catalyst is in the range of 5:1 to 1:5, such as, without limitation, 4.5:1, 4.0:1, 3.5:1, 3.0:1, 2.5:1, 2.0:1, 1.5:1, 1:1, 1:1.5, 1:2.0, 1:2.5, 1:3.0, 1:3.5, 1:4.0, 1:4.5, and any amounts between.

Similar to the deoxygenation reactions, the temperature and pressure conditions are preferably selected to maintain at least a portion of the feedstock in the liquid phase at the reactor inlet. The reforming temperature and pressure conditions may also be selected to more favorably produce the desired products in the vapor-phase. In general, the APR reaction should be conducted at a temperature where the thermodynamics are favorable. For instance, the minimum pressure required to maintain a portion of the feedstock in the liquid phase will vary with the reaction temperature. As temperatures increase, higher pressures will generally be required to maintain the feedstock in the liquid phase. Any pressure above that required to maintain the feedstock in the liquid phase (i.e., vapor-phase) is also a suitable operating pressure. For vapor phase reactions, the reaction should be conducted at a reforming temperature where the vapor pressure of the oxygenated hydrocarbon compound is at least about 0.1 atm (and preferably a good deal higher), and the thermodynamics of the reaction are favorable. The temperature will vary depending upon the specific oxygenated hydrocarbon compound used, but is generally in the range of from about 100° C. to 450° C., or from about 100° C. to 300° C., for reactions taking place in the vapor phase. For liquid phase reactions, the reaction temperature may be from about 80° C. to 400° C., and the reaction pressure from about 72 psig to 1300 psig.

In one embodiment, the reaction temperature is between about 100° C. and 400° C., or between about 120° C. and 300° C., or between about 200° C. and 280° C., or between about 150° C. and 270° C. The reaction pressure is preferably between about 72 and 1300 psig, or between about 72 and 1200 psig, or between about 145 and 1200 psig, or between about 200 and 725 psig, or between about 365 and 700 psig, or between about 600 and 650 psig.

A condensed liquid phase method may also be performed using a modifier that increases the activity and/or stability of the APR catalyst system. It is preferred that the water and the oxygenated hydrocarbon are reacted at a suitable pH of from about 1.0 to 10.0, or at a pH of from about 4.0 to 10.0, including pH value increments of 0.1 and 0.05 between. Generally, the modifier is added to the feedstock solution in an amount ranging from about 0.1% to about 10% by weight as compared to the total weight of the catalyst system used, although amounts outside this range are included within the present invention.

Alkali or alkali earth salts may also be added to the feedstock solution to optimize the proportion of hydrogen in the reaction products. Examples of suitable water-soluble salts include one or more selected from the group consisting of an alkali or an alkali earth metal hydroxide, carbonate, nitrate, or chloride salt. For example, adding alkali (basic) salts to provide a pH of about pH 4.0 to about pH 10.0 can improve hydrogen selectivity of reforming reactions.

The addition of acidic compounds may also provide increased selectivity to the desired reaction products in the hydrogenation reactions described below. It is preferred that the water-soluble acid is selected from the group consisting of nitrate, phosphate, sulfate, chloride salts, and mixtures thereof. If an acidic modifier is used, it is preferred that it be present in an amount sufficient to lower the pH of the aqueous feed stream to a value between about pH 1.0 and about pH 4.0. Lowering the pH of a feed stream in this manner may increase the proportion of oxygenates in the final reaction products.

In general, the reaction should be conducted under conditions where the residence time of the feedstock solution over the APR catalyst is appropriate to generate an amount of APR hydrogen sufficient to react with a second portion of the feedstock solution over the deoxygenation catalyst to provide the desired oxygenates. For example, the WHSV for the reaction may be at least about 0.1 gram of oxygenated hydrocarbon per gram of APR catalyst, and preferably between about 1.0 to 40.0 grams of oxygenated hydrocarbon per gram of APR catalyst, and more preferably between about 0.5 to 8.0 grams of oxygenated hydrocarbon per gram of APR catalyst. In terms of scaled-up production, after start-up, the APR reactor system should be process controlled so that the reactions proceed at steady-state equilibrium.

Olefins

The $C_{2+}O_{1-3}$ hydrocarbons are converted into olefins by catalytically reacting the $C_{2+}O_{1-3}$ hydrocarbons in the presence of a dehydration catalyst and at a dehydration temperature and pressure appropriate to produce $C_{2+}$ olefins. Alternatively, the olefins may be produced by catalytically reacting the $C_{2+}O_{1-3}$ hydrocarbons with hydrogen in the presence of a hydrogenation catalyst and at a hydrogenation temperature and pressure appropriate to produce $C_{2+}$ hydroxyl compounds, and catalytically reacting the $C_{2+}$ hydroxyl compounds in the presence of a dehydration catalyst and at a dehydration temperature and pressure appropriate to produce $C_{2+}$ olefins. The hydrogen used in the hydrogenation reaction may include in sin, generated APR hydrogen, external hydrogen, recycled hydrogen, or a combination thereof.

The hydrogenation catalysts may be any one of the hydrogenation catalysts described above that are capable of converting a ketone, acid or aldehyde to a $C_{2+}$ hydroxyl compounds. Such catalysts may include any one or more of the following metals, Cu, Ni, Fe, Co, Ru, Pd, Rh, Pt, Ir, Os, alloys or combinations thereof, alone or with promoters such as Au, Ag, Cr, Zn, Mn, Sn, Cu, Bi, and alloys thereof, may be used in various loadings ranging from about 0.01 to about 20 wt % on a support as described above. As used herein, $C_{2+}$ hydroxyl compound refers to any hydrocarbon molecule having 2 or more carbon atoms and at least one hydroxyl group. Examples of $C_{2+}$ hydroxyl compounds include, without limitation, primary and secondary alcohols.

The dehydration catalyst will generally be a catalyst capable of removing a hydroxyl group from a $C_{2+}O_{1-3}$ hydrocarbon to provide a $C_{2+}$ olefin. The $C_{2+}$ olefins are typically straight or branched hydrocarbons containing one or more carbon-carbon double bonds. In general, the $C_{2+}$ olefins contain from 2 to 8 carbon atoms, and more preferably from 3 to 5 carbon atoms. In one embodiment, the $C_{2+}$ olefins comprise propylene, butylene, pentylene, isomers of the foregoing, and mixtures thereof. In another embodiment, the $C_{2+}$ olefins include $C_{4+}$ olefins produced by catalytically reacting a portion of the $C_{2+}$ olefins over an olefin isomerization catalyst.

The dehydration catalysts may include, without limitation, aluminosilicates (zeolites), silica-alumina phosphates (SAPO), aluminum phosphates (ALPO), amorphous silica alumina, zirconia, sulfated zirconia, tungstated zirconia, tungsten carbide, molybdenum carbide, titania, alumina, phosphated alumina, phosphated silica, sulfated carbons, phosphated carbons, acidic resins, heteropolyacids, inorganic acids, and combinations thereof. In one embodiment, the dehydration catalyst may also include a modifier, such as Ce, Y, Sc, La, P, B, Bi, Li, Na, K, Rb, Cs, Mg, Ca, Sr, Ba, and combinations thereof. The dehydration catalyst may also be modified by the addition of a metal, such as Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof, to provide metal functionality, and/or sulfides and oxide species of Ti, Zr, V, Nb, Ta, Mo, Cr, W, Mn, Re, Al, Ga, In, Fe, Co, Tr, Ni, Si, Cu, Zn, Sn, Cd, P, and combinations thereof. The dehydration catalyst may be homogenous, self-supporting or adhered to any one of the supports further described below, including supports containing carbon, silica, alumina, zirconia, titania, vanadia, ceria, nitride, boron nitride, heteropolyacids, alloys and mixtures thereof.

Ga, In, Zn, Fe, Mo, Ag, Au, Ni, P, Sc, Y, Ta, and lanthanides may also be exchanged onto zeolites to provide a zeolite catalyst having activity. The term "zeolite" as used herein refers not only to microporous crystalline aluminosilicate but also for microporous crystalline metal-containing aluminosilicate structures, such as galloaluminosilicates and gallosilicates. Metal functionality may be provided by metals such as Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof.

Examples of suitable zeolite catalysts include ZSM-5, ZSM-11, ZSM-12, ZSM-22, ZSM-23, ZSM-35 and ZSM-48. Zeolite ZSM-5, and the conventional preparation thereof, is described in U.S. Pat. Nos. 3,702,886; Re. 29,948 (highly siliceous ZSM-5); U.S. Pat. Nos. 4,100,262 and 4,139,600, all incorporated herein by reference. Zeolite ZSM-11, and the conventional preparation thereof, is described in U.S. Pat. No. 3,709,979, which is also incorporated herein by reference. Zeolite ZSM-12, and the conventional preparation thereof, is described in U.S. Pat. No. 3,832,449, incorporated herein by reference. Zeolite ZSM-23, and the conventional preparation thereof, is described in U.S. Pat. No. 4,076,842, incorporated herein by reference. Zeolite ZSM-35, and the conventional preparation thereof, is described in U.S. Pat. No. 4,016,245, incorporated herein by reference. Another preparation of ZSM-35 is described in U.S. Pat. No. 4,107,195, the disclosure of which is incorporated herein by reference. ZSM-48, and the conventional preparation thereof, is taught by U.S. Pat. No. 4,375,573, incorporated herein by reference. Other examples of zeolite catalysts are described in U.S. Pat. Nos. 5,019,663 and 7,022,888, also incorporated herein by reference.

The dehydration catalyst may also be a bifunctional pentasil zeolite catalyst including at least one metallic element from the group of Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof, or a modifier from the group of Ga, In, Zn, Fe, Mo, Au, Ag, Y, Sc, Ni, P, Ta, lanthanides, and combinations thereof. The zeolite preferably has a strong acidic and dehydrogenation sites, and may be used with reactant streams containing and an oxygenated hydrocarbon at a temperature of below 500° C. The bifunctional pentasil zeolite may have ZSM-5, ZSM-8 or ZSM-11 type crystal structure consisting of a large number of 5-membered oxygen-rings, i.e., pentasil rings. The zeolite with ZSM-5 type structure is a particularly preferred catalyst. The bifunctional pentasil zeolite catalyst is preferably Ga and/or In-modified ZSM-5 type zeolites such as Ga and/or In-impregnated H-ZSM-5, Ga and/or In-exchanged H-ZSM-5, H-gallosilicate of ZSM-5 type structure and H-galloaluminosilicate of ZSM-5 type structure. The bifunctional ZSM-5 type pentasil zeolite may contain tetrahedral aluminum and/or gallium present in the zeolite. framework or lattice and octahedral gallium or indium. The octahedral sites are preferably not present in the zeolite framework but are present in the zeolite channels in a close vicinity of the zeolitic protonic acid sites, which are attributed to the presence of tetrahedral aluminum and gallium in the zeolite. The tetrahedral or framework Al and/or Ga is believed to be responsible for the acid function of zeolite and octahedral or non-framework Ga and/or In is believed to be responsible for the dehydrogenation function of the zeolite.

In one embodiment, the dehydration catalyst may be a H-galloaluminosilicate of ZSM-5 type bifunctional pentasil zeolite having framework (tetrahedral) Si/Al and Si/Ga mole ratio of about 20-1000 and 15-150, respectively, and non-framework (octahedral) Ga of about 0.5-5.0 wt. %. When these pentasil H-galloaluminosilicate zeolites are used as a dehydration catalyst, the density of strong acid sites can be controlled by the framework Al/Si mole ratio: the higher the Al/Si ratio, the higher the density of strong acid sites. The highly dispersed non-framework gallium oxide species can be obtained by the degalliation of the zeolite by its pretreatment with hydrogen and steam. The zeolite containing strong acid sites with high density and also highly dispersed non-framework gallium oxide species in close proximity of the zeolite acid site is preferred. The catalyst may optionally contain any binder such as alumina, silica or clay material. The catalyst can be used in the form of pellets, extrudates and particles of different shapes and sizes.

The specific $C_{2+}$ olefins produced will depend on various factors, including, without limitation, the type of oxygenates in the reactant stream, dehydration temperature, dehydration pressure, the reactivity of the catalyst, and the flow rate of the reactant stream as it affects the space velocity, GHSV and WHSV. Preferably, the reactant stream is contacted with the dehydration catalyst at a WHSV that is appropriate to produce the desired hydrocarbon products. The WHSV is preferably at least about 0.1 grams of oxygenate in the reactant stream per hour, more preferably the WHSV is between about 0.1 to 40.0 g/g hr, including a WHSV of about 1, 2, 3, 4, 5, 6, 7, 8, 9, 10, 11, 12, 13, 14, 15, 20, 25, 30, 35 g/g hr, and increments between.

The dehydration reaction should be carried out at a temperature at which the thermodynamics of the proposed reaction are favorable. For condensed phase liquid reactions, the pressure within the reactor must be sufficient to maintain at least a portion of the reactants in the condensed liquid phase at the reactor inlet. For vapor phase reactions, the reaction should be carried out at a temperature where the vapor pressure of the oxygenates is at least about 2 psia, and the thermodynamics of the reaction are favorable. The dehydration temperature will vary depending upon the specific oxygenate used, but is generally in the range of from about 100° C. to 500° C. for reactions taking place in the vapor phase, and more preferably from about 125° C. to 450° C. For liquid phase reactions, the alkylation temperature may be from about 80° C. to 500° C., and the dehydration pressure from about 0 psia to 900 psia. Preferably, the dehydration temperature is between about 100° C. and 500° C., or between about 125° C. and 450° C., or between about 150° C. and 350° C. The reaction pressure is preferably at least about 2 psia, or between about 0 and 900 psia, or between about 100 and 800 psia. In one embodiment, the dehydration temperature is in the range of about 100° C. to 500° C., and the dehydration pressure is in the range of about 0 psia to 900 psia. In another embodiment, the dehydration temperature is in the range of about 125° C. to 450° C., and the dehydration pressure is at least 2 psia. In another version, the dehydration temperature is in the range of about 150° C. to 350° C., and the dehydration pressure is in the range of about 100 psia to 800 psia. In yet another version, the dehydration temperature is in the range of about 175° C. to 325° C.

Alkylation

The $C_{6+}$ paraffins are produce by catalytically reacting in the liquid and/or vapor phase the $C_{2+}$ olefins with a stream of $C_{4+}$ isoparaffins in the presence of an alkylation catalyst at an alkylation temperature and alkylation pressure to produce a product stream including the $C_{6+}$ paraffins. Isoparaffins include, without limitation, alkanes having 4 to 7 carbon atoms, such as isobutane, isopentane, and higher homologues having a tertiary carbon atom (e.g., 2-methylbutane and 2,4-dimethylpentane), isomers of the foregoing, and mixtures thereof. The $C_{4+}$ isoparaffins may be internally generated $C_{4+}$ isoparaffins derived from the isomerization of $C_{4+}$ normal paraffins, aromatics and/or naphthenes in the reaction stream (internally generated $C_{4+}$ isoparaffins), or $C_{4+}$ isoparaffins provided solely from an external source (external $C_{4+}$ isoparaffins). The $C_{4+}$ isoparaffins may also be recycled $C_{4+}$ isoparaffins collected from the product stream having the $C_{6+}$ paraffins (recycled $C_{4+}$ isoparaffins).

The alkylation catalyst is generally a catalyst capable of converting $C_{2+}$ olefins and isoparaffins molecules into larger $C_{6+}$ paraffins. The alkylation catalyst may include, without limitation, sulfuric acid, hydrofluoric acid, aluminum chloride, boron trifluoride, solid phosphoric acid, chlorided alumina, alumina, aluminum phosphate, silica-alumina phosphate, amorphous silica-alumina, aluminosilicate, zirconia, sulfated zirconia, tungstated zirconia, tungsten carbide, molybdenum carbide, titania, sulfated carbon, phosphated carbon, phosphated silica, phosphated alumina, acidic resin, heteropolyacid, inorganic acid, and a combination thereof. The alkylation catalyst may also include a mixture of a mineral acid with a Friedel-Crafts metal halide, such as aluminum bromide, and other proton donors.

The alkylation catalyst may also be an aluminosilicate zeolite, or a bifunctional pentasil ring-containing aluminosilicate zeolite. Such catalysts may also include a modifier, such as Ga, In, Zn, Fe, Mo, Ag, Au, Ni, P, Sc, Y, Ta, a lanthanide, and combinations thereof, or a metal, such as Cu, Ag, Au, Pt, Ni, Fe, Co, Ru, Zn, Cd, Ga, In, Rh, Pd, Ir, Re, Mn, Cr, Mo, W, Sn, Os, an alloy thereof, and combinations thereof.

The specific $C_{6+}$ produced will depend on various factors, including, without limitation, the type and ratio of olefins and isoparaffins in the reactant stream, feedstock impurities, alkylation temperature, alkylation pressure, the reactivity of the alkylation catalyst, and the flow rate of the reactant stream as it affects the space velocity, GHSV and WHSV. Preferably, the reactant stream is contacted with the alkylation catalyst at a WHSV that is appropriate to produce the desired hydrocarbon products. For solid acid alkylation catalysts, the WHSV is preferably at least about 0.1 grams of olefin in the reactant stream per 1 gram of catalyst per hour, more preferably the WHSV is between about 0.1 to 40.0 g/g hr, including a WHSV of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 20, 25, 30, 35 g/g hr, and increments between. For alkylation catalysts based on liquid phase inorganic acids, the ratio of olefin in the reactant stream to inorganic acid present in the reactor at any given time is preferably at least about 0.05 grams of olefin in the reactant stream per 1 gram of inorganic acid per hour, more preferably, this ratio is between about 0.05 to 5 g/g hr, including ratios of about 0.05, 0.1, 0.2, 0.3, 0.4, 0.5, 0.6, 0.7, 0.8, 0.9, 1, 1.5, 2, 2.5, 3, 4, 5 g/g hr and increments between.

The alkylation reaction should be conducted at a temperature where the thermodynamics are favorable for the given catalyst and reaction stream. In general, the alkylation temperature is in the range of about -20° C. to 300° C., while the alkylation pressure is in the range of about 0 psig to 1200 psig. In one embodiment, the alkylation temperature is in the range of about 0° C. to 100° C., while the alkylation pressure is at least 100 psig. In yet another embodiment, the alkylation temperature is in the range of about 0° C. to 50° C., while the alkylation pressure is less than 300 psig. In still yet another embodiment, the alkylation temperature is in the range of about 70° C. to 250° C., and the alkylation pressure is in the range of about 100 psig to 1200 psig. In one embodiment, the alkylation catalyst is a mineral acid or a strong acid and the alkylation temperature is less than 80° C. In another embodiment, the alkylation catalyst is a zeolite and the alkylation temperature is greater than 100° C. Preferably, the alkylation temperature is in the range of about 100° C. to 300° C. for zeolite based alkylation catalysts.

The $C_{6+}$ paraffins produced are generally branched paraffins, but may also include normal paraffins. In general, the $C_{6+}$ branched paraffins may include branched $C_{6-10}$ alkanes, branched $C_6$ alkanes, branched $C_7$ alkanes, branched $C_8$ alkanes, branched $C_9$ alkanes, branched $C_{10}$ alkanes, and mixtures thereof. For example, the $C_{6+}$ branched paraffins may include, without limitation, dimethylbutane, 2,2-dimethylbutane, 2,3-dimethylbutane, methylpentane, 2-methylpentane, 3-methylpentane, dimethylpentane, 2,3-dimethylpentane, 2,4-dimethylpentane, methylhexane, 2.3-dimethylhexane, 2,3,4-trimethylpentane, 2,2,4-trimethylpentane(isooctane), 2,2,3-trimethylpentane, 2,3,3-trimethylpentane, dimethylhexane, or mixtures thereof.

Isomerization

The current method also produces $C_{4+}$ normal paraffins, aromatics and/or naphthenes throughout various stages of the process, whether as part of the oxygenate formation step, dehydration step or the alkylation step. Typically, the $C_{4+}$ normal paraffins include alkanes having 4 to 7 carbon atoms, such as n-butane, n-pentane, n-hexane, n-heptane, and mixtures thereof. The aromatics also generally have 6 or 7 carbons and may include, without limitation, benzene, and toluene, and mixtures thereof. The naphthenes generally contain 5 to 7 carbons and may include, without limitation, cyclopentane, methylcyclopentane, cyclohexane, dimethylcyclopentane, and methylcyclohexane. One aspect of the present invention is that the $C_{4+}$ normal paraffins, aromatics and/or naphthenes may be collected and converted to $C_{4+}$ isoparaffins for use in the alkylation step (internally generated $C_{4+}$ isoparaffins).

In one arrangement, an isomerization feedstock stream having the $C_{4+}$ normal paraffins, aromatics and/or naphthenes is collected upstream of the alkylation catalyst and processed for the production of the internally generated $C_{4+}$ isoparaffins. In this embodiment, the oxygenate reaction stream or dehydration reaction stream is passed through a separation mechanism that is capable of separating and collecting paraffins, aromatics and/or naphthenes from the reaction stream. Such processes are well known and often include techniques involving adsorption, extraction or extractive distillation. The UOP Olex process is one such application involving a selective adsorption technique that is capable of separating olefins and paraffins from liquid-phase mixtures.

In another arrangement, the $C_{4+}$ normal paraffins, aromatics and/or naphthenes are collected downstream of the alkylation catalyst and then recycled for use in the production of the internally generated $C_{4+}$ isoparaffins. In this embodiment, the $C_{4+}$ normal paraffins, aromatics and/or naphthenes pass unreacted through the alkylation process and are then collected from the resulting product stream containing the $C_{6+}$ paraffins using standard separation techniques.

Once collected, the $C_{4+}$ normal paraffins, aromatics and/or naphthenes are catalytically reacted in the presence of an isomerization catalyst at an isomerization temperature and isomerization pressure appropriate to produce the internally generated $C_{4+}$ isoparaffins. The reaction is typically conducted in the presence of hydrogen. Hydrogen is consumed in the conversion of naphthenes and aromatics to paraffins. It is also well known that hydrogen may accelerate the isomerization reactions while suppressing undesirable side reactions such as the formation of coke. The isomerization catalyst is generally a catalyst capable of catalyzing a $C_{4+}$ normal paraffin, aromatic and/or naphthene to produce a $C_{4+}$ isoparaffin. The isomerization catalyst may include, without limitation, a zeolite, zirconia, sulfated zirconia, tungstated zirconia, alumina, silica-alumina, zinc aluminate, chlorided alumina, phosphoric acid, or mixtures thereof. The isomerization catalyst may also be further modified to include a metal, such as Y, Pt, Ru, Pd, Ni, Rh, Ir, Fe, Co, Os, Zn, a lanthanide, or an alloy or combination thereof. In one embodiment, the isomerization catalyst is an acidic beta, mordenite, or ZSM-5 zeolite.

In certain embodiments, it may be preferential to adhere the isomerization catalyst to a support. Such supports may include, without limitation, alumina, sulfated oxide, clay, silica gel, aluminum phosphate, bentonite, kaolin, magnesium silicate, magnesium carbonate, magnesium oxide, aluminum oxide, activated alumina, bauxite, silica, silica-alumina, activated carbon, pumice, zirconia, titania, zirconium, titanium, kieselguhr, or zeolites. In one embodiment, the isomerization catalyst includes a support of a sulfated oxide or hydroxide of a Group IVB metal, at least one Group IIIA compound, and a Group VIII metal. The Group IVB metal may include zirconium, titanium, or mixtures thereof, and the Group IIIA compound may include gallium, indium, or mixtures thereof. In another version, the Group VIII metal includes Pd, Pt, Ru, Rh, Ir, Os, or mixtures thereof. In yet another version, the isomerization catalyst further includes Fe, Co, Ni, Re, Y, Eu, Tm, Ho, Er, Yb, Tb, or mixtures thereof.

The isomerization reaction should be conducted at a temperature where the thermodynamics are favorable. In one version, the isomerization temperature is in the range of about 100° C. to 250° C., and the isomerization pressure is in the range of about 100 psig to 800 psig. In another version, the isomerization temperature is in the range of about 125° C. to 225° C., and the isomerization pressure is in the range of about 100 psig to 1200 psig. In yet another version, the isomerization temperature is in the range of about 200° C. to 350° C., and the isomerization pressure is in the range of about 100 psig to 1200 psig.

The isomerization reaction should also be conducted at a temperature and pressure in view of the isomerization catalyst employed. In one embodiment, the isomerization catalyst comprises chlorided alumina modified by the addition of 0.01 to 5% of a Group VIII metal and the isomerization temperature is in the range of about 100° C. to 250° C., and the isomerization pressure is in the range of about 100 psig to 800 psig. Hydrogen is added with the feed to the reactor to achieve a hydrogen to hydrocarbon mole ratio of 0.01 to 10.0 at the reactor outlet. In another embodiment, the isomerization catalyst comprises a sulfated zirconia or tungstated zirconia modified with a Group VIII metal, and the isomerization temperature is in the range of about 125° C. to 225° C., and the isomerization pressure is in the range of about 100 psig to 1200 psig. Hydrogen is added with the feed to the reactor to achieve a hydrogen to hydrocarbon mole ratio of 0.01 to 10.0 at the reactor outlet. In another embodiment, the isomerization catalyst comprises a zeolite modified with a Group VIII metal, and the isomerization temperature is in the range of about 200° C. to 350° C., and the isomerization pressure is in the range of about 100 psig to 1200 psig. Hydrogen is added with the feed to the reactor to achieve a hydrogen to hydrocarbon mole ratio of 0.01 to 10.0 at the reactor outlet.

Catalyst Supports

In various embodiments above, the catalyst systems include a support suitable for suspending the catalyst in the feedstock solution. The support should be one that provides a stable platform for the chosen catalyst and the reaction conditions. The support may take any form which is stable at the chosen reaction conditions to function at the desired levels. Such supports include, without limitation, carbon, silica, silica-alumina, alumina, zirconia, titania, ceria, vanadia, nitride, boron nitride, heteropolyacids, kieselguhr, hydroxyapatite, zinc oxide, chromia, and mixtures of any two or more of the foregoing. Nanoporous supports such as zeolites, carbon nanotubes, or carbon fullerene may also be used.

One particularly preferred catalyst support is carbon, especially carbon supports having relatively high surface areas (greater than 100 square meters per gram). Such carbons include activated carbon (granulated, powdered, or pelletized), activated carbon cloth, felts, or fibers, carbon nanotubes or nanohorns, carbon fullerene, high surface area carbon honeycombs, carbon foams (reticulated carbon foams), and carbon blocks. The carbon may be produced via either chemical or steam activation of peat, wood, lignite, coal, coconut shells, olive pits, and petroleum based carbon. Another preferred support is granulated activated carbon produced from coconut shells. In one embodiment, the APR and deoxygenation catalyst system consists of Pt on carbon, with the Pt being further alloyed or admixed with Ni, Ru, Cu, Fe, Rh, Re, alloys and combinations thereof.

Another preferred catalyst support is zirconia. The zirconia may be produced via precipitation of zirconium hydroxide from zirconium salts, through sol-gel processing, or any other method. The zirconia is preferably present in a crystalline form achieved through calcination of the precursor material at temperatures exceeding 400° C. and may include both tetragonal and monoclinic crystalline phases. A modifying agent may be added to improve the textural or catalytic properties of the zirconia. Such modifying agents include, without limitation, sulfate, tungstenate, phosphate, titania, silica, and oxides of Group IIIB metals, especially Ce, La, or Y. In one embodiment, the APR and deoxygenation catalyst consists of Pt on a primarily monoclinic phase zirconia, with the Pt being further alloyed or admixed with Ni, Ru, Cu, Fe, Rh, Re, alloys and combinations thereof.

Yet another preferred catalyst support is titania. The titania may be produced via precipitation from titanium salts, through sol-gel processing, or any other method. The titania is preferably present in a crystalline form and may include both anatase and rutile crystalline phases. A modifying agent may be added to improve the textural or catalytic properties of the titania. Such modifying agents include, without limitation, sulfate, silica, and oxides of Group IIIB metals, especially Ce, La, or Y. In one embodiment, the APR and oxygenate forming catalyst system consists of Ru on a primarily rutile phase titania, with the Ru being further alloyed or admixed with Ge, Bi, B, Ni, Sn, Cu, Fe, Re, Rh, Pt, alloys and combinations thereof.

Another preferred catalyst support is silica. The silica may be optionally combined with alumina to form a silica-alumina material. In one embodiment, the APR catalyst system is Pt on silica-alumina or silica, with the Pt being further alloyed or admixed with Ni, Ru, Cu, Fe, Rh, Re, alloys and combinations thereof. In another embodiment, the APR catalyst system is Ni on silica-alumina or silica, with the nickel being further alloyed or admixed with Sn, Ge, Bi, Bu, Cu, Re, Ru, Fe, alloys and combinations thereof.

The support may also be treated or modified to enhance its properties. For example, the support may be treated, as by surface-modification, to modify surface moieties, such as hydrogen and hydroxyl. Surface hydrogen and hydroxyl groups can cause local pH variations that affect catalytic efficiency. The support may also be modified, for example, by treating it with sulfates, phosphates, tungstenates, silanes, lanthanides, alkali compounds or alkali earth compounds. For carbon supports, the carbon may be pretreated with steam, oxygen (from air), inorganic acids or hydrogen peroxide to provide more surface oxygen sites. The preferred pretreatment would be to use either oxygen or hydrogen peroxide. The pretreated carbon may also be modified by the addition of oxides of Group IVB and Group VB. It is preferred to use oxides of Ti, V, Zr and mixtures thereof.

The catalyst systems, whether alone or mixed together, may be prepared using conventional methods known to those in the art. Such methods include incipient wetting, evaporative impregnation, chemical vapor deposition, wash-coating, magnetron sputtering techniques, and the like. The method chosen to fabricate the catalyst is not particularly critical to the function of the invention, with the proviso that different catalysts will yield different results, depending upon considerations such as overall surface area, porosity, etc.

Supplemental Materials

Supplemental materials and compositions ("supplements") may be added to the feedstock solution at various stages of the process in order to enhance the reaction or to drive it to the production of the desired reaction products. Supplements may include, without limitation, acids, salts and additional hydrogen or feedstock. Such supplements may be added directly to the feedstock stream prior to or contiguous with contacting the relevant catalyst, or directly to the reaction bed for the appropriate reactions.

In one embodiment, the supplement may include an additional feedstock solution for providing additional oxygenated hydrocarbons for oxygenate formation. The feedstock may include any one or more oxygenated hydrocarbons listed above, including any one or more sugar alcohols, glucose, polyols, glycerol or saccharides. For instance, the supplemental material may include glycerol. In this embodiment, crude glycerol is used to initiate the reaction and to produce hydrogen so as to avoid polluting the deoxygenation catalyst with contaminants from the crude glycerol. Purified glycerol is then added to the feedstock solution prior to or at the same time the original feedstock solution is placed in contact with the deoxygenation catalyst to increase the oxygenated hydrocarbons available for processing. It is anticipated that the opposite may be employed with the crude glycerol serving as the supplement depending on the characteristics of the APR catalyst and deoxygenation catalyst.

In another embodiment, the supplement may include additional oxygenates for the condensation reaction. The oxygenates may include any one or more oxygenates listed above. For instance, the supplemental material may include a propyl alcohol. In this embodiment, the propyl alcohol may be produced in a parallel system from a glycerol feedstock and then combined with oxygenates produced by the processing of a sorbitol feedstock in order to provide a reactant stream most effective to produce a product containing a combination of $C_{6-12}$ hydrocarbons.

In yet another embodiment, the supplemental material may include recycled oxygenates and/or oxygenated hydrocarbons not fully reacted during the production process. The oxygenates and oxygenated hydrocarbons may include any one or more of oxygenates and oxygenated hydrocarbons listed above.

In still yet another embodiment, the supplemental material may include acids and salts added to the process. The addition of acidic compounds may provide increased selectivity to the desired oxygenates and, ultimately, $C_{4+}$ compounds. Water-soluble acids may include, without limitation, nitrate, phosphate, sulfate, chloride salts, and mixtures thereof. If an optional acidic modifier is used, it is preferred that it be present in an amount sufficient to lower the pH of the aqueous feed stream to a value between about pH 1.0 and about pH 4.0. Lowering the pH of a feed stream during oxygenate formation in this manner may increase the proportion of diols, polyols, ketones or alcohols for further condensation.

Reactor System

The reactions described herein may be carried out in any reactor of suitable design, including continuous-flow, batch, semi-batch or a combination of the foregoing, without limitation as to design, size, geometry, flow rates, etc. The reactor system may also use a fluidized catalytic bed system, a swing bed system, fixed bed system, a moving bed system, or a combination of the above. Preferably, the present invention is practiced utilizing a continuous-flow system at steady-state equilibrium.

In a continuous flow system, the reactor system includes at least a reforming bed adapted to receive an aqueous feedstock solution to produce hydrogen, a deoxygenation bed adapted to produce oxygenates from the hydrogen and a portion of the feedstock solution, a dehydration bed to produce $C_{2+}$ olefins from the oxygenates, and an alkylation bed to produce $C_{6+}$ paraffins from the $C_{4+}$ isoparaffins and $C_{2+}$ olefins. The reforming bed is configured to contact the aqueous feedstock solution in a vapor phase or liquid phase with the APR catalyst to provide hydrogen in a reactant stream. The deoxygenation bed is configured to receive the reactant stream for contact with the deoxygenation catalyst and production of the desired oxygenates. The dehydration bed is configured to receive the reactant stream for contact with the dehydration catalyst and production of $C_{2+}$ olefins. The alkylation reactor is configured to receive a reactant stream containing the $C_{2+}$ olefins (and in some instances, $C_{4+}$ normal paraffins, aromatics and/or naphthenes) and a stream of $C_{4+}$ isoparaffins for contact with the alkylation catalyst and the production of the desired paraffins. For systems not involving an APR hydrogen production step, the reforming bed may be removed. For systems not involving a hydrogen or oxygenate production step, the reforming and deoxygenation beds may be removed. Because the APR catalyst, deoxygenation catalyst and dehydration catalyst may also be atomically identical, the catalysts may exist as the same bed. For systems with a hydrogenation or hydrogenolysis step, an additional reaction bed may be included prior to the deoxygenation and/or reforming bed. For systems with a hydrogenation step prior to the dehydration step, an additional reaction bed may be included after the deoxygenation and/or reforming bed. For systems with an isomerization step, an additional isomerization bed may be provided and configured to receive an isoparaffin feedstock stream of $C_{4+}$ normal paraffins, aromatics and/or naphthenes for contact with the isomerization catalyst to produce a portion of the stream of $C_{4+}$ isoparaffins provided to the alkylation bed.

In systems producing both hydrogen and oxygenates, the dehydration bed may be positioned within the same reactor vessel along with the reforming bed or in a second reactor vessel in communication with a first reactor vessel having the reforming bed. The dehydration bed may be within the same reactor vessel along with the reforming or deoxygenation bed or in a separate reactor vessel in communication with the reactor vessel having the deoxygenation bed. Each reactor vessel preferably includes an outlet adapted to remove the product stream from the reactor vessel. In systems including a hydrogenation step or hydrogenolysis step, the hydrogenation or hydrogenolysis reaction bed may be within the same reactor vessel along with the reforming or deoxygenation bed or in a separate reactor vessel in communication with the reactor vessel having the reforming bed and/or deoxygenation bed. For systems with a hydrogenation step followed by a dehydration step, the hydrogenation reaction bed may be within the same reactor vessel along with the dehydration bed or in a separate reactor vessel in communication with the reactor vessel having the dehydration bed.

The reactor system may also include additional outlets to allow for the removal of portions of the reactant stream to further advance or direct the reaction to the desired reaction products, and to allow for the collection and recycling of reaction byproducts for use in other portions of the system. The reactor system may also include additional inlets to allow for the introduction of supplemental materials to further advance or direct the reaction to the desired reaction products, and to allow for the recycling of reaction byproducts for use in the reforming process. For example, the system may be designed such that excess hydrogen is produced over the APR catalyst, with a portion of the excess hydrogen removed and reintroduced downstream in a hydrogenation step to produce hydroxyl compounds for further dehydration. Alternatively, the system may be designed such that excess hydrogen is produced over the APR catalyst, with a portion of the excess hydrogen removed and used in other upstream processes, such as feedstock pretreatment processes and hydrogenation or hydrogenolysis reactions.

The reactor system may also include elements which allow for the separation of the reactant stream into different components which may find use in different reaction schemes or to simply promote the desired reactions. For instance, a separator unit, such as a phase separator, extractor, purifier or distillation column, may be installed prior to the alkylation, step to remove $C_{4+}$ normal paraffins, aromatics and/or naphthenes from the reactant stream for purposes of producing feed for an isomerization system to provide $C_{4+}$ isoparaffins for the alkylation reaction.

In one embodiment, the reaction system is configured such that the flow direction of the aqueous feedstock solution is established to ensure maximal interaction with the in-situ generated APR hydrogen. The reactor may be designed so that the reactant stream flows horizontally, vertical or diagonally to the gravitational plane so as to maximize the efficiency of the system. In systems where the reactant stream flows vertically or diagonally to the gravitational plan, the stream may flow either against gravity (up-flow system), with gravity (down-flow system), or a combination of both. In one preferred embodiment, the APR and/or deoxygenation reactor vessel is designed as an up-flow system while the dehydration reactor vessels are designed as a down-flow system. In this embodiment, the feedstock solution first contacts a reforming bed containing the APR catalyst to produce in-.sitit generated APR hydrogen. Due to the configuration of the reactor, the APR hydrogen is then able to, under certain conditions, percolate through a second reaction bed containing the deoxygenation catalyst at a rate, greater than or equal to the feedstock solution to maximize the interaction of the feedstock solution with the hydrogen and deoxygenation catalyst. The resulting reactant stream is then feed into the dehydration reactor in a down-flow configuration for processing.

Process Illustrations

Figure 4:
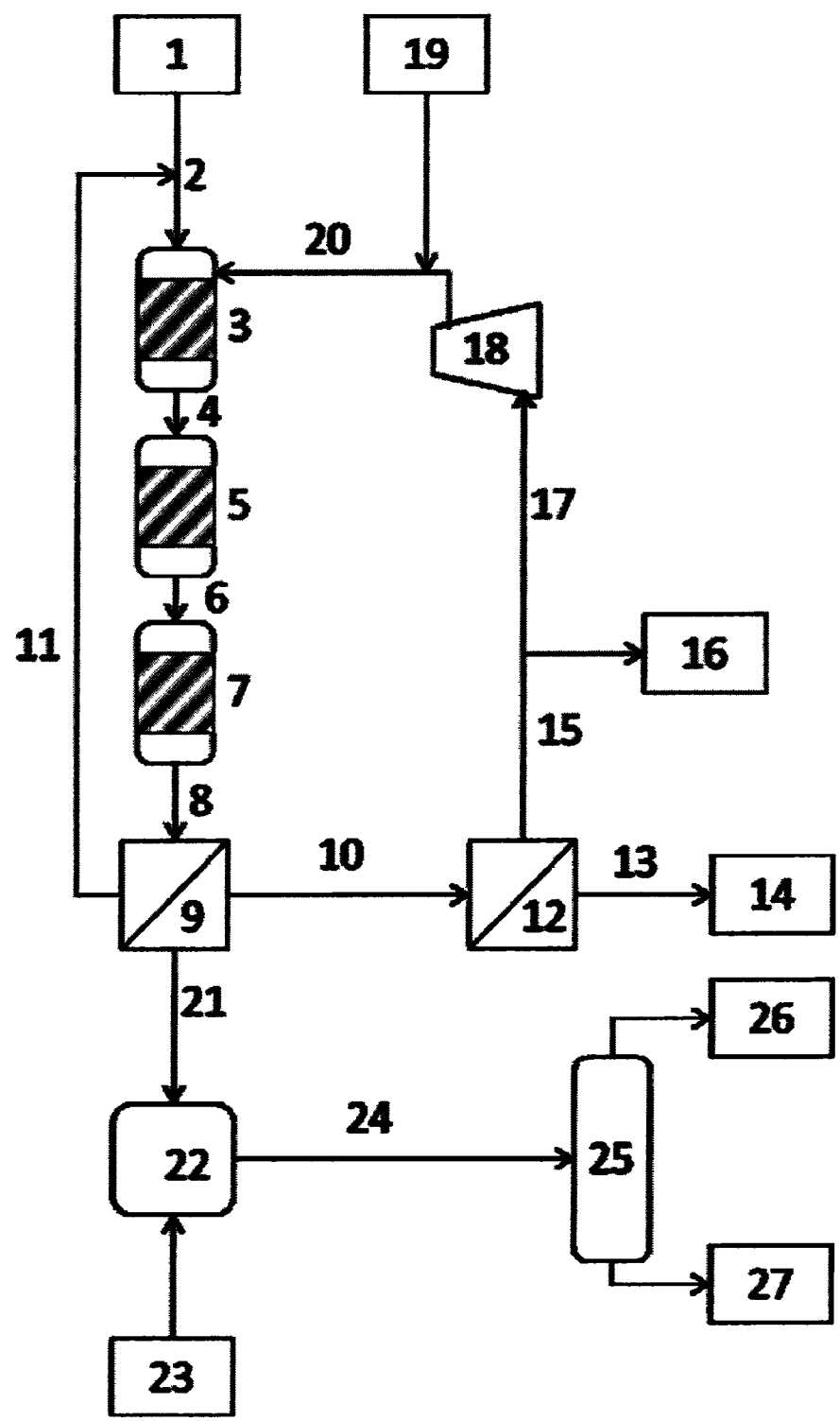
FIG. 4 is a flow diagram illustrating an embodiment of a reactor system.

FIG. 4 is a process diagram illustrating one potential reactor system useful in practicing the invention. A feed stream of oxygenated hydrocarbons 1 (with or without water) is mixed with a stream of recycled water and recycled oxygenates at 2 to provide an aqueous feedstock solution. The feedstock solution is hydrogenated or subjected to hydrogenolysis in reactor 3 containing hydrogenation or hydrogenolysis catalyst to provide a feedstock solution 4 that is more readily converted to the desired oxygenates. The hydrogen for the pretreatment may derive from an external source 18 or hydrogen recycled from the system as illustrated in steps below. The feedstock solution 4 is reacted in a reactor vessel 5 that contains an APR catalyst and a deoxygenation catalyst to produce APR product stream 6 containing water, APR hydrogen, carbon monoxide, carbon dioxide, hydrocarbons and oxygenates. Product stream 6 is then passed through reactor vessel 7, which includes a dehydration catalyst to produce product stream 8 containing $C_{2+}$ olefins, water, hydrogen, carbon dioxide and other hydrocarbons. Water in product stream 8 is then removed at separator 9 to provide a product stream 10 containing hydrogen, carbon dioxide and hydrocarbons and product stream 21 containing hydrocarbons including olefins. Water from dewatering step 9 is then recycled at 11 for mixing with the stream of oxygenated hydrocarbons at 2. Product stream 21 is then passed through reaction system 22, which includes an alkylation catalyst and a stream of $C_{4+}$ isoparaffins 23 that reacts with the $C_{2+}$ olefins to produce product stream 24 containing $C_{6+}$ paraffins, $C_{4+}$ isoparaffins, water, carbon dioxide and other hydrocarbons. Product stream 24 is then passed through a distillation column 25 to separate $C_{5+}$ hydrocarbons from 26 $C_{6+}$ alkylate product 27. The noncondensable gas stream 10 can be passed through a separation unit 11 to provide a purified hydrogen stream 15 and a raffinate stream 14 containing carbon dioxide, methane, ethane, propane, and some hydrogen. The purified hydrogen 15 may then be either exported from the system at 16 or passed through a recycle compressor 18 to provide recycled hydrogen stream 20.

Figure 5:
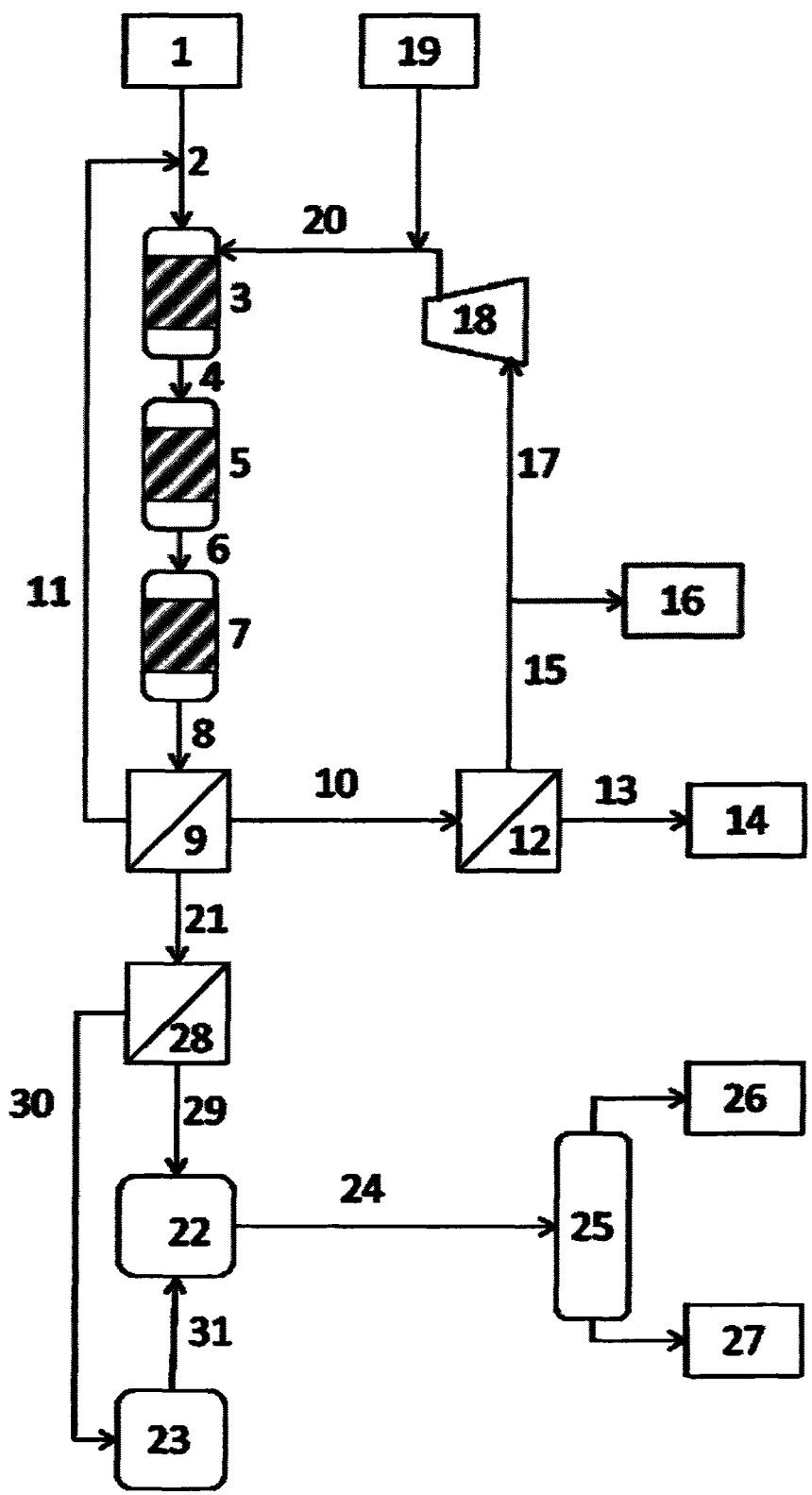
FIG. 5 is a flow diagram illustrating an embodiment of a reactor system.

FIG. 5 is a process diagram illustrating another potential reactor system useful in practicing the invention. The reactor system is similar to that illustrated by FIG. 4 except that a separation unit 28 is included after separator 9 for purposes of collecting the $C_{4+}$ normal paraffins, aromatics and/or naphthenes in isomerization feed stream 30. The isomerization feed stream 30 is then passed through a reaction system 23 that includes an isomerization catalyst to provide the stream of $C_{4+}$ isoparaffins 31 that reacts with the $C_{2+}$ olefins to produce product stream 24 containing the $C_{6+}$ paraffins, and other hydrocarbons.

Figure 6:
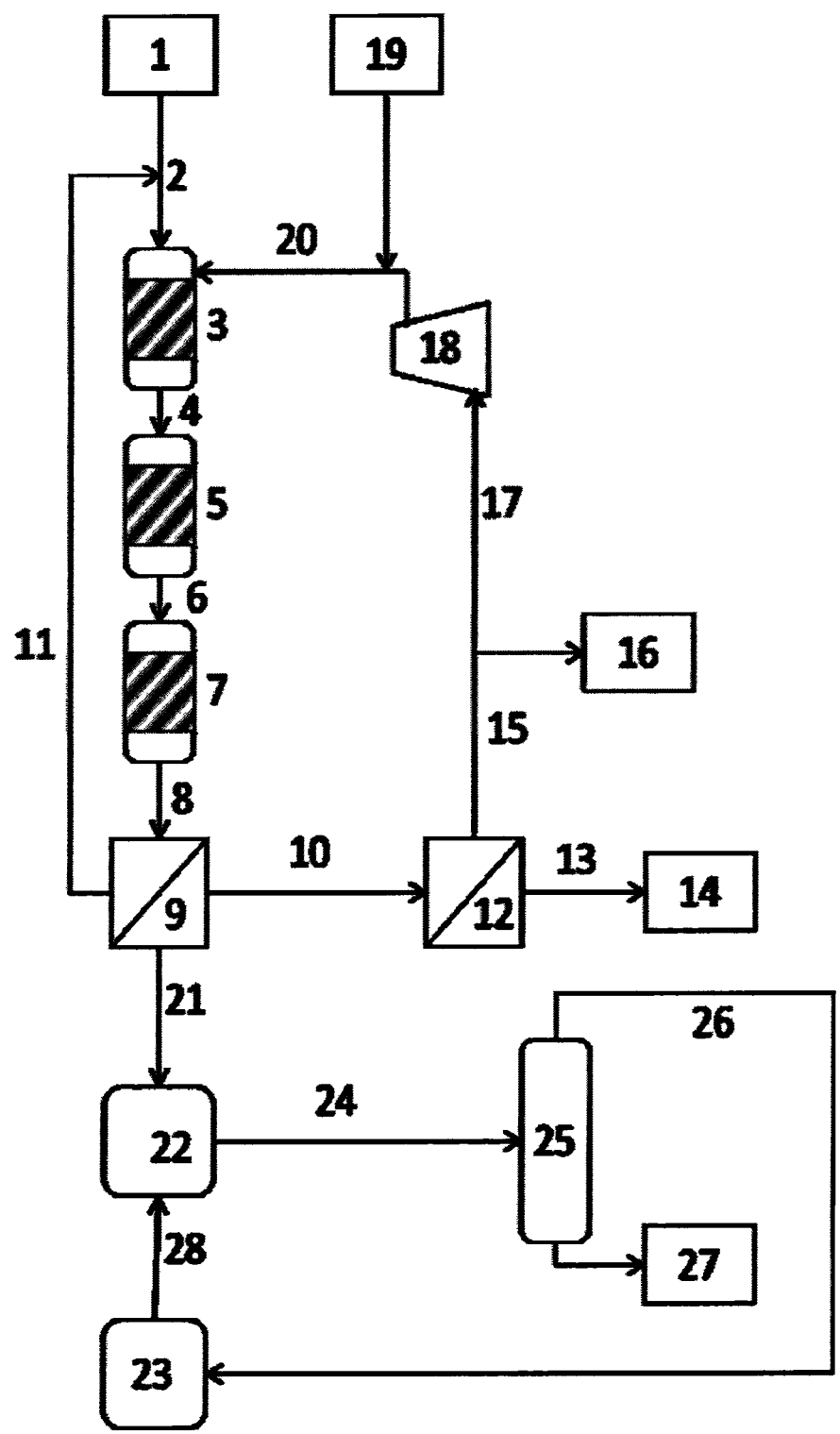
FIG. 6 is a flow diagram illustrating an embodiment of a reactor system.

FIG. 6 is a process diagram illustrating another potential reactor system useful in practicing the invention. The reactor system is similar to that illustrated by FIG. 4 except that stream 26 containing $C_{4+}$ normal paraffins, aromatics and/or naphthenes and excess $C_{4+}$ isoparaffins (recycled $C_{4+}$ isoparaffins) is fed to isomerization system 23. The isomerization feed 26 containing $C_{4+}$ normal paraffins, aromatics and/or naphthenes are isomerized in isomerization system 23 to provide the stream of $C_{4+}$ isoparaffins 28 that reacts with the $C_{2+}$ olefins to produce product stream 16 containing the $C_{6+}$ paraffins, water, carbon dioxide and other hydrocarbons.

Figure 7:
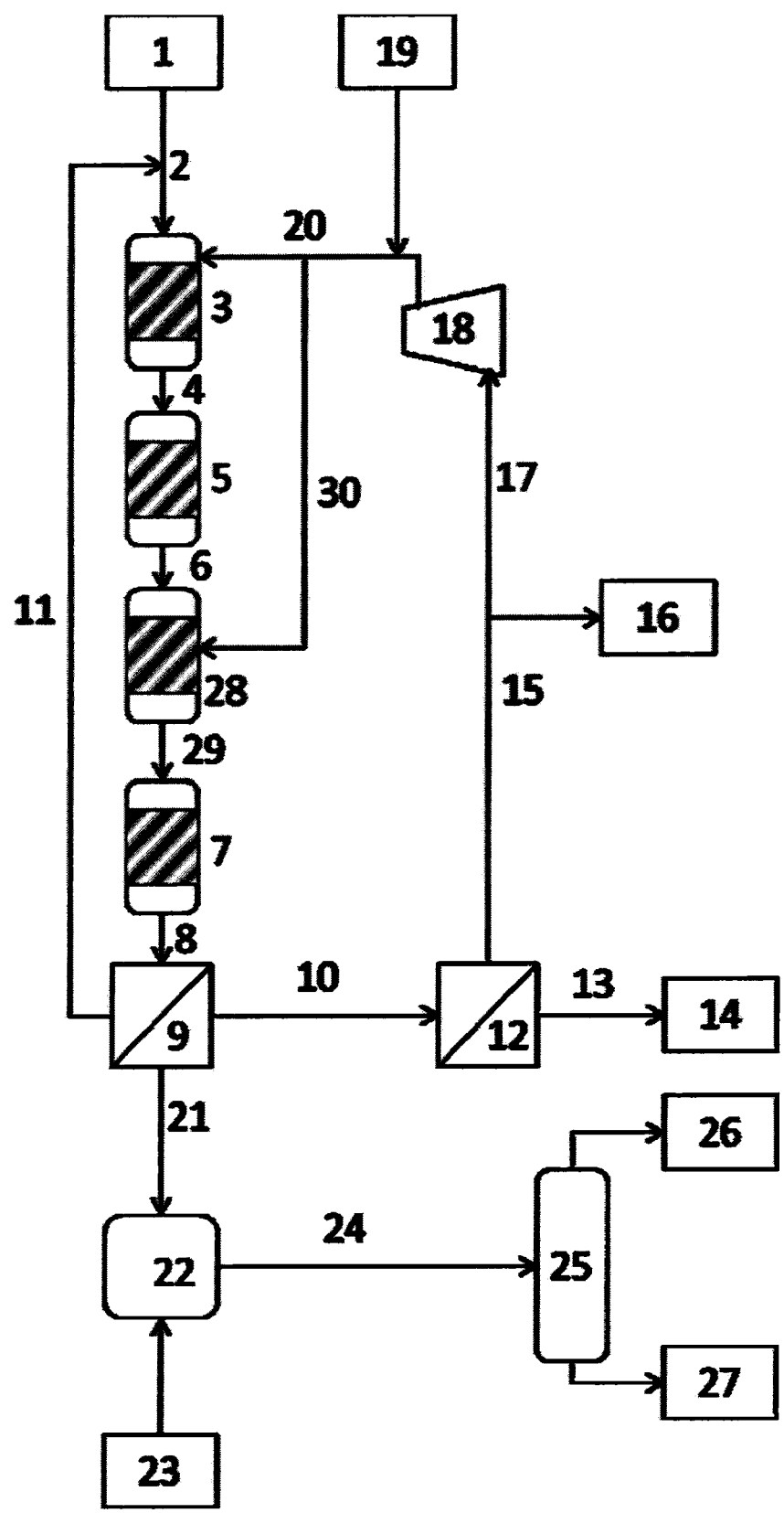
FIG. 7 is a flow diagram illustrating an embodiment of a reactor system.

FIG. 7 is a process diagram illustrating another potential reactor system useful in practicing the invention. The reactor system is similar to that illustrated by FIG. 4 except that product stream 6 is first passed through a hydrogenation reactor vessel 28, which includes a hydrogenation catalyst to produce product stream 29 containing $C_{2+}$ hydroxyl compounds, water, hydrogen carbon dioxide and other hydrocarbons. Supplemental hydrogen 30 for use in the hydrogenation reaction may be provided to reactor 28 from hydrogen stream 20. Product stream 29 is then passed through reactor vessel 7, which includes a dehydration catalyst to produce product stream 8 containing $C_{2+}$ olefins, water, hydrogen carbon dioxide and other hydrocarbons.

The following examples are included solely to provide a more complete disclosure of the subject invention. Thus, the following examples serve to illuminate the nature of the invention, but do not limit the scope of the invention disclosed and claimed herein in any fashion.

EXAMPLES

Example 1

APR/Deoxygenation Catalyst

A combined APR and deoxygenation catalyst was prepared by dissolving hexachloroplatinic acid and perrhenic acid in water and then adding the mixture to a monoclinic zirconia catalyst support (NorPro Saint-Gobain, Product code SZ31164, with particle sizes restricted to those that were maintained on a 60 mesh screen after passing through an 18 mesh screen) using an incipient wetness technique to target a platinum loading of 1.8% and a rhenium loading of 6.3% on the catalyst after subsequent decomposition of the metal precursors. The preparation was dried at 120° C. and subsequently calcined in a stream of flowing air at 400° C.

Example 2

Dehydration Catalyst

An aqueous nickel nitrate solution was added to an alumina bound ZSM-5 zeolite preparation ($SiO_2$:$Al_2O_3$ 30:1, 3 mm extrudates) using an evaporative impregnation technique to target a nickel loading of 1.0 weight %. The solution volume was three times the incipient wetness volume of the ZSM-5 material: The preparation was dried at 120° C. and then calcined in a stream of flowing air at 400° C.

Example 3

Conversion of Sorbitol to Oyxgenates

The catalyst system referenced in Example 1 was investigated for the conversion of sorbitol to an intermediate product containing oxygenates using a typical plug flow reactor system. The study was conducted using a 22.1 mm internal diameter Inconel reactor. The reactor pressure was varied between 625 and 1200 psig, while the reactor inlet temperature was varied between 190 and 265° C. The outlet temperature was varied between 185 and 230° C. by adjusting the air flow through a copper coil wrapped around the bottom of the reactor. The partial pressure of hydrogen in the reactor was varied between 625-1200 psig by adjusting the flow rate of the hydrogen stream co-fed with the sorbitol solution and by changing the total system pressure. The sorbitol concentration used was 50 wt %.

TABLE 1

Conversion of sorbitol to oxygenates.

| | Experiment A |
|---|---|
| Inlet Temperature (° C.) | 190-270 |
| Outlet Temperature (° C.) | 185-230 |
| Pressure (psig) | 625-1200 |
| WHSV (wt feed/wt catalyst hr) | 0.5-2 |
| Hydrogen Feed (mol $H_2$/mol sorbitol) | 0-1 |

Example 4

Conversion of Oxygenates to Olefins and Other Hydrocarbons

The catalyst system referenced in Example 2 was investigated for the conversion of the intermediate organic product made in Example 3 to an intermediate product containing a mixture of hydrocarbons and oxygenated hydrocarbons using a plug flow reactor system. The study was conducted using a 21.2 mm internal diameter stainless steel reactor. In all cases, the reactor pressure was maintained at 100 psig. The reactor inlet temperature was maintained at 370° C. and the outlet temperature was maintained at 360° C. The weight hourly space velocity (WHSV) was maintained at 0.8 g feed/(g catalyst hr).

Product streams were analyzed as follows. The organic liquid phase was collected and analyzed using either gas chromatograph with mass spectrometry detection or flame ionization detection. Component separation was achieved using a column with a bonded 100% dimethyl polysiloxane stationary phase. Relative concentrations of individual components were estimated via peak integration and dividing by the sum of the peak areas for an entire chromatogram. Compounds were identified by comparison to standard retention times and/or comparison of mass spectra to a compiled mass spectral database. Gas phase compositions were determined by gas chromatography with a thermal conductivity detector and flame ionization or mass spectrometry detectors for other gas phase components. The aqueous fraction was analyzed by gas chromatography with and without a derivatization of the organic components of the fraction using a flame ionization detector. Product yields are represented by the feed carbon present in each product fraction. The weight hourly space velocity (WHSV) was defined as the weight of feed introduced into the system per weight of catalyst per hour, and based on the weight of the oxygenated hydrocarbon feed only, excluding water present in the feed.

Figure 8:
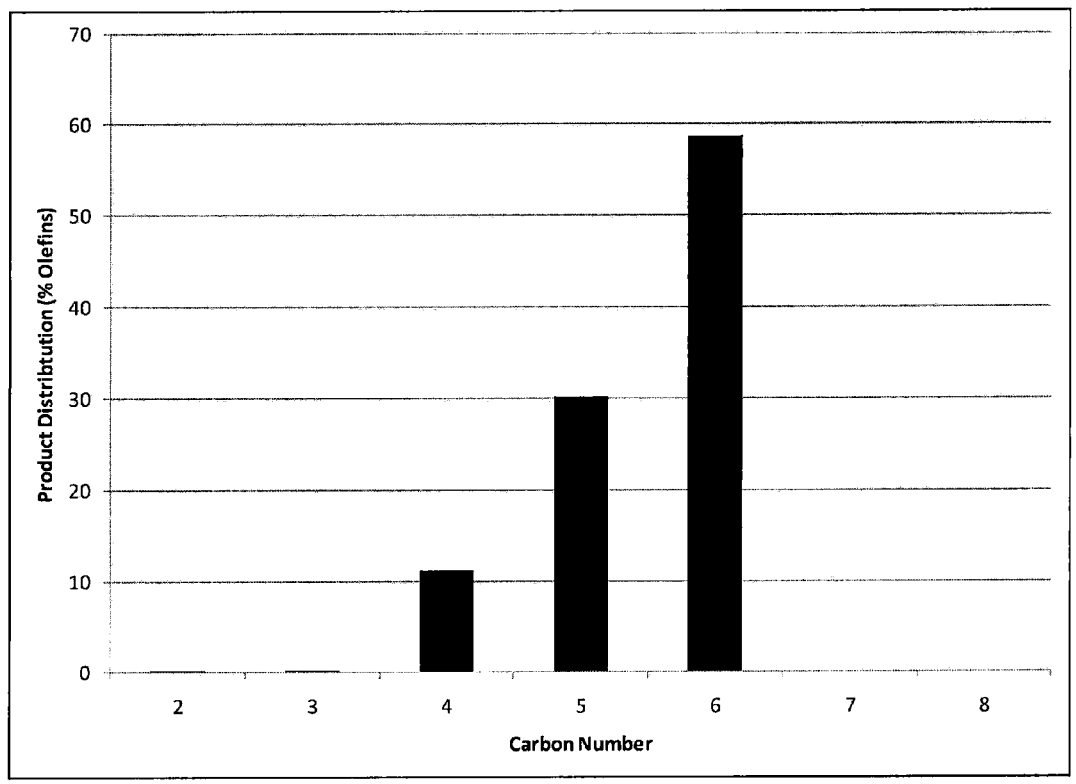
FIG. 8 is a chart illustrating the carbon distribution of olefins derived through the practice of one embodiment of the present invention.

After 57 hours of continuous operation, the reactor system was achieving yields of 49 wt % conversion to olefins, 17 wt % conversion to non-olefin hydrocarbons and 4 wt % conversion to oxygenated hydrocarbons. The olefins present after dehydration primarily consisted of $C_4$-$C_6$ species as illustrated in FIG. 8. Of the non-olefin hydrocarbons present, 8.2% consisted of $C_4$ and $C_5$ isoparaffins suitable for alkylation. Collectively, these components are capable of participating in alkylation reactions to form longer chain isoparaffins as described above. Iso-paraffins may also be generated in situ from the other reaction products.

We claim:

1. A method of making $C_{6+}$ paraffins comprising:
catalytically reacting hydrogen, water and water soluble oxygenated hydrocarbons comprising $C_{2+}O_{2+}$ hydrocarbons in the presence of a deoxygenation catalyst at a deoxygenation temperature and deoxygenation pressure to produce an oxygenate comprising $C_{2+}O_{1-3}$ hydrocarbons, wherein the $C_{2+}O_{2+}$ hydrocarbon comprises a member selected from the group consisting of a sugar alcohol, a sugar, a monosaccharide, a disaccharide, a polysaccharide, a cellulosic derivative, a lignocellulosic derivative, or a mixture of any two or more of the foregoing;
catalytically reacting the $C_{2+}O_{1-3}$ hydrocarbons in the presence of a dehydration catalyst at a dehydration temperature and dehydration pressure to produce a reaction stream comprising $C_{2+}$ olefins; and
reacting the $C_{2+}$ olefins with a stream of $C_{4+}$ isoparaffins in the presence of an alkylation catalyst at an alkylation temperature and alkylation pressure to produce a product stream comprising $C_{6+}$ paraffins.

2. The method of claim 1, wherein the $_{C2+}O_{2+}$ hydrocarbon comprises a member selected from the group consisting of a cellulose derivative, a lignin derivative, a hemicelluloses derivative, glucose, fructose, sucrose, maltose, lactose, mannose, xylose, arabitol, erythritol, glycerol, isomalt, lactitol, malitol, mannitol, sorbitol, xylitol, and a mixture of any two or more of the foregoing.

3. The method of claim 1, wherein the $C_{2+}O_{1-3}$ hydrocarbon comprises a member selected from the group consisting of an alcohol, ketone, aldehyde, furan, diol, triol, hydroxy carboxylic acid, carboxylic acid, and a mixture of any two or more of the foregoing.

4. The method of claim 1, wherein the $C_{6+}$ paraffin comprises a member selected from the group consisting of branched $C_{6-10}$ alkane, a branched $C_6$ alkane, a branched $C_7$ alkane, a branched C$_8$ alkane, a branched C$_9$ alkane, a branched C$_{10}$ alkane, or a mixture of any two or more of the foregoing.

5. The method of claim 1, wherein the deoxygenation catalyst comprises a support and a member selected from the group consisting of Re, Cu, Fe, Ru, Ir, Co, Rh, Pt, Pd, Ni, W, Os, Mo, Ag, Au, an alloy of any two or more of the foregoing, or a combination of any two or more of the foregoing.

6. The method of claim 5, wherein the deoxygenation catalyst further comprises a member selected from the group consisting of Mn, Cr, Mo, W, V, Nb, Ta, Ti, Zr, Y, La, Sc, Zn, Cd, Ag, Au, Sn, Ge, P, Al, Ga, In, Tl, and a combination of any two or more of the foregoing.

7. The method of claim 5, wherein the support comprises a member selected from group consisting of a nitride, carbon, silica, alumina, zirconia, titania, vanadia, ceria, boron nitride, heteropolyacid, kieselguhr, hydroxyapatite, zinc oxide, chromia, and mixtures of any two or more of the foregoing.

8. The method of claim 7, wherein the support comprises a member selected from the group consisting of carbon nanotubes, carbon fullerenes, and zeolites.

9. The method of claim 1, wherein the dehydration catalyst comprises a member selected from the group consisting of an acidic alumina, aluminum phosphate, silica- alumina phosphate, amorphous silica-alumina, aluminosilicate, zirconia, sulfated zirconia, tungstated zirconia, tungsten carbide, molybdenum carbide, titania, sulfated carbon, phosphated carbon, phosphated silica, phosphated alumina, acidic resin, heteropolyacid, inorganic acid, and a combination of any two or more of the foregoing.

10. The method of claim 9, wherein the dehydration catalyst further comprises a modifier selected from the group consisting of Ce, Y, Sc, La, Li, Na, K, Rb, Cs, Mg, Ca, Sr, Ba, P, B, Bi, and a combination of any two or more of the foregoing.

11. The method of claim 9, wherein the dehydration catalyst further comprises an oxide of an element, the element selected from the group consisting of Ti, Zr, V, Nb, Ta, Mo, Cr, W, Mn, Re, Al, Ga, In, Fe, Co, Ir, Ni, Si, Cu, Zn, Sn, Cd, P, and a combination of any two or more of the foregoing.

12. The method of claim 9, wherein the dehydration catalyst further comprises a metal selected from the group consisting of Cu, Ag, Au, Pt, Ni, Fe, Co, Ru, Zn, Cd, Ga, In, Rh, Pd, Ir, Re, Mn, Cr, Mo, W, Sn, Os, an alloy of any two or more of the foregoing, and a combination of any two or more of the foregoing.

13. The method of claim 9, wherein the dehydration catalyst comprises an aluminosilicate zeolite.

14. The method of claim 13, wherein the dehydration catalyst further comprises a modifier selected from the group consisting of Ga, In, Zn, Fe, Mo, Ag, Au, Ni, P, Sc, Y, Ta, a lanthanide, and a combination of any two or more of the foregoing.

15. The method of claim 13, wherein the dehydration catalyst further comprises a metal selected from the group consisting of Cu, Ag, Au, Pt, Ni, Fe, Co, Ru, Zn, Cd, Ga, In, Rh, Pd, Ir, Re, Mn, Cr, Mo, W, Sn, Os, an alloy of any two or more of the foregoing, and a combination of any two or more of the foregoing.

16. The method of claim 1, wherein the alkylation catalyst comprises a member selected from the group consisting of sulfuric acid, hydrofluoric acid, aluminum chloride, boron trifluoride, solid phosphoric acid, chlorided alumina, acidic alumina, aluminum phosphate, silica-alumina phosphate, amorphous silica-alumina, aluminosilicate, aluminosilicate zeolite, zirconia, sulfated zirconia, tungstated zirconia, tungsten carbide, molybdenum carbide, titania, sulfated carbon, phosphated carbon, phosphated silica, phosphated alumina, acidic resin, heteropolyacid, inorganic acid, a mixture of a mineral acid and a Friedel-Crafts metal halide, and a combination of any two or more of the foregoing.

17. The method of claim 16, wherein the alkylation catalyst further comprises a modifier selected from the group consisting of Ga, In, Zn, Fe, Mo, Ag, Au, Ni, P, Sc, Y, Ta, a lanthanide, and a combination of any two or more of the foregoing.

18. The method of claim 16, wherein the alkylation catalyst further comprises a metal selected from the group consisting of Cu, Ag, Au, Pt, Ni, Fe, Co, Ru, Zn, Cd, Ga, In, Rh, Pd, Ir, Re, Mn, Cr, Mo, W, Sn, Os, an alloy of any two or more of the foregoing, and a combination of any two or more of the foregoing.

19. The method of claim 1, wherein the dehydration catalyst and the alkylation catalyst are atomically identical.

20. The method of claim 1, wherein at least a portion of the hydrogen is an APR hydrogen produced by a method comprising catalytically reacting a first portion of the water and the water soluble oxygenated hydrocarbon in the presence of an APR catalyst at a reforming temperature and a reforming pressure to produce the APR hydrogen.

21. The method of claim 20, wherein the APR catalyst comprises a support and a member selected from the group consisting of Fe, Ru, Os, Ir, Co, Rh, Pt, Pd, Ni, an alloy of any two or more of the foregoing, and a combination of any two or more of the foregoing.

22. The method of claim 21, wherein the APR catalyst further comprises a member selected from the group consisting of Cu, B, Mn, Re, Cr, Mo, Bi, W, V, Nb, Ta, Ti, Zr, Y, La, Sc, Zn, Cd, Ag, Au, Sn, Ge, P, Al, Ga, In, Tl, an alloy of any two or more of the foregoing, and a combination of any two or more of the foregoing.

23. The method of claim 21, wherein the support comprises a member selected from group consisting of a nitride, carbon, silica, alumina, zirconia, titania, vanadia, ceria, boron nitride, heteropolyacid, kieselguhr, hydroxyapatite, zinc oxide, chromia, and mixtures of any two or more of the foregoing.

24. The method of claim 21, wherein the support comprises a member selected from the group consisting of carbon nanotubes, carbon fullerenes, and zeolites.

25. The method of claim 20, wherein one or more of the APR catalyst, deoxygenation catalyst, and dehydration catalyst are atomically identical.

26. The method of claim 20, wherein the APR catalyst and deoxygenation catalyst comprise Pt alloyed or admixed with a member selected from the group consisting of Ni, Ru, Cu, Fe, Rh, Re, alloys of any two or more of the foregoing, and a combination of any two or more of the foregoing.

27. The method of claim 20, wherein the APR catalyst and deoxygenation catalyst comprise Ru alloyed or admixed with a member selected from the group consisting of Ge, Bi, B, Ni, Sn, Cu, Fe, Rh, Pt, alloys of any two or more of the foregoing, and a combination of any two or more of the foregoing.

28. The method of claim 20, wherein the APR catalyst comprises Ni alloyed or admixed with a member selected from the group consisting of Sn, Ge, Bi, B, Cu, Re, Ru, Fe, alloys of any two or more of the foregoing, and a combination of any two or more of the foregoing.

29. The method of claim 1 further comprising the step of providing an aqueous solution comprising water and a polysaccharide, disaccharide, monosaccharide, sugar, furfural, carboxylic acid, ketone, furan, or a combination of any two or more of the foregoing, and catalytically reacting the polysaccharide, disaccharide, monosaccharide, sugar, furfural, carboxylic acid, ketone, furan, or combination, with hydrogen in the presence of a hydrogenation catalyst at a hydrogenation temperature and hydrogenation pressure to produce the water soluble oxygenated hydrocarbon.

30. The method of claim 29, wherein the hydrogenation catalyst comprises a support and a member selected from the group consisting of Fe, Ru, Os, Ir, Co, Rh, Pt, Pd, Ni, Re, Cu, alloys of any two or more of the foregoing, and a combination of any two or more of the foregoing.

31. The method of claim 30, wherein the hydrogenation catalyst further comprises a member selected from the group consisting of Ag, Au, Cr, Zn, Mn, Sn, Bi, Mo, W, B, P, alloys of any two or more of the foregoing, and a combination of any two or more of the foregoing.

32. The method of claim 1 further comprising the step of providing an aqueous solution comprising water and a polysaccharide, disaccharide, monosaccharide, polyhydric alcohol, sugar, sugar alcohol, or a combination of any two or more of the foregoing, and catalytically reacting the sugar, sugar alcohol, polysaccharide, disaccharide, monosaccharide, polyhydric alcohol, or combination, with hydrogen in the presence of a hydrogenolysis catalyst at a hydrogenolysis temperature and hydrogenolysis pressure to produce the water soluble oxygenated hydrocarbon.

33. The method of claim 32, wherein the hydrogenolysis catalyst comprises a member selected from the group consisting of phosphate, Cr, Mo, W, Re, Mn, Cu, Cd, Fe, Ru, Os, Ir, Co, Rh, Pt, Pd, Ni, alloys of any two or more of the foregoing, and a combination of any two or more of the foregoing.

34. The method of claim 33, wherein the hydrogenolysis catalyst further comprises a member selected from the group consisting of Au, Ag, Zn, Sn, Bi, B, Cr, Mn, O, alloys of any two or more of the foregoing, and a combination of any two or more of the foregoing.

35. The method of claim 33, wherein the hydrogenolysis catalyst further comprises an alkaline earth metal oxide.

36. The method of claim 1 wherein the step of catalytically reacting hydrogen, water and water soluble oxygenated hydrocarbons in the presence of a deoxygenation catalyst is performed in either a liquid phase, a vapor phase, or a combination of the foregoing.

37. The method of claim 1, wherein the $C_{2+}O_{2+}$ hydrocarbon further comprises a recycled $C_{2+}O_{2+}$ hydrocarbon.

38. A method of making a $C_{6+}$ paraffins comprising: catalytically reacting hydrogen, water and water soluble oxygenated hydrocarbons comprising $C_{2+}O_{2+}$ hydrocarbons in the presence of a deoxygenation catalyst at a deoxygenation temperature and deoxygenation pressure to produce an oxygenate comprising $C_{2+}O_{1-3}$ hydrocarbons and one or more $C_{4+}$ normal paraffins, aromatics and/or naphthenes, wherein the $C_{2+}O_{2}+$ hydrocarbon comprises a member selected from the group consisting of a sugar alcohol, a sugar, a monosaccharide, a disaccharide, a polysaccharide, a cellulosic derivative, a lignocellulosic derivative, or a mixture of any two or more of the foregoing;

collecting a portion of the $C_{4+}$ normal paraffins, aromatics and/or naphthenes and catalytically reacting the $C_{4+}$ normal paraffins, aromatics and/or naphthenes in the presence of an isomerization catalyst to produce a stream of $C_{4+}$ isoparaffins;

catalytically reacting the $C_{2+}O_{1-3}$ hydrocarbons in the presence of a dehydration catalyst at a dehydration temperature and dehydration pressure to produce a reaction stream comprising $C_{2+}$ olefins; and catalytically reacting the $C_{2+}$ olefins with the $C_{4+}$ isoparaffins in the presence of an alkylation catalyst at an alkylation temperature and alkylation pressure to produce a product stream comprising $C_{6+}$ paraffins.

39. The method of claim 38, wherein at least a portion of the hydrogen is an APR hydrogen produced by a method comprising catalytically reacting a first portion of the water and the water soluble oxygenated hydrocarbon in the presence of an APR catalyst at a reforming temperature and a reforming pressure to produce the APR hydrogen.

40. The method of claim 38 further comprising the step of providing an aqueous solution comprising water and a polysaccharide, disaccharide, monosaccharide, sugar, furfural, carboxylic acid, ketone, furan, or a combination of any two or more of the foregoing, and catalytically reacting the polysaccharide, disaccharide, monosaccharide, sugar, furfural, carboxylic acid, ketone, furan, or combination of any two or more of the foregoing, with hydrogen in the presence of a second hydrogenation catalyst at a hydrogenation temperature and hydrogenation pressure to produce the water soluble oxygenated hydrocarbon.

41. The method of claim 38 further comprising the step of providing an aqueous solution comprising water and a polysaccharide, disaccharide, monosaccharide, polyhydric alcohol, sugar, sugar alcohol, or a combination of any two or more of the foregoing, and catalytically reacting the sugar, sugar alcohol, polysaccharide, disaccharide, monosaccharide, polyhydric alcohol, or combination of any two or more of the foregoing, with hydrogen in the presence of a hydrogenolysis catalyst at a hydrogenolysis temperature and hydrogenolysis pressure to produce the water soluble oxygenated hydrocarbon.

42. The method of claim 38, wherein the isomerization catalyst comprises a member selected from the group consisting of a zeolite, zirconia, sulfated zirconia, tungstated zirconia, alumina, silica-alumina, zinc aluminate, chlorided alumina, phosphoric acid, and combinations of any two or more of the foregoing.

43. The method of claim 42, wherein the isomerization catalyst is an acidic beta, mordenite, or a ZSM-5 zeolite.

44. The method of claim 42, wherein the isomerization catalyst further comprises a metal selected from the group consisting of Y, Pt, Ru, Pd, Ni, Rh, Ir, Fe, Co, Os, Zn, a lanthanide, or an alloy or combination of any two or more of the foregoing.

45. The method of claim 42, wherein the isomerization catalyst comprises a support, the support comprising alumina, sulfated oxide, clay, silica gel, aluminum phosphate, bentonite, kaolin, magnesium silicate, magnesium carbonate, magnesium oxide, aluminum oxide, activated alumina, bauxite, silica, silica-alumina, activated carbon, pumice, zirconia, titania, zirconium, titanium, kieselguhr, or zeolites.

46. The method of claim 45, wherein the isomerization catalyst comprises a support of a sulfated oxide or hydroxide of a Group IVB metal, at least one Group IIIA compound, and a Group VIII metal.

47. The method of claim 46, wherein the Group IVB metal comprises, zirconium, titanium, alloys of the foregoing, or mixtures of the foregoing, and the Group IIIA compound comprises gallium, indium, or mixtures of the foregoing.

48. The method of claim 46, wherein the Group VIII metal comprises Pd, Pt, Ru, Rh, Ir, Os, allows of any two or more of the foregoing, or mixtures of any two or more of the foregoing.

49. The method of claim 42, wherein the isomerization catalyst further includes Fe, Co, Ni, Re, Y, Eu, Tm, Ho, Er, Yb, Tb, or mixtures of any two or more of the foregoing.

50. The method of claim 38, wherein the $C_{2+}O_{2+}$ hydrocarbon comprises a member selected from the group consisting of a cellulose derivative, a lignin derivative, a hemicelluloses derivative, glucose, fructose, sucrose, maltose, lactose, mannose, xylose, arabitol, erythritol, glycerol, isomalt, lactitol, malitol, mannitol, sorbitol, xylitol, and a mixture of any two or more of the foregoing.

51. The method of claim 38, wherein the $C_{2+}O_{2+}$ hydrocarbon further comprises a recycled $C_{2+}O_{2+}$ hydrocarbon.

52. A method of making a $C_{6+}$ paraffins comprising:
catalytically reacting hydrogen, water and water soluble oxygenated hydrocarbons comprising $C_{2+}O_{2+}$ hydrocarbons in the presence of a deoxygenation catalyst at a deoxygenation temperature and deoxygenation pressure to produce an oxygenate comprising $C_{2+}O_{1-3}$ hydrocarbons, wherein the $C_{2+}O_{2+}$ hydrocarbon comprises a member selected from the group consisting of a sugar alcohol, a sugar, a monosaccharide, a disaccharide, a polysaccharide, a cellulosic derivative, a lignocellulosic derivative, or a mixture of any two or more of the foregoing;
catalytically reacting the $C_{2+}O_{1-3}$ hydrocarbons in the presence of a dehydration catalyst at a dehydration temperature and dehydration pressure to produce a reaction stream comprising $C_{2+}$ olefins and one or more $C_{4+}$ normal paraffins, aromatics and/or naphthenes;
collecting a portion of the $C_{4+}$ normal paraffins, aromatics and/or naphthenes and catalytically reacting the $C_{4+}$ normal paraffins, aromatics and/or naphthenes in the presence of an isomerization catalyst to produce a stream of $C_{4+}$ isoparaffins; and
catalytically reacting the $C_{2+}$ olefins with the $C_{4+}$ isoparaffins in the presence of an alkylation catalyst at an alkylation temperature and alkylation pressure to produce a product stream comprising $C_{6+}$ paraffins.

53. The method of claim 52, wherein at least a portion of the hydrogen is an APR hydrogen produced by a method comprising catalytically reacting a first portion of the water and the water soluble oxygenated hydrocarbon in the presence of an APR catalyst at a reforming temperature and a reforming pressure to produce the APR hydrogen.

54. The method of claim 52 further comprising the step of providing an aqueous solution comprising water and a polysaccharide, disaccharide, monosaccharide, sugar, furfural, carboxylic acid, ketone, furan, or a combination of any two or more of the foregoing, and catalytically reacting the polysaccharide, disaccharide, monosaccharide, sugar, furfural, carboxylic acid, ketone, furan, or combination, with hydrogen in the presence of a second hydrogenation catalyst at a hydrogenation temperature and hydrogenation pressure to produce the water soluble oxygenated hydrocarbon.

55. The method of claim 52 further comprising the step of providing an aqueous solution comprising water and a polysaccharide, disaccharide, monosaccharide, polyhydric alcohol, sugar, sugar alcohol, or a combination of any two or more of the foregoing, and catalytically reacting the sugar, sugar alcohol, polysaccharide, disaccharide, monosaccharide, polyhydric alcohol, or combination, with hydrogen in the presence of a hydrogenolysis catalyst at a hydrogenolysis temperature and hydrogenolysis pressure to produce the water soluble oxygenated hydrocarbon.

56. The method of claim 52, wherein the $C_{2+}O_{2+}$ hydrocarbon comprises a member selected from the group consisting of a cellulose derivative, a lignin derivative, a hemicelluloses derivative, glucose, fructose, sucrose, maltose, lactose, mannose, xylose, arabitol, erythritol, glycerol, isomalt, lactitol, malitol, mannitol, sorbitol, xylitol, and a mixture of any two or more of the foregoing.

57. The method of claim 52, wherein the $C_{2+}O_{2+}$ hydrocarbon further comprises a recycled $C_{2+}O_{2+}$ hydrocarbon.

* * * * *